US008106172B2

(12) United States Patent
Sillekens et al.

(10) Patent No.: US 8,106,172 B2
(45) Date of Patent: Jan. 31, 2012

(54) NUCLEIC ACID SEQUENCES THAT CAN BE USED AS PRIMERS AND PROBES IN THE AMPLIFICATION AND DETECTION OF SARS CORONAVIRUS

(75) Inventors: Peter T. G. Sillekens, Gemonde (NL); Marlieke Overdijk, Helmond (NL); Saskia van de Laar, Boxtel (NL)

(73) Assignee: Biomerieux, B.V., Boxtel (NL)

( * ) Notice: Subject to any disclaimer, the term of this patent is extended or adjusted under 35 U.S.C. 154(b) by 883 days.

(21) Appl. No.: 10/559,949

(22) PCT Filed: Mar. 8, 2004

(86) PCT No.: PCT/EP2004/002553
§ 371 (c)(1),
(2), (4) Date: Dec. 22, 2006

(87) PCT Pub. No.: WO2004/111274
PCT Pub. Date: Dec. 23, 2004

(65) Prior Publication Data
US 2009/0226885 A1 Sep. 10, 2009

(30) Foreign Application Priority Data
Jun. 10, 2003 (EP) ..................................... 03101676

(51) Int. Cl.
*C07H 21/04* (2006.01)
*C12Q 1/68* (2006.01)
*C12P 19/34* (2006.01)

(52) U.S. Cl. .................. 536/23.1; 536/24.33; 536/24.31; 435/6.12; 435/91.2

(58) Field of Classification Search .................. 536/23.1, 536/24.33, 24.31; 435/6, 91.2, 6.12
See application file for complete search history.

(56) References Cited

U.S. PATENT DOCUMENTS
7,374,883 B2 * 5/2008 Laue .................................. 435/6
2004/0265796 A1 * 12/2004 Briese et al. ...................... 435/5

FOREIGN PATENT DOCUMENTS
| CN | 458281 A | 11/2003 |
| WO | WO 01/47944 | 7/2001 |
| WO | WO 02/066501 | 8/2002 |

OTHER PUBLICATIONS

Lowe et al. Nucleic acid research, 1990, vol. 18(7), p. 1757.*
Sequence search reports.*
Attached sequence search reports.*
The nucleic acid sequence search reports for SEQ ID Nos. 3-4, 7-8, 25 and 29.*
Zhou et al. 2003. "One-step duplex RT-PCR assay for detection SARS associated coronavirus" *Virologica Siniga* 18:232-236 (English abstract only).

Yang et al. 2003. "Clinical detection of polymerase gene of SARS-associated coronavirus" *Academic Journal of the First Military Medical University* 23:424-427 (English abstract only).
Drosten et al. 2003. "Identification of a novel coronavirus in patients with severe acute respiratory syndrome" *New England Journal of Medicine* 348:1967-1976.
Shi et al. 2003. "Design and application of 60mer oligonucleotide microarray in SARS coronavirus detection" *Chinese Science Bulletin* 48:1165-1169.
Kim et al. 2001. "Cloning and characterization of novel genes related with the development of rat brain" *EMBL Database Accession No. AT005537.*
Deiman et al. 2002. "Characteristics and applications of nucleic acid sequence-based amplification (NASBA)" *Molecular Biotechnology* 20:163-179.
Ksiazek et al. 2003. "A novel coronavirus associated with severe acute respiratory syndrome" *New England Journal of Medicine* 348:1953-1966.
International Search Report for PCT Application No. PCT/EP2004/002553, mailed Jan. 12, 2004.
Bitsch et al. "Cytomegalovirus Transcripts in Peripheral Blood Leukocytes of Actively Infected Transplant Patients Detected by Reverse Transcription-Polymerase Chain Reaction" *The Journal of Infectious Diseases* 167:740-743 (1993).
CDC "Update: Outbreak of Severe Acute Respiratory Syndrome" *MMWR* 52(12):241-248 (2003).
Compton, J. "Nucleic acid sequence-based amplification" *Nature* 350:91-92 (1991).
Kenten et al. "Improved Electrochemiluminescent Label for DNA Probe Assays: Rapid Quantitative Assays of HIV-1 Polymerase Chain Reaction Products" *Clin. Chem.* 38(6):873-879 (1992).
Lai et al. "Coronaviridae: The Viruses and Their Replication" *Fundamental Virology*, editors-in-chief David M. Knipe and Peter M. Howley, 4th ed., Philadelphia, Lippincott Williams & Wilkins 1163-1185 (2001).
Lee et al. "A Major Outbreak of Severe Acute Respiratory Syndrome in Hong Kong" *The New England Journal of Medicine* 348(20):1986-1994 (2003).

(Continued)

*Primary Examiner* — Kenneth R. Horlick
*Assistant Examiner* — Joyce Tung
(74) *Attorney, Agent, or Firm* — Myers, Bigel, Sibley & Sajovec, P.A.

(57) ABSTRACT

The present invention is related to nucleic acid sequences that can be used in the field of virus diagnostics, more specifically the diagnosis of infections with a novel human coronavirus causing Severe Acute Respiratory Syndrome (SARS). With the present invention nucleotide sequences are provided that can be used as primers and probes in the amplification and detection of SARS nucleic acid. The oligonucleotide sequences provided with the present invention are located in the replicase gene, the nucleocapsid gene and the 3' end non-coding region of the SARS Coronavirus genome. It has been found that, by using the sequences of the present invention in methods for the amplification and detection of nucleic acid a sensitive and specific detection of SARS Coronavirus can be obtained. The oligonucleotide sequences according to the present invention are especially useful in methods for the amplification of nucleic acid.

21 Claims, 60 Drawing Sheets

OTHER PUBLICATIONS

Marra et al. "The Genome Sequence of the SARS-Associated Coronavirus" *Science* 300:1399-1404 (2003).

Meyer et al. "Identification of active cytomegalovirus infection by analysis of immediate-early, early and late transcripts in peripheral blood cells of immunodeficient patients" *Molecular and Cellular Probes* 8:261-271 (1994).

Poutanen et al. "Identification of Severe Acute Respiratory Syndrome in Canada" *The New England Journal of Medicine* 348(20):1995-2005 (2003).

Rota et al. "Characterization of a Novel Coronavirus Associated with Severe Acute Respiratory Syndrome" *Science* 300:1394-1399 (2003).

Saiki et al. "Enzymatic Amplification of β-Globin Genomic Sequences and Restriction Site Analysis for Diagnosis of Sickle Cell Anemia" *Science* 230:1350-1354 (1985).

Sawicki et al. "A New Model for Coronavirus Transcription" *Adv Exp Med Biol* 440:215-219 (1998).

Tsang et al. "A Cluster of Cases of Severe Acute Respiratory Syndrome in Hong Kong" *The New England Journal of Medicine* 348(20):1977-1985 (2003).

Tyagi et al. "Molecular Beacons: Probes that Fluoresce upon Hybridization" *Nature Biotechnology* 14:303-308 (1996).

World Health Organization bulletin "Acute respiratory syndrome in China" (Feb. 11, 2003) http://www.who.int/csr/don/2003_02_11/en/print.html (2007).

World Health Organization bulletin "Acute respiratory syndrome in China—Update" (Feb. 12, 2003) http://www.who.int/csr/don/2003_02_12a/en/print.html (2007).

Zuker et al. "Mfold web server for nucleic acid folding and hybridization prediction" *Nucleic Acids Research* 31(13):3406-3415 (2003).

International Preliminary Report on Patentability for International Application No. PCT/EP2004/002553, dated Sep. 28, 2005 (12 pages).

Tapp et al. "Homogeneous Scoring of Single-Nucleotide Polymorphisms: Comparison of the 5'-Nuclease TaqMan® Assay and Molecular Beacon Probes" *BioTechniques* 28:732-738 (2000).

* cited by examiner dG = -3.3  *SARS CoV REP MB-1 dG = −2.7    SARS-CoV 3'-NCR MB-1

FIG. 41

NUCLEIC ACID SEQUENCES THAT CAN BE USED AS PRIMERS AND PROBES IN THE AMPLIFICATION AND DETECTION OF SARS CORONAVIRUS

RELATED APPLICATIONS

The present application is a 35 U.S.C. §371 national phase application of PCT International Application No. PCT/EP2004/002553, having an international filing date of Mar. 8, 2004 and claiming priority to European Patent Application No. 03101676.9, filed Jun. 10, 2003, the disclosures of each of which are incorporated herein by reference in their entireties. The above PCT application was published in the English language and has International Publication No. WO 2004/111274.

The present invention is related to nucleic acid sequences that can be used in the field of virus diagnostics, more specifically the diagnosis of infections with a novel human coronavirus causing Severe Acute Respiratory Syndrome (SARS).

An outbreak of atypical pneumonia, referred to as SARS, was first identified in late 2002 in Guangdong Province, China (Marra et al. (1) or Rota et al. (2)). After similar cases were detected in patients in Hong Kong, Vietnam, and Canada during February and March 2003, the World Health Organization (WHO) issued a global alert for the illness. By May $22^{nd}$, 2003, over 8000 SARS cases and 682 SARS-related deaths were reported to WHO from over 30 countries around the world.

Most of these cases were related to exposure to SARS patients in residential or healthcare settings. The incubation period for the disease usually ranges from 2 to 7 days. Infection is usually characterized by fever and flu-like symptoms, which are followed a few days later by a dry, non-productive cough, and shortness of breath. Death from progressive respiratory failure occurs in about 3% to nearly 10% of cases (3-7).

Conventional diagnostic kits could authorize the detection of antibodies produced in response to the SARS coronavirus infection. Different types of antibodies (IgM and IgG) appear and change in level during the course of infection. They can be undetectable at the early stage of infection. Immunoglobulin G usually remains detectable after resolution of the illness. The following test formats are being developed, but are not commercially available yet:

Enzyme Linked ImmunoSorbant Assay (ELISA): a test detecting a mixture of IgM and IgG antibodies in the serum of SARS patients yields positive results reliably at around day 21 after the onset of illness, and Immunofluorescence Assay (IFA): a test detecting IgM antibodies in serum of SARS patients yields positive results after about day 10 of illness; this test format is also used to test for IgG; this is a reliable test requiring the use of fixed SARS virus infected cell cultures, studied under an immunofluorescence microscope.

Positive antibody test results indicate a previous infection with SARS-Coronavirus. Seroconversion from negative to positive or a four-fold rise in antibody titre from acute to convalescent serum indicates recent infection. With negative antibody test results, no detection of antibody after 21 days from onset of illness seems to indicate that no infection with SARS-Coronavirus took place.

Clearly, the current generation of SARS antibody tests, which use the immunofluorescence and ELISA techniques, have a sensitivity problem. Immunofluorescence can only detect the antibodies after a patient has carried the disease for at least 10 days, while for ELISA, about 20 days are needed. During that time, the patient may have spread the virus to other people. In that context, the tests are mainly useful after hospitalisation, for confirming whether a patient has SARS. That is the reason why these tests are not very useful for infectious disease control. Thus the need exists for a bedside test, a quick on-the-spot test which allows the detection (from secretions) at an early stage of the disease or the detection of early antibodies, say from day five (of infection) onwards.

Another conventional detection method is constituted by cell cultures. Virus in specimens (such as respiratory secretions, blood or stool) from SARS patients can also be detected by inoculating cell cultures and growing the virus. Once isolated, the virus must be identified as the SARS virus with further tests. Cell culture is a very demanding test, but currently (with the exception of animal trials) the only means to show the existence of a live virus. Positive cell culture results indicate the presence of live SARS-Coronavirus in the sample tested. Negative cell culture results do not exclude SARS. Moreover these two conventional techniques (detection of antibodies and cell culture) require a laboratory and trained staff as well as time to carry out the test. These tests are good and robust in scientific laboratories but they are not rapid enough to have an efficient diagnosis in due time.

Whereas conventional virus diagnosis has been based predominantly on the detection of viral antigens or specific antibodies thereto, in recent years attention has shifted towards methods for the direct and rapid detection of the genome of viruses or nucleic acid sequences derived thereof, both RNA and DNA. In this respect, the very short time-to-result is a crucial factor to opt for nucleic acid detection. These methods are usually based on nucleic acid hybridization. Nucleic acid hybridization is based on the ability of two strands of nucleic acid containing complementary sequences to anneal to each other under the appropriate conditions, thus forming a double stranded structure. When the complementary strand is labeled, the label can be detected and is indicative for the presence of the target sequence. Especially in combination with methods for the amplification of nucleic acid sequences these methods have become an important tool in viral diagnosis.

Nucleic acid amplification techniques are especially useful as an additional technique in cases where serological methods give doubtful results or in cases where there may be a considerable time period between infection and the development of antibodies to the virus. With HIV for example, seroconversion usually can occur some 3-6 weeks after exposure to the virus. Thus, whereas no antibodies will be detected with conventional immunoassays, proviral DNA or circulating viral RNA may already be detectable. Also in monitoring antiviral therapy, methods based on nucleic acid amplification have several advantages over serological methods. Especially quantitative amplification methods provide a powerful tool in assessing the changes in the amount of virus present before and during therapy.

The choice of the oligonucleotides to be used as primers and probes in the amplification and detection of nucleic acid sequences is critical for the sensitivity and specificity of the assay. The sequence to be amplified is usually only present in a sample (for example a blood sample obtained from a patient suspected of having a viral infection) in minute amounts. The primers should be sufficiently complementary to the target sequence to allow efficient amplification of the viral nucleic acid present in the sample. If the primers do not anneal properly (due to mispairing of the bases on the nucleotides in both strands) to the target sequence, amplification is seriously hampered. This will affect the sensitivity of the assay and may result in false negative test results. Due to the heterogeneity of viral genomes false negative test results may be obtained if the primers and probes are capable of recognizing sequences present in only part of the variants of the virus.

Various techniques for amplifying nucleic acid are known in the art. One example of a technique for the amplification of a DNA target segment is the so-called "polymerase chain reaction" (PCR). With the PCR technique the copy number of a particular target segment is increased exponentially with a number of cycles. A pair of primers is used and in each cycle a DNA primer is annealed to the 3' side of each of the two strands of the double stranded DNA-target sequence. The primers are extended with a DNA polymerase in the presence of the various mononucleotides to generate double stranded DNA again. The strands of the double stranded DNA are separated from each other by thermal denaturation and each strand serves as a template for primer annealing and subsequent elongation in a following cycle. The PCR method has been described in Saiki et al., Science 230, 135, 1985 and in patents EP-B-0.200.362 and EP-A-0.201.184.

Another technique for the amplification of nucleic acid is the so-called transcription based amplification system (TAS). The TAS method is described in WO-A-88/10315. Transcription based amplification techniques usually comprise treating target nucleic acid with two oligonucleotides one of which comprises a promoter sequence, to generate a template including a functional promoter. Multiple copies of RNA are transcribed from said template and can serve as a basis for further amplification.

An isothermal continuous transcription based amplification method is the so-called NASBA process ("NASBA") as described in EP-B-0.329.822. NASBA includes the use of T7 RNA polymerase to transcribe multiple copies of RNA from a template including a T7 promoter. Other transcription based amplification techniques are described in EP-A-0.408.295. EP-A-0.408.295 is primarily concerned with a two-enzyme transcription based amplification method. Transcription based amplification methods, such as the NASBA method as described in EP-A-0.329.822, are usually employed with a set of oligonucleotides, one of which is provided with a promoter sequence that is recognized by a DNA dependent RNA polymerase such as, for example, T7 RNA polymerase. Several modifications of transcription-based techniques are known in the art. These modifications comprise, for example, the use of blocked oligonucleotides (that may be provided with a promoter sequence). These oligonucleotides are blocked so as to inhibit an extension reaction proceeding there from (U.S. Pat. No. 5,554,516). One or more "promoter-primers" (oligonucleotides provided with a promoter sequence) may be used in transcription based amplification techniques, overlap with the BNI-1 and BNI-2 sequences (Ksiazek et al. (13)).

When primers specifically targeting the BNI-1 fragment and the CDC fragment were used in a long-range PCR protocol, a region extending from the CDC fragment to the BNI-1 fragment was amplified. The obtained fragment had the expected length of 3 kb. It was sequenced from both ends, and the sequences were found to be identical to the CDC and BNI-1 sequences, respectively, demonstrating that the two sequences were derived from a contiguous RNA molecule and, thus, from the same virus. Since the same virus was isolated from two independent cases of SARS, and since there was serologic evidence of an acute infection with this virus in the underlying patients, it was considered that the coronavirus might have a role in causing SARS. Specific diagnostic assays based on RT-PCR were therefore established for the detection of the pathogen.

However, PCR and RT-PCR also have problems. Drosten et al. (10) developed a diagnostic method for SARS that makes use of a nested set of primers designed within the BNI-1 fragment. The outer set of primers detected the virus in clinical specimens from the index patient and different patients, who also had clinical signs of SARS. Additional specimens were positive on nested RT-PCR. To have a practical and quantitative test, a real-time RT-PCR with a 5'-nuclease probe was established. After optimization with the use of quantified RNA transcribed in vitro, the assay reliably detected 10 copies of RNA per reaction, corresponding to 830 RNA molecules per milliliter of specimen. The sensitivities of nested and real-time PCR were equivalent.

The specificity of the PCR with outer primers of the nested PCR, and of the real-time PCR was tested with the use of RNA purified from cultures of bovine coronavirus, avian infectious coronavirus, porcine transmissible gastroenteritis coronavirus and human coronaviruses 229E and OC43. None of the optionally combined with the use of one or more oligonucleotides that are not provided with a promoter sequence. For RNA amplification, a transcription based amplification technique, is a preferred technology.

Amplification using PCR can also be based on an RNA template. The actual PCR needs to be preceded by a reverse transcription step to copy the RNA into DNA (RT-PCR). However, if RT-PCR is used for the detection of viral transcripts, differentiation of mRNA- and DNA-derived PCR products is necessary. DNAse treatment prior to RT-PCR can be employed (Bitsch et al. (8); Meyer et al. (9)), but sometimes fails to remove contaminating DNA sufficiently (Bitsch et al. (8)). That is the solution advocated by Drosten et al. (10) for the detection of the SARS Coronavirus. Thus by performing random amplification with fifteen different PCRs under low-stringency conditions and including, an initial reverse-transcription step to detect RNA viruses, about twenty distinct DNA fragments were obtained and sequenced. Three of the fragments did not match any nucleotide sequence in the database (www.ncbi.nlm.nih.gov:80/BLAST). In a translated BLAST search these fragments showed homology to coronavirus amino acid sequences. Two of the fragments were 300 nucleotides in length and identical in sequence, and the third fragment was 90 nucleotides in length (sequences BNI-1 and BNI-2, respectively, as reported on the Web site of the WHO network on March 25). Detailed sequence analysis revealed that both fragments were located in the open reading frame 1b of coronaviruses. The novel coronavirus isolate was termed FFM-ic (for Frankfurt am Main index case).

Simultaneously, a group at the Centers for Disease Control and Prevention (CDC), Atlanta, USA identified a 400-nucleotide coronavirus fragment (Urbani isolate, reported on the Web site of the WHO network on March 24). This sequence did not show an PCR assays cross-reacted with these viruses—a finding that is consistent with their considerable genetic differences from the novel coronavirus. Quantification of the viral RNA concentration in clinical specimens from the index patient and Contact 1 by real-time PCR revealed that the highest concentration—as high as 100 million copies per milliliter—was present in sputum. After enrichment of virus by ultra centrifugation, viral RNA was also detected in the serum of the index patient, indicating the presence of low-level viremia during symptomatic disease. Both the index patient and Contact 1 had viral RNA in stool samples obtained during late convalescence, suggesting that virus may be shed in faeces for prolonged periods of time. To investigate whether the novel coronavirus was prevalent in patients in Germany who had gastrointestinal symptoms, a collection of fifty-four stored stool samples was tested with the use of the real-time RT-PCR assay. None of the samples tested positive.

The established PCR assays have also been used to test respiratory samples from German patients with symptoms and a travel history compatible with SARS. So far, sixty-seven samples from fifty-five patients have been tested. One patient fulfilling the WHO criteria for probable SARS was coronavirus-positive on PCR. PCR protocols, as well as positive control material, have been made available to laboratories worldwide. Until standardized reagents for virus and antibody detection are available and methods have been adequately field tested, SARS diagnosis remains based on the clinical and epidemiological findings: acute febrile illness with respiratory symptoms not attributed to another cause and a history of exposure to a suspect or probable case of SARS or their respiratory secretions and other bodily fluids. Those requirements are reflected in the current WHO case definitions for suspect or probable SARS.

Researchers in several countries are working towards developing fast and accurate laboratory diagnostic tests for the SARS-Coronavirus. Molecular tests based on PCR amplification are one of the faster and more accurate tests that could achieve this goal.

Polymerase chain reaction (PCR) can detect genetic material of the SARS-Coronavirus in various specimens (blood, stool, respiratory secretions or body tissues). Same primers, which are the key pieces for a PCR test, have been made publicly available by WHO network laboratories on the WHO web site. A ready-to-use PCR test kit containing primers and a positive and negative control has been developed. Testing of the kit by network members is expected to quickly yield the data needed to assess the test's performance, in comparison with primers developed by other WHO network laboratories and in correlation with clinical and epidemiological data. Principally, existing PCR tests are very specific but lack sensitivity. This means that negative tests cannot rule out the presence of the SARS virus in patients. Furthermore, contamination of samples in laboratories in the absence of laboratory quality control can lead to false positive results. Positive PCR results, with the necessary quality control procedures in place, are very specific and mean that there is genetic material (RNA) of the SARS-Coronavirus in the sample. This does not mean that there is live virus present, or that it is present in a quantity large enough to infect another person. Negative PCR results do not exclude SARS. SARS-Coronavirus PCR can be negative for the following reasons:

the patient is not infected with the SARS coronavirus; the illness is due to another infectious agent (virus, bacterium, fungus) or a non-infectious cause, the test results are incorrect ("false-negative"). Current tests need to be further developed to improve sensitivity, specimens were not collected at a time when the virus or its genetic material was present. The virus and its genetic material may be present for a brief period only, depending on the type of specimen tested, specimens were not properly handled prior to nucleic acid extraction and nucleic acids have become deteriorated.

It is the purpose of this invention to provide reagents and methods to realise kits for diagnosing SARS disease earlier than former kits. The use of the oligonucleotides according to the invention is not limited to any particular amplification technique or any particular modification thereof, however these oligonucleotides permit amplification of RNA by using a transcription-based amplification technique, preferably the NASBA. Our primers sets are very efficient compared to the RT-PCR primers. In contrast to RT-PCR, NASBA, which is based on RNA transcription by T7 RNA polymerase (Kievits et al. (11); Compton (12)), does not need differentiation between RNA- and DNA-derived amplification products since it uses RNA as its principal target. RT-PCR for SARS have a too low sensitivity, often nested PCR protocol needed to achieve satisfying sensitivity. The nested protocol is then riskful in terms of contamination, i.e. falses positives. NASBA can achieve sensitivity comparable to nested protocol in a "one-step" amplification avoiding risk for contamination.

The oligonucleotides of the present invention can likewise be used in quantitative amplification methods. An example if such quantitative method is described in EP-A-0.525.882. The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone instead of the phosphate sugar backbone of normal nucleic acid) or the like. It is evident that these alternative structures, representing the sequences of the present invention are likewise part of the present invention.

The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary or homologous to the target sequence, but somewhat longer primers are preferred. Usually primers contain about 15-28 nucleotides, preferably 20-26 nucleotides, but longer primers may also be employed, especially when the primers contain additional sequences such as a promoter sequence for a particular polymerase.

Normally a set of primers will consist of at least two primers, one "upstream" primer and one "downstream" primer, which together define the amplicon (the sequence that will be amplified using said primers).

Primarily for the use in transcription based amplification techniques, the oligonucleotides according to the invention may also be linked to a promoter sequence. The term "promoter sequence" defines a region of a nucleic acid sequence that is specifically recognized by an RNA polymerase that binds to a recognized sequence and initiates the process of transcription by which an RNA transcript is produced. In principle any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Oligonucleotides linked to a promoter sequence are commonly referred to as "promoter primers". Their function as a primer, e.g. the starting point for an elongation reaction, however, may be blocked, as already mentioned above, or absent in some embodiments of transcription based amplification reactions.

It is understood that oligonucleotides consisting of the sequences of the present invention may contain minor deletions, additions and/or substitutions of nucleic acid bases, to the extent that such alterations do not negatively affect the yield or product obtained to a significant degree. Where oligonucleotides according to the present invention are used as probes, the alterations should not result in lowering the hybridization efficiency of the probe. For example, in case of transcription based amplification techniques, wherein one or more of the primers may be provided with a promoter sequence, the introduction of a purine-rich (=G or A) hybridizing sequence, just after the promoter sequence may have positive effects on the transcription (when there are C's and T's abortive transcription may occur). If no such sequence is available in the target nucleic acid a purine-rich sequence can be inserted in the oligonucleotide just following the last three G residues of the promoter sequence.

The sequences of the present invention are reflected as DNA sequences. The RNA equivalents of these sequences are likewise part of the present invention.

An aspect of the invention is a pair of oligonucleotides, for use as a set in the amplification of a target sequence of the genome of SARS Coronavirus, said pair consisting of: a first oligonucleotide being 10-50 nucleotides in length and comprising at least a fragment of 10 nucleotides of:

```
SEQ ID 1:
TACCTCTCCA GCTAGGATTT TCTACAGGTG TTAACTTAGT

AGCTGTACCG ACTGGTTATG TTGACACTGA AAATAACACA

GAATTCACCA GAGTTAATGC AAAACCTCCA CCAGGTGACC

AGTTTAAACA TCTT,

SEQ ID 14:
TCAGCCCCAG ATGGTACTTC TATTACCTAG GAACTGGCCC

AGAAGCTTCA CTT,

SEQ ID 23:
TGCTCCAAGT GCCTCTGCAT TCTTTGGAAT GTCACGCATT

GGCATGGAAG TCACACCTT,
or

SEQ ID 31:
TGCCTATATG GAAGAGCCCT AATGTGTAAA ATTAATTTTA

GTAGTGCTAT CCCCATGTGA TTTTAATAGC TT,
``` or the complementary sequence thereof, a second oligonucleotide being 10-50 nucleotides in length and comprising at least a fragment of 10 nucleotides of:

```
SEQ ID 2:
ATGAATTACC AAGTCAATGG TTACCCTAAT ATGTTTATCA

CCCGCGAAGA AGCTATTCGT CACGTTCGTG CGTGGATTGG

CTTTGATGT,

SEQ ID 17:
AGGTTTACCC AATAATACTG CGTCTTGGTT CACAGCTCTC

ACTCAGCATG GCAAGGAGGA ACTTAGATTC CCTCGAGGCC

AGGGCGTTCG AATCAACACC AATAGTGGTC CAGATGACCA

AAT,
```

-continued

```
SEQ ID 26:
CCAAACTGTC ACTAAGAAAT CTGCTGCTGA GGCATCTAAA

AAGCCTCGCC AAAAACGTAC TGCCACAAAA CAGTACAACG

TCACTCAAGC ATTTGGGAGA CGTGGTCCAG AACAAACCCA

AGGAAATT,
or

SEQ ID 34:
TACGATACAT AGTCTACTCT TGTGCAGAAT GAATTCTCGT

AACTAAACAG CACAAGTAGG TTTAGTTAAC TTTAATCTCA

CATAGCAATC TTTAATCAAT GT,
``` or the complementary sequence thereof.

More specifically, the pair of oligonucleotides, according to the above definition, consists essentially of:

a first oligonucleotide comprising, at least a fragment of 10 nucleotides, of a sequence selected from the group consisting of:

```
SEQ ID 3:    TCCACCAGGT GACCAGTTTA AACATCTT,

SEQ ID 4:    TAGTAGCTGT ACCGACTGGT TATGTT,

SEQ ID 5:    TACCTCTCCA GCTAGGATTT TCT,

SEQ ID 15:   TCAGCCCCAG ATGGTACTTC T,

SEQ ID 16:   TAGGAACTGG CCCAGAAGCT TCACTT,

SEQ ID 24:   TGCTCCAAGT GCCTCTGCAT TCTT,

SEQ ID 25:   TTGGCATGGA AGTCACACCT T,

SEQ ID 32:   TGCCTATATG GAAGAGCCC,

SEQ ID 33:   TCCCCATGTG ATTTTAATAG CTT,
``` or the complementary sequence thereof, and a second oligonucleotide comprising, at least a fragment of 10 nucleotides, of a sequence selected from the group consisting of:

```
SEQ ID 6:    ATGAATTACC AAGTCAATGG TTAC,

SED ID 7:    GAAGCTATTC GTCACGTTCG,

SEQ ID 8:    TGCGTGGATT GGCTTTGATG T,

SEQ ID 18:   AGGTTTACCC AATAATACTG CGT,

SEQ ID 19:   AGATTCCCTC GAGGCCAGGG CGT,

SEQ ID 20:   ATAGTGGTCC AGATGACCAA AT,

SEQ ID 27:   CCAAACTGTC ACTAAGAAAT CTGCT,

SED ID 28:   CTCAAGCATT TGGGAGACGT GGT,

SEQ ID 29:   CAGAACAAAC CCAAGGAAAT T,

SEQ ID 35:   TACGATACAT AGTCTACTCT TGT,

SED ID 36:   TAACTAAACA GCACAAGTAG GT,

SEQ ID 37:   TAGCAATCTT TAATCAATGT,
``` or the complementary sequence thereof.

Another aspect of the invention is a pair of oligonucleotides, for use as a set in the amplification of a target sequence located within the replicase gene of the genome of SARS Coronavirus, said pair consisting of:
a first oligonucleotide being 10-50 nucleotides in length and comprising at least a fragment of 10 nucleotides of:

```
SEQ ID 1:
TACCTCTCCA GCTAGGATTT TCTACAGGTG TTAACTTAGT

AGCTGTACCG ACTGGTTATG TTGACACTGA AAATAACACA

GAATTCACCA GAGTTAATGC AAAACCTCCA CCAGGTGACC

AGTTTAAACA TCTT,
``` or the complementary sequence thereof, and
a second oligonucleotide being 10-50 nucleotides in length and comprising at least a fragment of 10 nucleotides of:

```
SEQ ID 2:
ATGAATTACC AAGTCAATGG TTACCCTAAT ATGTTTATCA

CCCGCGAAGA AGCTATTCGT CACGTTCGTG CGTGGATTGG

CTTTGATGT,
``` or the complementary sequence thereof.
More specifically, the pair of oligonucleotides, according to the above definition, consists essentially of:
a first oligonucleotide comprising at least a fragment of 10 nucleotides of a sequence selected from the group consisting of:

```
SEQ ID 3:     TCCACCAGGT GACCAGTTTA AACATCTT,
SEQ ID 4:     TAGTAGCTGT ACCGACTGGT TATGTT,
SEQ ID 5:     TACCTCTCCA GCTAGGATTT TCT,
``` or the complementary sequence thereof, and
a second oligonucleotide comprising at least a fragment of 10 nucleotides of a sequence selected from the group consisting of:

```
SEQ ID 6:     ATGAATTACC AAGTCAATGG TTAC,
SED ID 7:     GAAGCTATTC GTCACGTTCG,
SEQ ID 8:     TGCGTGGATT GGCTTTGATG T,
``` or the complementary sequence thereof.
Another aspect of the invention is a pair of oligonucleotides, for use as a set in the amplification of a target sequence located within the gene encoding the Nucleocapsid protein of the genome of SARS Coronavirus, said pair consisting of:
a first oligonucleotide being 10-50 nucleotides in length and comprising at least a fragment of 10 nucleotides of:

```
SEQ ID 14:
TCAGCCCCAG ATGGTACTTC TATTACCTAG GAACTGGCCC

AGAAGCTTCA CTT,
``` or the complementary sequence thereof, or
a first oligonucleotide being 10-50 nucleotides in length and comprising at least a fragment of 10 nucleotides of:

```
SEQ ID 23:
TGCTCCAAGT GCCTCTGCAT TCTTTGGAAT GTCACGCATT

GGCATGGAAG TCACACCTT,
``` or the complementary sequence thereof, and
a second oligonucleotide being 10-50 nucleotides in length and comprising at least a fragment of 10 nucleotides of:

```
SEQ ID 17:
AGGTTTACCC AATAATACTG CGTCTTGGTT CACAGCTCTC

ACTCAGCATG GCAAGGAGGA ACTTAGATTC CCTCGAGGCC

AGGGCGTTCC AATCAACACC AATAGTGGTC CAGATGACCA

AAT,
``` or the complementary sequence thereof or,
a second oligonucleotide being 10-50 nucleotides in length and comprising at least a fragment of 10 nucleotides of:

```
SEQ ID 26:
CCAAACTGTC ACTAAGAAAT CTGCTGCTGA GGCATCTAAA

AAGCCTCGCC AAAAACGTAC TGCCACAAAA CAGTACAACG

TCACTCAAGC ATTTGGGAGA CGTGGTCCAG AACAAACCCA

AGGAAATT,
``` or the complementary sequence thereof.
More specifically, the pair of oligonucleotides, according to the above definition, consists essentially of:
a first oligonucleotide comprising at least a fragment of 10 nucleotides of a sequence selected from the group consisting of:

```
SEQ ID 15:    TCAGCCCGAG ATGGTACTTC T,
SEQ ID 16:    TAGGAACTGG CCCAGAAGCT TCACTT,
SEQ ID 24:    TGCTCCAA GTGCCTCTGC ATTCTT,
SEQ ID 25:    TTGGCATGGA AGTCACACCT T,
``` or the complementary sequence thereof, and
a second oligonucleotide comprising at least a fragment of 10 nucleotides of a sequence selected from the group consisting of:

```
SEQ ID 18:    AGGTTTACCC AATAATACTG CGT,
SED ID 19:    AGATTCCGTC GAGGCCAGGG CGT,
SEQ ID 20:    ATAGTGGTCC AGATGACCAA AT,
SEQ ID 27:    CCAAACTGTC ACTAAGAAAT CTGCT,
SED ID 28:    CTCAAGCATT TGGGAGACGT GGT,
SEQ ID 29:    CAGAACAAA.C CCAAGGAAAT T,
``` or the complementary sequence thereof.
Another aspect of the invention is a pair of oligonucleotides, for use as a set in the amplification of a target sequence located within the 3'-Non Coding Region (3'-NCR) of the genome of SARS Coronavirus, said pair consisting of:
a first oligonucleotide being 10-50 nucleotides in length and comprising at least a fragment of 10 nucleotides of:

```
SEQ ID 31:
TGCCTATATG GAAGAGCCCT AATGTGTAAA ATTAATTTTA

GTAGTGCTAT CCCCATGTGA TTTTAATAGC TT,
``` or the complementary sequence thereof, and a second oligonucleotide being 10-50 nucleotides in length and comprising at least a fragment of 10 nucleotides of:

```
SEQ ID 34:
TACGATACAT AGTCTACTCT TGTGCAGAAT GAATTCTCGT

AACTAAACAG CACAAGTAGG TTTAGTTAAC TTTAATCTCA

CATAGCAATC TTTAATCAAT GT,
``` or the complementary sequence thereof.

More specifically, the pair of oligonucleotides, according to the above definition, consists essentially of:

a first oligonucleotide comprising at least a fragment of 10 nucleotides of a sequence selected from the group consisting of:

```
SEQ ID 32: TGCCTATATG GAAGAGCCC,

SEQ ID 33: TCCCCATGTG ATTTTAATAG CTT,
``` or the complementary sequence thereof, and a second oligonucleotide comprising at least a fragment of 10 nucleotides of a sequence selected from the group consisting of:

```
SEQ ID 35: TACGATACAT AGTCTACTCT TGT,

SED ID 36: TAACTAAACA GCACAAGTAG GT,

SEQ ID 37: TAGCAATCTT TAATCAATGT,
``` or the complementary sequence thereof.

The oligonucleotide pair, according to any of the above definitions, may be constituted by a first oligonucleotide provided with a promoter sequence recognized by a DNA dependent RNA polymerase.

For instance, the sequences SEQ ID 9-11 and SEQ ID 39-44 actually comprise the complementary and reverse sequence as reflected by SEQ ID 3-5 and SEQ ID 15, 16, 24, 25, 32 and 33 respectively. In SEQ ID 9-11 and SEQ ID 39-44, the complementary and reverse sequences of SEQ ID 3-5 and SEQ ID 15, 16, 24, 25, 32 and 33 are operably linked to a promoter sequence (the T7 promoter sequence). This makes the sequences especially suitable for use as downstream primer in a transcription based amplification technique such as NASBA.

One of the oligonucleotides may serve as an "upstream oligonucleotide", i.e., an upstream-primer, while the second oligonucleotide serves as a "downstream oligonucleotide", i.e. downstream primer, in the amplification reaction. The location on the SARS-genome (or the sequence complementary thereto) to which both oligonucleotides comprised in such a pair according to the invention can anneal, will together define the sequence of the nucleic acid that is amplified. The amplified sequence is located between the "primer-binding sites" within the SARS genome. It has been found that, by using a pair of oligonucleotides according to the invention in an amplification reaction, accurate and reliable amplification of nucleic acid of SARS can be achieved.

A preferred pair of oligonucleotides according to the invention in the SARS-CoV REP consist of a first primer comprising the sequence of SEQ ID NO 4 or 10 and a second primer with the sequence of SEQ ID NO 7, or of a second set composed by a first primer comprising the sequence of SEQ ID NO 10 and by a second primer with the sequence of SEQ ID NO 8, or of a third set composed by a first primer comprising the sequence of SEQ ID NO 9 and by a second primer with the sequence of SEQ ID NO 8. For use in a transcription based amplification method, especially the NASBA amplification, the oligonucleotide with SEQ ID NO 10 is preferred, in combination with an oligonucleotide with the sequence of SEQ ID NO 7.

A most preferred pair of oligonucleotides according to the invention in the SARS-CoV N:

in a first part of the nucleic acid sequence, hereafter called region 1, consists of a first primer comprising the sequence of SEQ ID NO 15 and a second primer with the sequence of SEQ ID NO 19, and in a second part of the nucleic acid sequence, hereafter called region 2, consists of either

- a first primer comprising the sequence of SEQ ID NO 41 and a second primer with the sequence of SEQ ID NO 28, or
- a first primer comprising the sequence of SEQ ID NO 42 and a second primer with the sequence of SEQ ID NO 28, or
- a first primer comprising the sequence of SEQ ID NO 42 and a second primer with the sequence of SEQ ID NO 29.

A most preferred pair of oligonucleotides according to the invention in the SARS-CoV 3'-NCR consist of a first set composed by a first primer comprising the sequence of SEQ ID No 32 and by a second primer with the sequence of SEQ ID NO 35 and a second set composed by a first primer comprising the sequence of SEQ ID NO 33 and by a second primer with the sequence of SEQ ID NO 36.

Part of the oligonucleotides according to the invention are particularly suitable for use as a probe in the detection of nucleic acid amplified with a pair of oligonucleotides according to the invention. When used as a probe, said oligonucleotides may be provided with a detectable label.

Oligonucleotides according to the invention that are especially suitable as a probe consist of sequences of 10-50 nucleotides in length and comprising at least a fragment of 10 nucleotides of:

```
SEQ ID 12:
GTTCGTGCGT GGATTGGCTT TGATGTAGAG GGCTGTCATG

CAACTAGAGA TGCTGT,

SEQ ID 21:
GGCTACTACC GAAGAGCTAC CCGACGAGTT CGTGGTGGTG

ACGGCAAAAT GAAAGAGCTC AGCCCCAGAT GGTACTTCTA

TTACCTAGGA ACTGGCCCAG AAGCTTCACT TCCCTACGGC

GCTAACAAAG AAGGCATCGT ATGGGTTGCA ACTGAGGGAG

CCTTGAATAC ACCCAAAGAC CACATTGGCA CCCGCAATCC

TAATAACAAT GCTGCCACCG TGCTACAACT TCCTCAAGGA

ACAACATTGC CAAAAGGCTT CTACGCAGAG GGAAGCAGAG

GCGGCAGTCA AGCCTCTTCT CGCTCCTCAT CACGTAGTCG

CGGTAATTCA AGAAATTCAA CTCCTGGCAG CAGTAGGGGA

AATTCTCCTG CTCGAATGGC TAGCGGAGGT GGTGAAACTG

CCCTCGCGCT ATTGCTGCTA GACAGATTGA ACCAGCTTGA

GAGCAAAGTT TCTGGTAAAG GCCAACAACA ACAAGGCCAA

ACTGTCACTA AGAAATCTGC TGCTGAGGCA TCTAAAAAGC
```

```
-continued
CTCGCCAAAA ACGTACTGCC ACAAAACAGT ACAACGTCAC

TCAAGCATTT GGGAGACGTG GTCCAGAACA AACCCAAGGA

AATTTCGGGG ACCAAGACCT AATCAGACAA,

SEQ ID 38:
    GCCACCACAT TTTCATCGAG GC,
``` or the complementary sequence thereof, provided with a detectable label.

A molecular beacon, preferably consisting of, constitutes the probe:

```
SEQ ID 13:
5'-[6-FAM]-ccatgggCTGTCATGCAACTAGAGATGCTGTcccatgg-

[DabSyl]-3',

SEQ ID 45:
5'-[6-FAM]-cgcgatGTTCGTGCGTGGATTGGCTTatcgcg-

[DabCyl]-3',

SEQ ID 22:
5'-[6-FAM]-ccatgggCTACTACCGAAGAGCTACCCGACGAcccatg g-[DabSyl]-3',

SEQ ID 30:
5'-[6-FAM]-ccatggACCAAGACCTAATCAGACAAccatgg-

[DabSyl]-3',

SEQ ID 47:
5'-[6-FAM]-ccatgcGCCACCACATTTTCATCGAgcatgg-

[DabSyl]-3'
```

Various labeling moieties are known in the art. Said moiety may, for example, either be a radioactive compound, a detectable enzyme (e.g. horse radish peroxidase (HRP)), a hapten like biotin, or any other moiety capable of generating a detectable signal such as a colorimetric, fluorescent, chemiluminescent or electrochemiluminescent signal.

Hybrids between oligonucleotides according to the invention and (amplified) target nucleic acid may also be detected by other methods known to those skilled in the art. Evidently methods for amplification of nucleic acid, like the ones that have been mentioned above, using the oligonucleotides according to the present invention are also part of the invention.

The sequence in capital letters refers to the probe itself according to SEQ ID 14 for instance, i.e. where the hybridisation between said probe and a part of the amplified nucleic acid takes place. Downstream and upstream extensions, in small letters, are sequences called here 7-nucleotide-long arm sequences that are able to hybridise one to the other. These arm sequences relate to linkers between the probe and on the one hand a fluorophore (6-FAM) and on the other hand quencher 4-(4'-dimethylaminophenylazo) benzoic acid (DabCyl or DabSyl). An ideal fluorophore-quencher pair is completely unable to fluoresce when the two components are in close proximity, but as soon as the loop of the molecular beacon is conformationally changed due to hybridization of the probe to the amplified nucleic acid, the distance between the fluorophore and the quencher is sufficiently enlarged to permit emission of fluorescence.

Other fluorescent reporters are possible like 5' fluorescein, 5' TET, 5' HEX, 5' FAM, 5' TAMRA, 5' ROX, 5' Texas Red, 5' Oregon Green, 5' Cy3 or 5' Cy5. In the same way other quenchers, such as 3' Black Hole Quencher-1 or 3' Black Hole Quencher-2, can be used.

In another aspect of the invention, an oligonucleotides' pair, according to the ones here above disclosed, is used in a nucleic acid amplification reaction or as a probe for the detection of SARS Coronavirus nucleic acid in a sample. Consequently it is possible to perform a method for the detection of SARS nucleic acid in a sample wherein the sample is subjected to a nucleic acid amplification reaction using a pair of oligonucleotides above disclosed and suitable amplification reagents and the presence of any amplified nucleic acid is detected. This method, wherein reacting the sample with an oligonucleotide under suitable hybridization conditions and detecting the presence of the label in any hybrids could carry out the detection of any amplified nucleic acid, formed between the amplified sequence and the probe. Preferably the amplification technique used is a transcription based amplification technique, more preferably the NASBA, and the first oligonucleotide is provided with a promoter sequence recognized by a DNA dependent RNA polymerase.

The present invention further provides test kits for the amplification and detection of SARS nucleic acid. The use of said test kits enables accurate and sensitive screening of samples suspected of containing SARS derived nucleic acid. Such test kits may contain a pair of oligonucleotides according to the invention and optionally also an oligonucleotide according to the invention that can be used as a probe for the detection of the amplified material. Furthermore the test kit may contain suitable amplification reagents. These reagents are for example the suitable enzymes for carrying out the amplification reaction. A kit, adapted for use with NASBA, for example may contain suitable amounts of reverse transcriptase, RNase H and T7 RNA polymerase. Said enzymes may be present in the kit in a buffered solution but can likewise be provided as a lyophilized composition, for example, a lyophilized spherical particle. Such lyophilized particles have been disclosed in PCT/EP95/01268. The kit may further be furnished with buffer compositions, suitable for carrying out an amplification reaction. Said buffers may be optimized for the particular amplification technique for which the kit is intended as well as for use with the particular oligonucleotides that are provided with the kit. In transcription-based amplification techniques, such as NASBA, said buffers might contain, for example, DMSO, which enhances the amplification reaction (as is disclosed in PCT/US90/04733).

Furthermore the kit may be provided with an internal control as a check on the amplification procedure and to prevent the occurrence of false negative test results due to failures in the amplification procedure. The use of internal controls in transcription based amplification techniques is described in PCT/EP93/02248. An optimal control sequence is selected in such a way that it will not compete with the target nucleic acid in the amplification reaction. Kits may also contain reagents for the isolation of nucleic acid from biological specimens prior to amplification. A suitable method for the isolation of nucleic acid is disclosed in EP-A-0.389.063.

Virus Propagation and Isolation from In-Vitro Cultures:

A variety of clinical specimens (blood, serum, material from oropharyngeal swabs or washings, material from nasopharyngeal swabs, and tissues of major organs collected at autopsy) were inoculated onto a number of continuous cell lines, including Vero E6, NCIH292, MDCK, LLC-MK2 and B95-8 cells. Two cell lines, Vero E6 cells and NCI-H292 cells, inoculated with oropharyngeal specimens from patients with SARS initially showed cytopathic effect. A rhinovirus was isolated from the inoculated NCI-H292 cells, but further study suggested that this virus was not associated with patients with SARS. Examination of cytopathic-effect-positive VeroE6 cells by thin-section electron microscopy revealed characteristic coronavirus particles within the cisternae of the rough endoplasmic reticulum and in vesicles. Extracellular particles were found in large clusters and adhering to the surface of the plasma membrane. Vero E6 cells have now become the standard cell line for the isolation and propagation of the SARS related human Coronavirus (Marra et al. (1), Drosten et al. (10), Ksiazek et al. (13)).

Identification of Specific Nucleic Acid Fragments of the SARS Related Human Coronavirus:

This identification has already been disclosed previously in the disclosure according to a publication (Drosten et al. (10)). A group at the National Microbiology Laboratory in Canada also obtained a SARS genomic sequence (Genbank Accession AY274119.3) from an isolate referred to as Tor2. The latter sequence is essentially identical to the one that was released independently by the CDC (GenBank accession number AY278741). Additional bases in the Tor2 sequence that correspond to the 3' (encoded) polyA tail were reported. Eight base differences between the two sequences could represent sequencing errors, PCR artefacts or mutable sites in the genome. (Marra et al. (6)). The genome of SARS-Coronavirus is a 29,727-nucleotides polyadenylated RNA, and 41% of the residues are G or C The genomic organization is typical of coronaviruses, with the characteristic gene order. The SARS-Coronavirus replicase gene, which comprises approximately two-thirds of the genome, is predicted to encode two polyproteins (encoded by ORF1a and ORF1b) that undergo co-translational proteolytic processing. There are four open reading frames (ORFs) downstream of replicase that are predicted to encode the structural proteins S, E, M, and N, which are common to all known coronaviruses. The hemagglutinin-esterase (HE) gene, which is present between ORF1b and S in group 2 and some group 3 coronaviruses, was not found. (Rota et al. (7)). This is in agreement with the Electron microscopic observations of virus particles lacking the HE surface projections.

Phylogenetic analyses of the sequence of SARS-Coronavirus indicate that SARS-Coronavirus is not closely related to any of the previously characterized coronaviruses and forms a distinct group within the genus Coronavirus. The SARS-Coronavirus is approximately equidistant from all previously characterized coronaviruses, just as the existing groups are from one another. No evidence for recombination was detected when the predicted protein sequences were analyzed using SimPlot in comparison to sequences of known Coronaviruses.

The coronavirus subgenomic mRNAs are synthesized through a discontinuous transcription process, the mechanism of which has not been unequivocally established. The favoured model for production of subgenomic mRNAs of coronaviruses proposes that discontinuous transcription occurs during synthesis of the negative strand (Sawicki G. S. et al. (14)). The positions of the transcription regulating sequences (TRS) in the genome of SARS-Coronavirus predict that subgenomic mRNAs of 8.3, 4.5, 3.4, 2.5, 2.0, and 1.7 kb, not including the poly(A) tail, should be produced.

At least five subgenomic mRNAs were indeed detected by Northern hybridization of RNA from SARS-Coronavirus-infected cells, using a probe derived from the 3'-untranslated region. Full-length genomic RNA was not detected, likely because it is the least prevalent viral RNA in infected cells (Lai et al. (15)). The predicted 2.0 kb transcript was also not detected, suggesting that the consensus TRS at nucleotides 27,771-27,778 is not used or that it is a low-abundance mRNA (Rota et al. (2)).

The invention will further illustrated by the following non-limiting Examples, with reference to the accompanying Figures, in which:

FIGS. 1-4 show amplification curves of 4 different primer pairs ((FIG. 1) SARS-CoV REP P1.1/P2.1, (FIG. 2) SARS-CoV REP P1.1/P2.2, (FIG. 3) SARS-CoV REP P1.2/P2.1 and (FIG. 4) SARS-CoV REP P1.2/P2.2) tested on a dilution series of SARS Coronavirus in vitro REP RNA.

FIG. 5 shows amplification curves of the selected primer pair (P1.1/P2.2), testing the analytical sensitivity of the SARS CoV NASBA.

FIG. 6 shows the predicted secondary structures for SARS-CoV REP MB-1 and SARS-CoV REP MB-2.

FIGS. 7-11 show amplification curves of 5 other different primer pairs ((FIG. 7) SARS-CoV REP P1.1/P2.3, (FIG. 8) SARS-CoV REP P1.2/P2.3, (FIG. 9) SARS-CoV REP P1.3/P2.1, (FIG. 10) SARS-CoV REP P1.3/P2.2 and (FIG. 11) SARS-CoV REP P1.3/P2.3) tested on a dilution series of SARS Coronavirus RNA.

FIG. 12 show the predicted secondary structures for SARS-CoV N MB-1 and SARS-CoV N MB-2.

FIGS. 13-16 show real-time amplification of SARS-CoV viral RNA with SARS-CoV N primer/beacon mixtures in region 1. Four SARS-CoV N primer pairs (Table 7) were combined with molecular beacon SARS-CoV N MB-1 (Table 6) for the amplification and real-time detection of SARS-CoV RNA extracted from a dilution series of cultured SARS-CoV. (FIG. 13) SARS-CoV N P1.1/P2.1; (FIG. 14) SARS-CoV N P1.1/P2.2; (FIG. 15) SARS-CoV N P1.2/P2.1; (FIG. 16) SARS-CoV N P1.2/P2.2.

FIGS. 17-20 show real-time amplification of SARS-CoV viral RNA with SARS-CoV N primer/beacon mixtures in region 1. Four SARS-CoV N primer pairs (Table 7) were combined with molecular beacon SARS-CoV N MB-1 (Table 6) for the amplification and real-time detection of SARS-CoV RNA extracted from a dilution series of cultured SARS-CoV upon storage of the nucleic acid extracts prior to amplification. (FIG. 17) SARS-CoV N P1.1/P2.1; (FIG. 18) SARS-CoV N P1.1/P2.2; (FIG. 19) SARS-CoV N P1.2/P2.1; (FIG. 20) SARS-CoV N P1.2/P2.2.

FIGS. 21-24 show real-time amplification of SARS-CoV viral RNA with SARS-CoV N primer/beacon mixtures in region 2. Four SARS-CoV N primer pairs (Table 7) were combined with molecular beacon SARS-CoV N MB-2 (Table 6) for the amplification and real-time detection of SARS-CoV RNA extracted from a dilution series of cultured SARS-CoV. (FIG. 21) SARS-CoV N P1.3/P2.3; (FIG. 22) SARS-CoV N P1.3/P2.4; (FIG. 23) SARS-CoV N P1.4/P2.3; (FIG. 24) SARS-CoV N P1.4/P2.4.

FIGS. 25-28 show real-time amplification of SARS-CoV viral RNA with SARS-CoV N primer/beacon mixtures in region 2. Four SARS-CoV N primer pairs (Table 6) were combined with molecular beacon SARS-CoV N MB-2 (Table 5) for the amplification and real-time detection of SARS-CoV RNA extracted from a dilution series of cultured SARS-CoV upon storage of the nucleic acid extracts prior to amplification. (FIG. 25) SARS-CoV N P1.3/P2.3; (FIG. 26) SARS-CoV N P1.3/P2.4; (FIG. 27) SARS-CoV N P1.4/P2.3; (FIG. 28) SARS-CoV N P1.4/P2.4.

FIGS. 29-34 show real-time amplification of SARS-CoV viral RNA with SARS-CoV N primer/beacon mixtures in region 1. Six SARS-CoV N primer pairs (Table 7) were combined with molecular beacon SARS-CoV N MB-1 (Table 6) for the amplification and real-time detection of SARS-CoV RNA extracted from a dilution series of cultured SARS-CoV. (FIG. 29) SARS-CoV N P1.1/P2.1; (FIG. 30) SARS-CoV N P1.1/P2.2; (FIG. 31) SARS-CoV N P1.1/P2.5; (FIG. 32)

SARS-CoV N P1.2/P2.1; (FIG. 33) SARS-CoV N P1.2/P2.2; (FIG. 34) SARS-CoV N P1.2/P2.5.

FIGS. 35-40 show real-time amplification of SARS-CoV viral RNA with SARS-CoV N primer/beacon mixtures in region 2. Six SARS-CoV N primer pairs (Table 7) were combined with molecular beacon SARS-CoV N MB-2 (Table 6) for the amplification and real-time detection of SARS-CoV RNA extracted from a dilution series of cultured SARS-CoV. (FIG. 35) SARS-CoV N P1.3/P2.3; (FIG. 36) SARS-CoV N P1.3/P2.4; (FIG. 37) SARS-CoV N P1.3/P2.6; (FIG. 38) SARS-CoV N P1.4/P2.3; (FIG. 39) SARS-CoV N P1.4/P2.4; (FIG. 40) SARS-CoV N P1.4/P2.6.

FIG. 41 show predicted secondary structures for the SARS-CoV 3'-NCR molecular beacon.

FIG. 42-47 show real-time amplification of SARS-CoV viral RNA with SARS-CoV 3'-NCR primer/beacon mixtures. Six SARS-CoV 3'-NCR primer pairs (Table 9) were combined with molecular beacon SARS-CoV 3'-NCR MB-1 (Table 10) for the amplification and real-time detection of SARS-CoV RNA extracted from a dilution series of cultured SARS-CoV. (FIG. 42) SARS-CoV 3'-NCR P1.5/P2.5; (FIG. 43) SARS-CoV 3'-NCR P1.5/P2.6; (FIG. 44) SARS-CoV 3'-NCR P1.5/P2.7; (FIG. 45) SARS-CoV 3'-NCR P1.6/P2.5; (FIG. 46) SARS-CoV 3'-NCR P1.6/P2.6; (FIG. 47) SARS-CoV 3'-NCR P1.6/P2.7.

(FIG. 48) SARS-CoV REP-1; (FIG. 49) SARS-CoV REP-2; (FIG. 50) SARS-CoV N-1; (FIG. 51) SARS-CoV 3'-NCR.

(FIG. 52) SARS-CoV REP-1; (FIG. 53) SARS-CoV REP-2; (FIG. 54) SARS-CoV N-1; (FIG. 55) SARS-CoV 3'-NCR.

(FIG. 56) SARS-CoV REP-1; (FIG. 57) SARS-CoV REP-2; (FIG. 58) SARS-CoV N-1; (FIG. 59) SARS-CoV N-2; (FIG. 60) SARS-CoV 3'-NCR.

EXAMPLES

First Set of Examples Related to RNA Issued from the Viral Replicase Gene

Example 1

Materials and Methods

1. SARS CoV In Vitro RNA:

RNA encompassing 190 nucleotides of the SARS CoV replicase gene was synthesized in vitro by transcription of a cloned fragment of the viral gene, essentially as described in Drosten et al. (10). The concentration of the in vitro generated RNA was determined by OD (260 nm) measurement and appropriate serial dilutions in water were stored at −70° C. until further use.

2. Oligonucleotides Used for Amplification and Detection:

Primers and a molecular beacon detection probes (Tyagi, S. and Kramer, F. R. (16)) were derived from the sequence of the open reading frame (ORF) 1b of the SARS CoV replicase gene and ordered as HPLC-purified oligonucleotides (Eurogentec, Belgium). Sequence numbers and genome locations of the oligonucleotides used in the amplification and of the molecular beacon probe used for specific detection in real-time, are shown in Table 1.

TABLE 1

Primers and molecular beacon probes for the amplification and detection in real-time of a region located in the replicase gene of SARS Coronavirus.

| Primer/probe name | Sequence number | Primer/probe | Location |
|---|---|---|---|
| SARS-CoV REP P1.1 | SEQ ID 10 | Downstream primer 1.1 | 18319-18344 |
| SARS-CoV REP P1.2 | SEQ ID 11 | Downstream primer 1.2 | 18283-18305 |
| SARS-CoV REP P1.3 | SEQ ID 9 | Downstream primer 1.3 | 18389-18416 |
| SARS-CoV REP P2.1 | SEQ ID 6 | Upstream primer 2.1 | 18153-18176 |
| SARS-CoV REP P2.2 | SEQ ID 7 | Upstream primer 2.2 | 18201-18220 |
| SARS-CoV REP P2.3 | SEQ ID 8 | Upstream primer 2.3 | 18221-18241 |
| SARS-CoV REP MB-1 | Label + SEQ ID 13 + quencher | Probe MB-1 | 18246-18271 |
| SARS-CoV REP MB-2 | Label + SEQ ID 45 + quencher | Probe MB-2 | 18216-18235 |

Figure 6A:
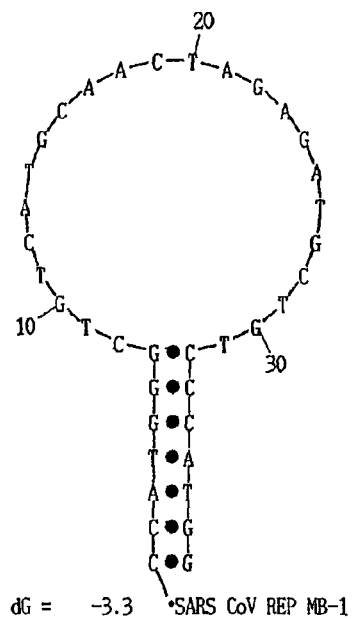
Figure 7:
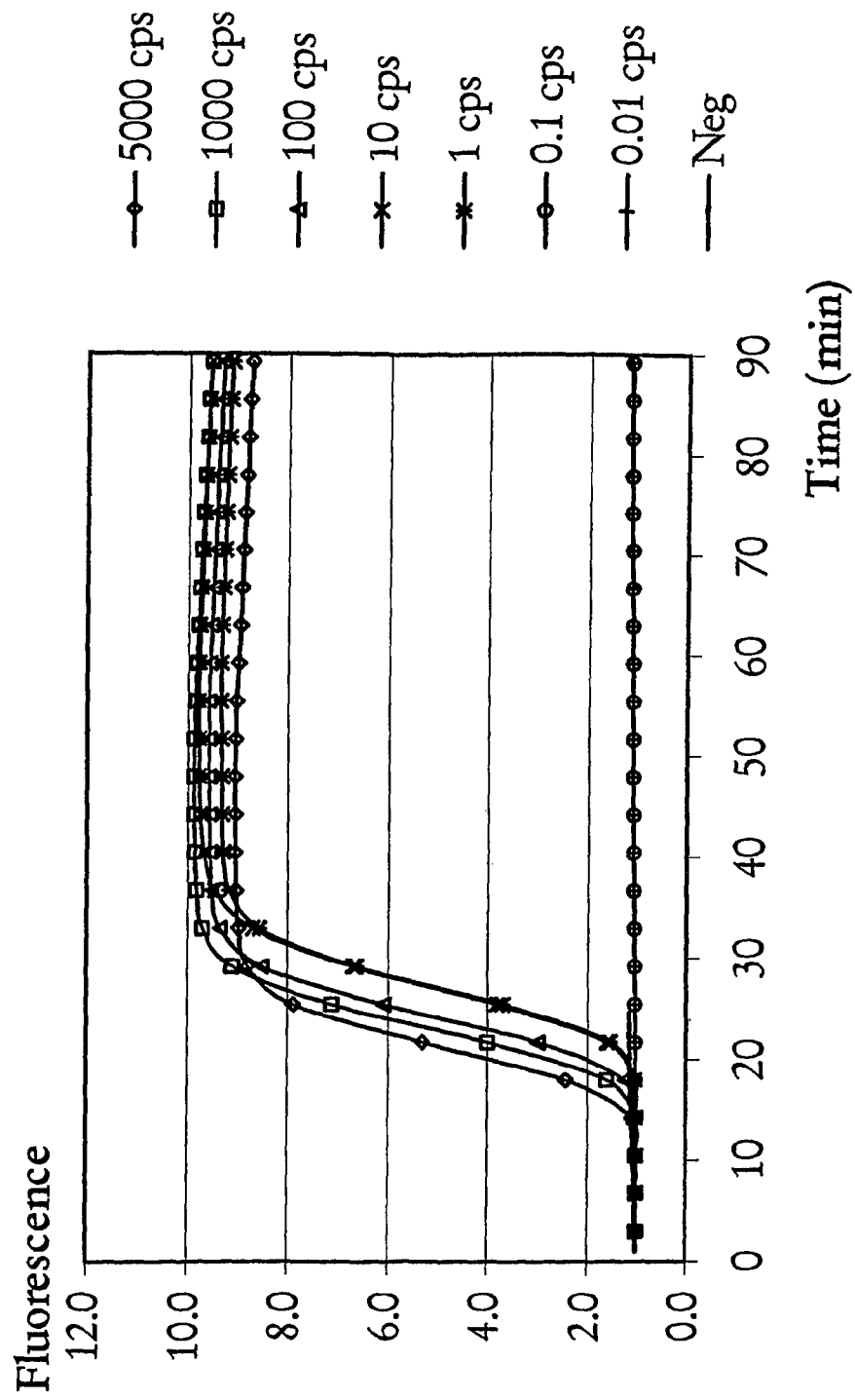
Figure 8:
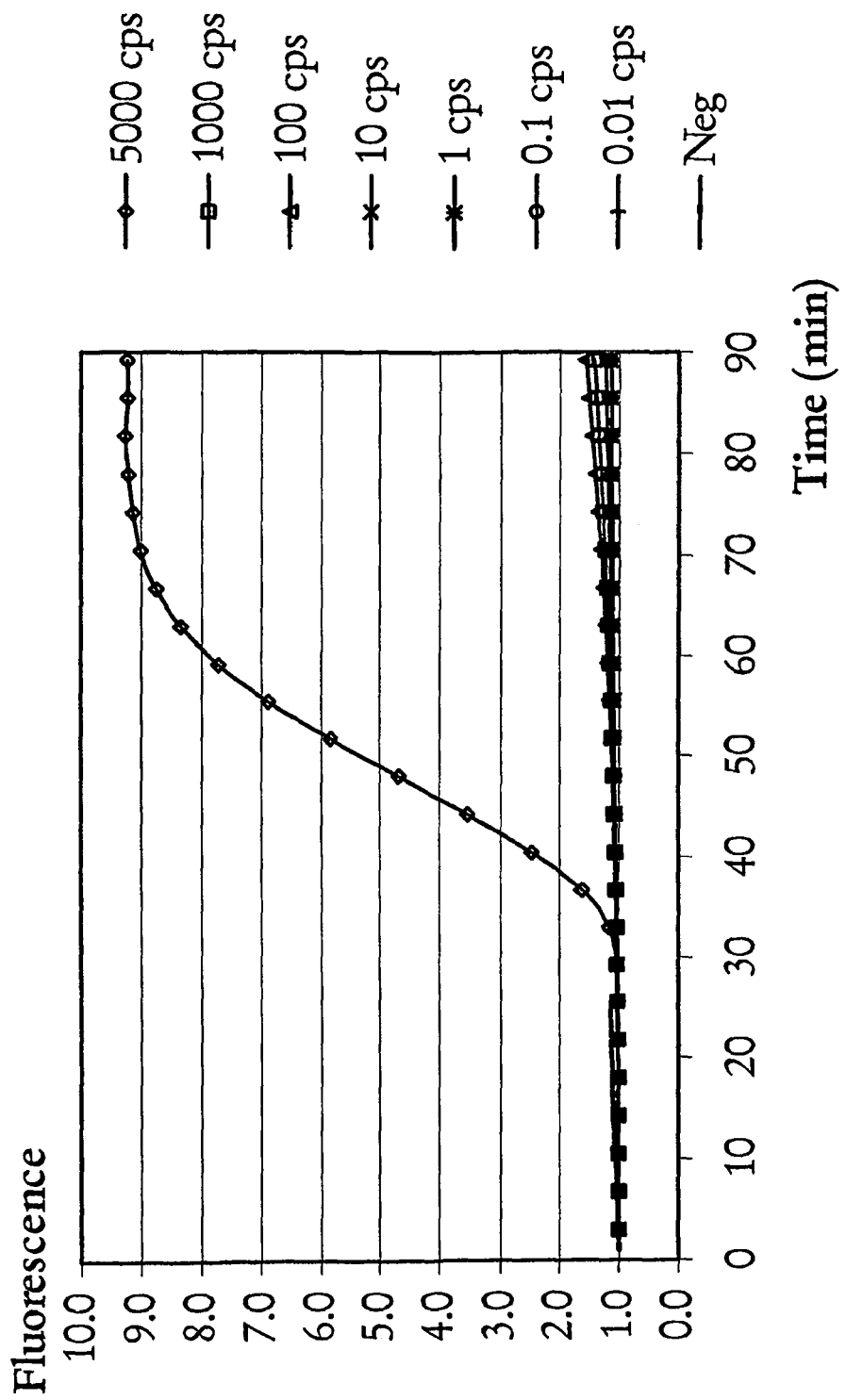
Figure 9:
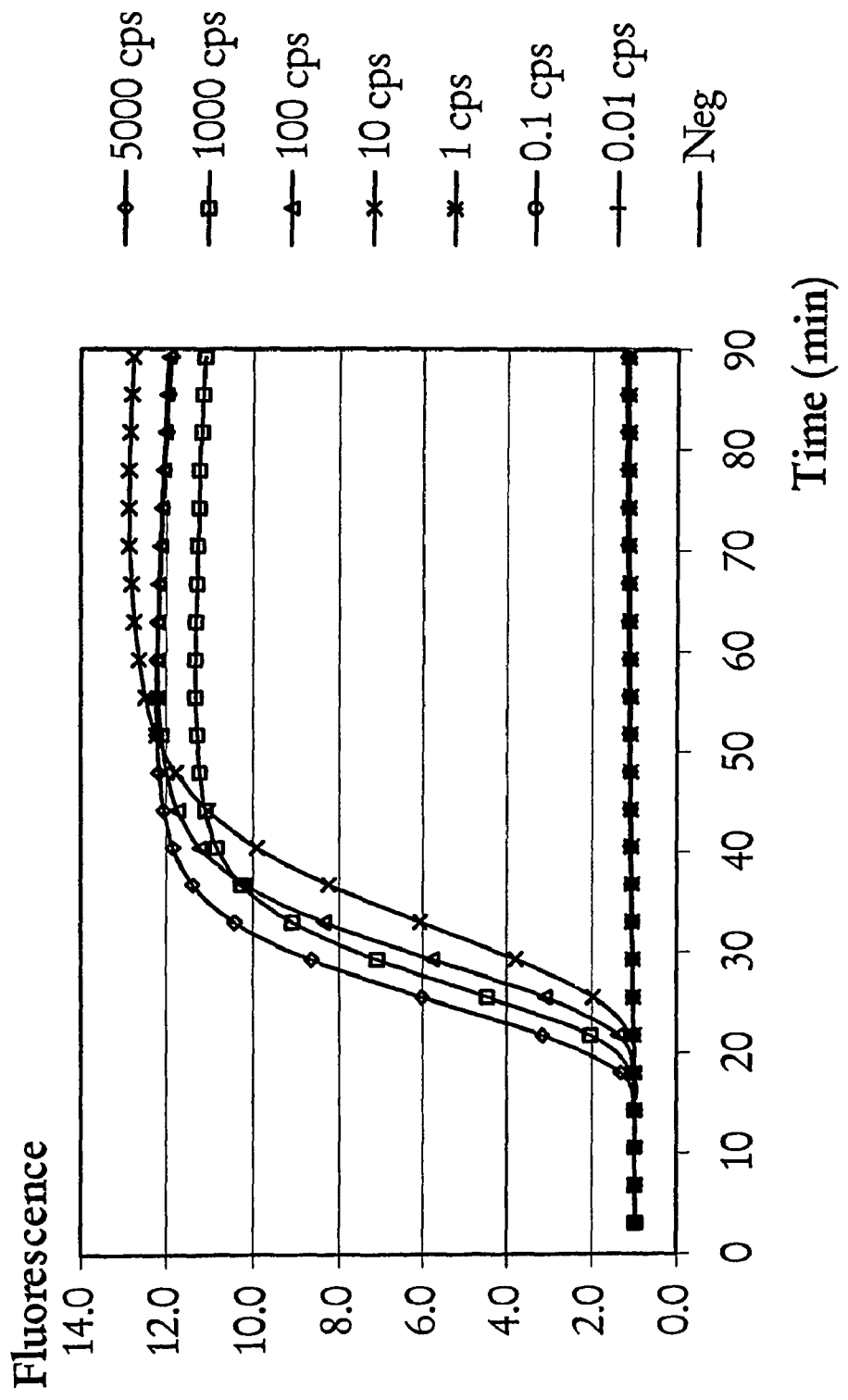
Figure 10:
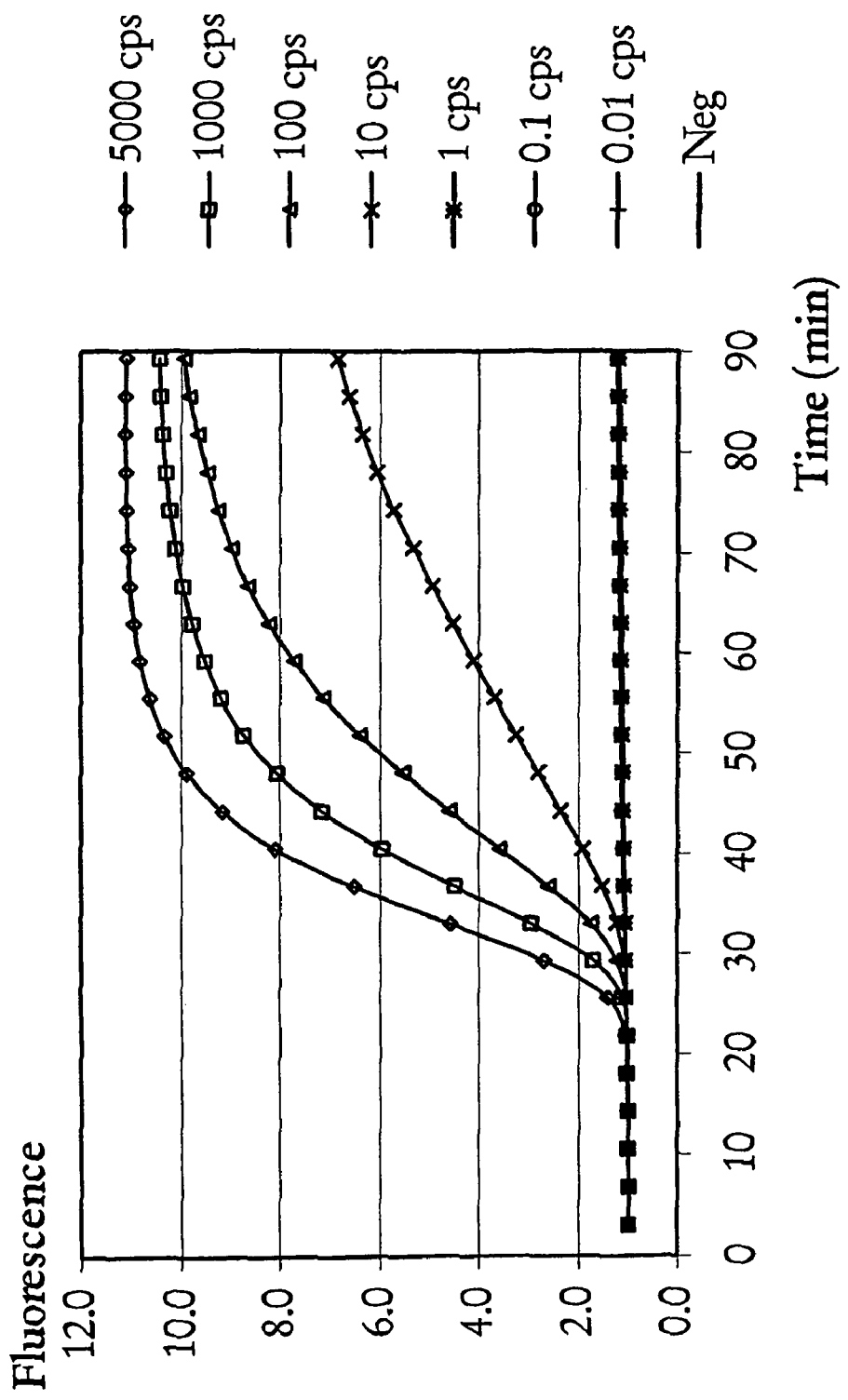
Figure 11:
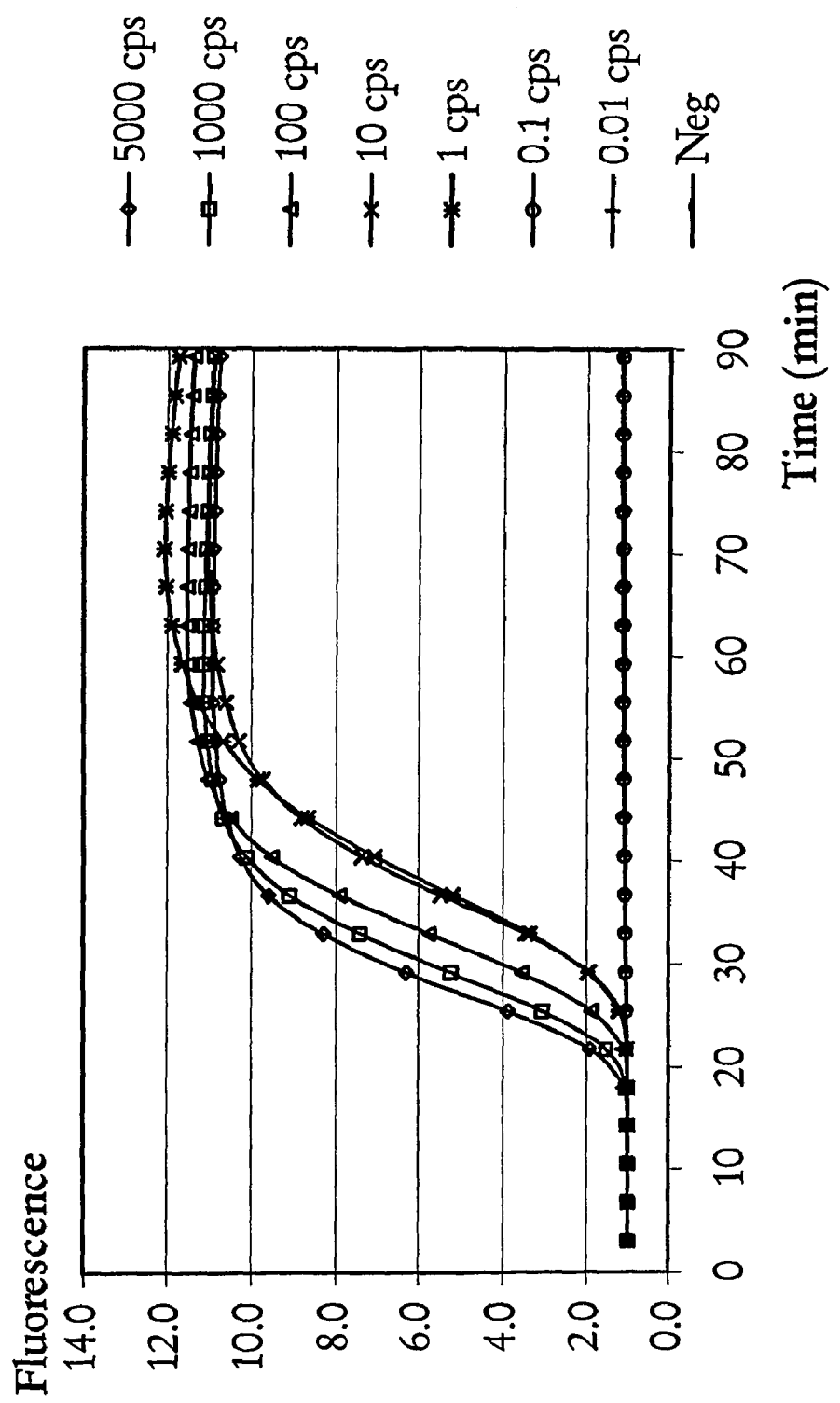

The two molecular beacons (SARS CoV MB-1 and MB-2) were designed for the detection of the amplicons that can be generated with the SARS-CoV REP primers outlined in Table 1. Correct folding of the molecular beacons was checked using mfold (17) web server (http://www.bioinfo.rpi.edu/applications/mfold). Predicted secondary structures for SARS-CoV REP MB-1 and SARS-CoV REP MB-2 are shown in FIG. 6. Under NASBA reaction conditions, i.e. 41° C.; 100 mM Na$^+$; 12 mM Mg$^{2+}$, both molecular beacons revealed the desired hairpin structure as the most favourable conformation. For SARS-CoV REP MB-1, additional hybrid formation was predicted within the loop portion, resulting in two other possible conformations.

Molecular beacon syntheses were analysed for their purity by capillary electrophoresis (CE). Molecular beacons have a purity varying between 80.3% for SARS-CoV REP MB-2 and 88.7% for SARS-CoV REP MB-1.

In FIG. 6, the arm sequences at the 5'-end and at the 3'-end are hybridized and here below depicted in small characters. Thus each probe is constituted as a molecular beacon, preferably consisting of:

```
SEQ ID 13:
5'-[6-FAM]-ccatgggCTGTCATGCAACTAGAGATGCTGTcccatgg-
[DabSyl]-3',
or SEQ ID 45:
5'-[6-FAM]-cgcgatGTTCGTGCGTGGATTGGCTTatcgcg-
[DabCyl]-3'.
```

Fluorophore 6-FAM is covalently linked to the 5'-end of the molecular beacon; the quenching moiety DabSyl or Dab-Cyl is covalently linked to the 3'-end of the molecular beacon. Coordinates for the location of the hybridising segments of the primers and the molecular beacon probe are derived from the complete genome sequence of SARS coronavirus TOR2 (EMBL Accession number AY274119).

3. NASBA Amplification with Real-Time Detection:

RNA amplifications were performed using the NASBA amplification technology. To set up a NASBA amplification reaction, NucliSens Basic Kit Amplification Reagents (bioMérieux bv, The Netherlands) were used. A premix was generated by reconstituting a Reagent Sphere in a mixture of 80 μl Reagent Sphere Diluent, 18 μl KCl stock solution and 12 μl NASBA Water. Subsequently, 10 μl of a mix containing two primers for amplification and a molecular beacon probe for real-time detection, were added, resulting in 2× reaction buffer. Ten μl of this reaction buffer was added to 5 μl nucleic acid solution and incubated during 5 minutes at 65° C. Then the reaction tubes were incubated at 41° C. during 5 minutes. Meanwhile, an Enzyme Sphere was reconstituted in 55 μl Enzyme Diluent and 5 μl of the resulting enzyme mix was added into each reaction tube. After addition of the enzyme mix, tubes were mixed by gentle tapping, centrifuged briefly to bring the contents to the bottom of the tubes and finally incubated at 41° C. during 90 minutes in a NucliSens EasyQ Analyzer. Fluorescence in the individual reaction tubes was monitored over time and measured at regular intervals of 45 seconds.

Example 2

Selection of Primer Pair for the Amplification of SARS CoV RNA

To select a well performing primer pair for the amplification of SARS CoV RNA using NASBA, three upstream primers, designated P2.1, P2.2 and P2.3, and three downstream primers, designated P1.1, P1.2 and P1.3, were derived from the sequence of the open reading frame (ORF) 1b of the SARS CoV replicase gene. Consequently, nine different primer pairs could be formed, each consisting of a combination of one of the upstream primers with one of the downstream primers. With each of these primer pairs a standard dilution series of in vitro generated SARS CoV RNA was evaluated.

Figure 1:
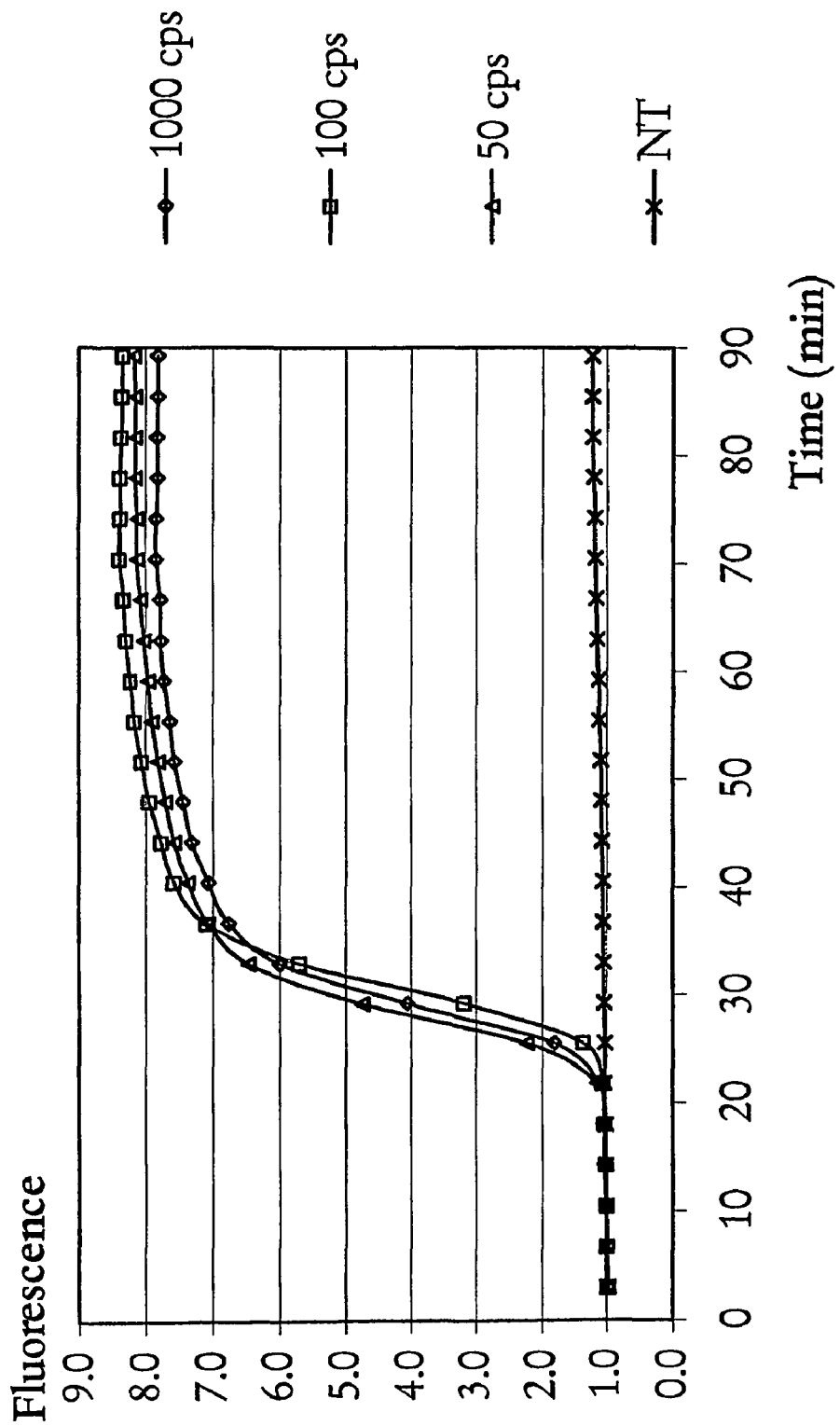
Figure 2:
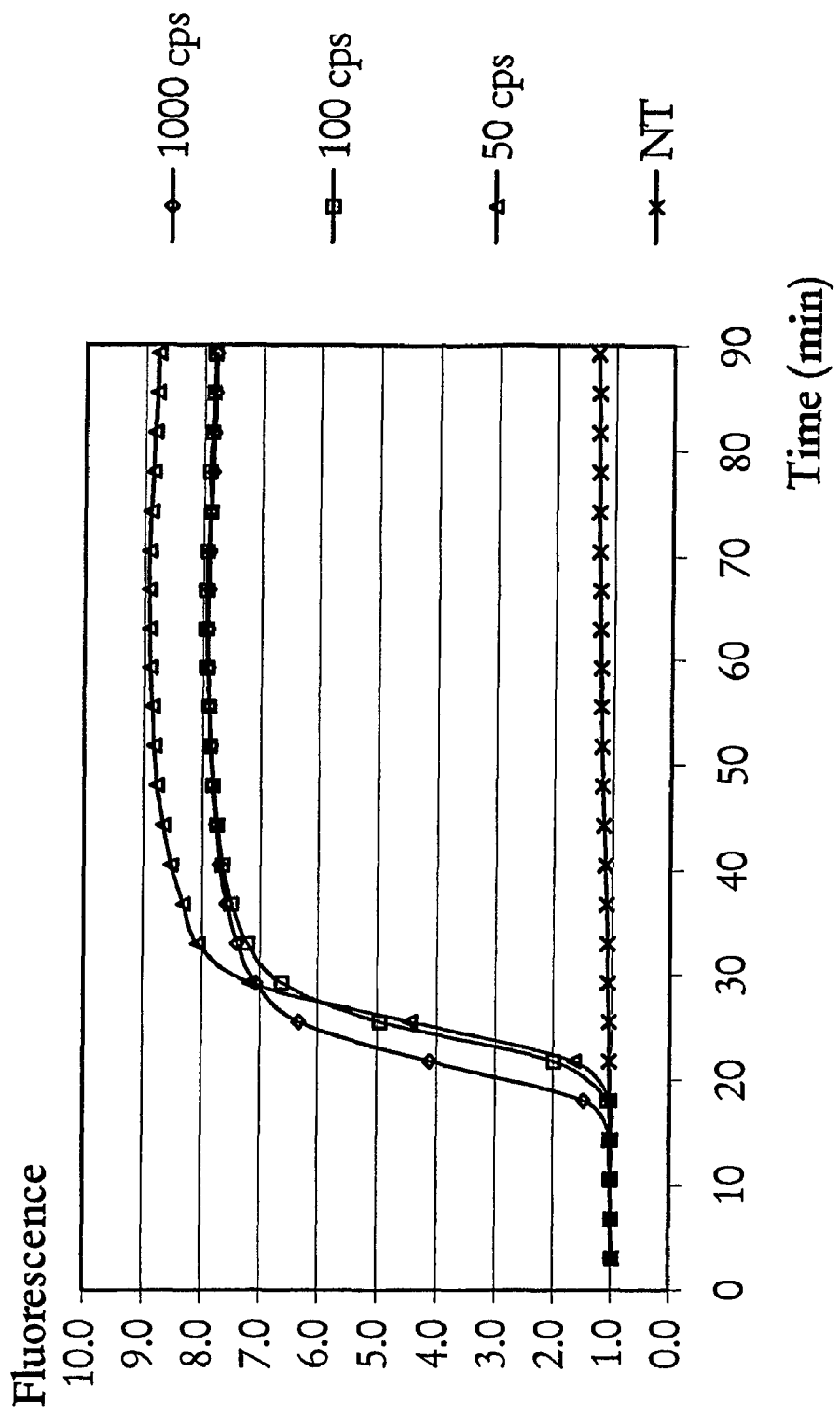
Figure 3:
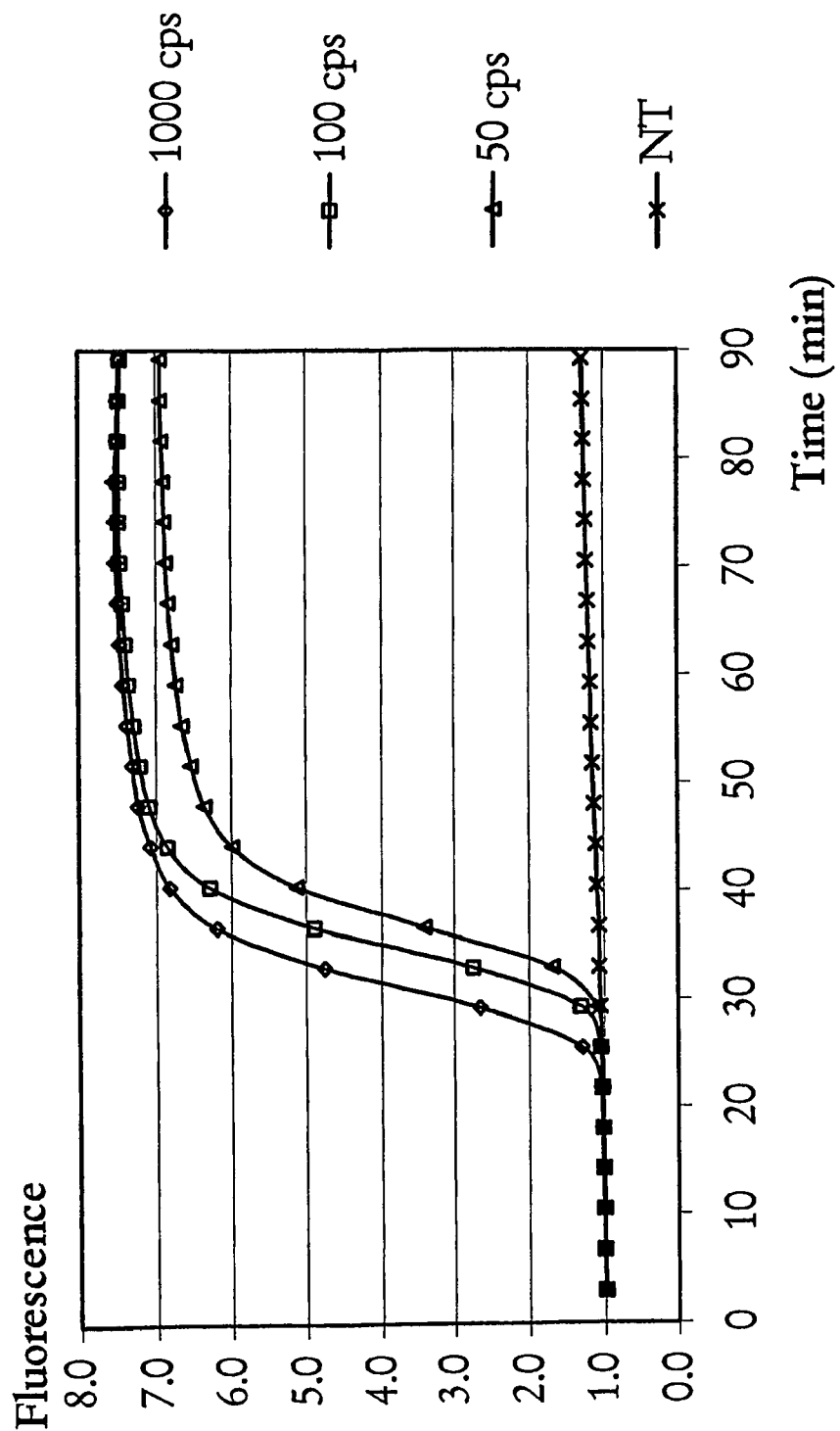
Figure 4:
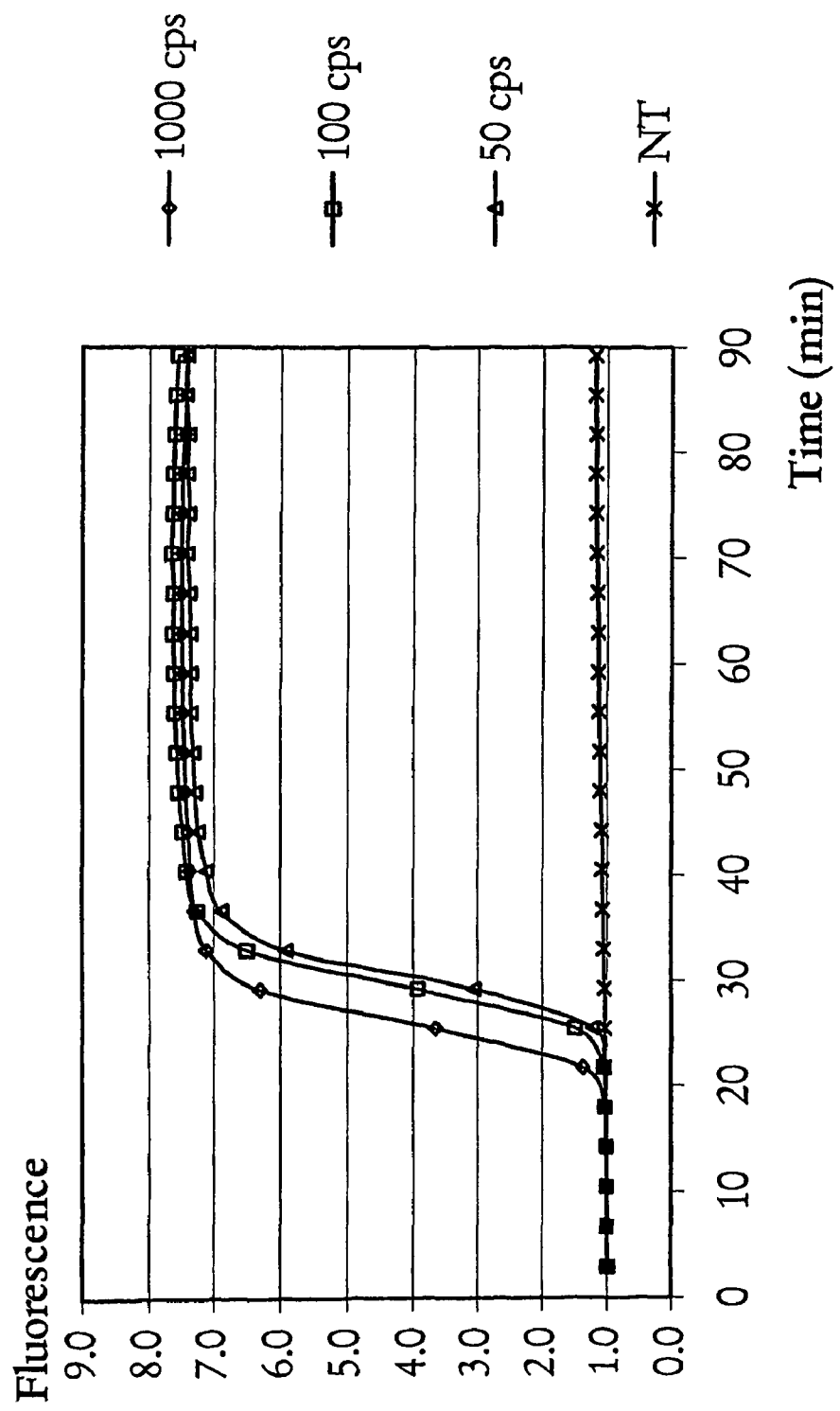
Figure 5:
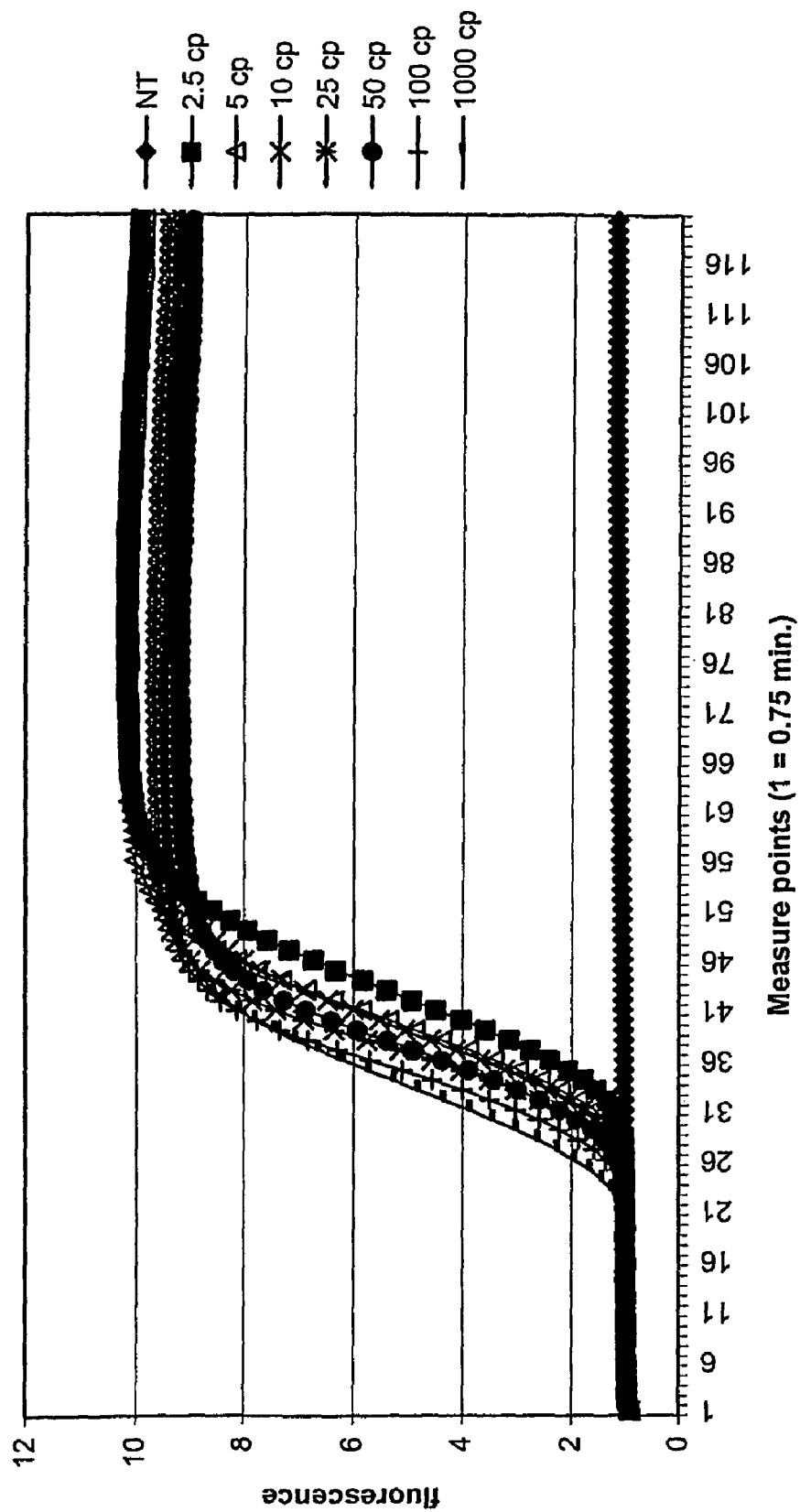

Primer pairs that can be formed with the SARS-CoV REP primers (Table 1) are shown in Table 2 together with the size and genome location of the resulting amplicons. Results are shown in FIGS. 1-4 and FIGS. 7-11.

TABLE 2

SARS-CoV REP primer combinations:

| Primer Combination | Amplicon Size | Genome Location |
|---|---|---|
| SARS-CoV REP P1.1/P2.1 | 192 nt | 18,153-18,344 |
| SARS-CoV REP P1.1/P2.2 | 144 nt | 18,201-18,344 |
| SARS-CoV REP P1.1/P2.3 | 124 nt | 18,221-18,344 |
| SARS-CoV REP P1.2/P2.1 | 153 nt | 18,153-18,305 |
| SARS-CoV REP P1.2/P2.2 | 105 nt | 18,201-18,305 |
| SARS-CoV REP P1.2/P2.3 | 85 nt | 18,221-18,305 |
| SARS-CoV REP P1.3/P2.1 | 264 nt | 18,153-18,416 |
| SARS-CoV REP P1.3/P2.2 | 216 nt | 18,201-18,416 |
| SARS-CoV REP P1.3/P2.3 | 196 nt | 18,221-18,416 |

FIGS. 1-4 (for the first four pairs P1.1/P2.1, P1.1/P2.2, P1.2/P2.1 and P1.2/P2.2) show that all primer pairs revealed a positive result for the different amounts of in vitro RNA that were tested. However, analysis of the moment at which the different reactions start to reveal fluorescence signals that are well above the background signal showed that primer combination P2.2/P1.1 has strikingly lower Time-To-Positivity (TTP) values as the other primer combinations. Therefore, oligonucleotide primers P1.1 and P2.2 were selected as the most ideal primer pair for the amplification of SARS CoV RNA.

In a next step, all nine SARS-CoV REP primer pairs (Table 2) were analysed. Since P1.3 was chosen outside the fragment covered by the in vitro RNA, these primer combinations were analysed on RNA extracted from a cultured SARS-CoV virus stock (provided by Robert Koch Institute, Berlin, Germany). A nucleic acid extract was prepared from 5 µl of this virus stock containing about 5000 genome equivalents (geq). From this nucleic acid extract a ten-fold dilution series in water was prepared containing nucleic acid levels as if extracted from 5000 geq (undiluted extract) down to 0.01 geq. Each of the nine SARS-CoV REP primer combinations (see Table 2) was tested with this dilution series in real-time NASBA reactions using molecular beacon SARS-CoV REP MB-1 for detection. In addition to FIGS. 1-4, results are shown in FIG. 7-11 for the other primer pairs (respectively for the following pairs P1.1/P2.3, P1.2/P2.3, P1.3/P2.1, P1.3/P2.2 and P1.3/P2.3).

The four primer combinations previously tested on in vitro RNA, revealed a similar result with viral RNA extracted from the cultured SARS-CoV virus stock (FIGS. 1-4). Regarding sensitivity of the primer combinations, some minor differences were observed, but whether these are significant, cannot be concluded on the basis of this limited evaluation. However, again primer pair P1.1/P2.2 showed faster kinetics and shorter time-to-positivity values as the other three primer combinations.

For some of the new primer combinations containing either P1.3 or P2.3, sensitivity was comparable to the sensitivity of primer combination SARS-CoV REP P1.1/P2.2. In addition, primer combination SARS-CoV REP P1.1/P2.3 (FIG. 7) showed kinetics and time-to-positivity values similar to those of primer combination P1.1/P2.2. Strikingly, primer combination SARS-CoV REP P1.2/P1.3 (FIG. 8) revealed a much lower sensitivity as any of the other primer pairs. Probably, this is due to the small size of only 85 nts for the amplicons generated by this primer pair (see Table 2). For NASBA amplification, an amplicon size below 100 nts is considered sub optimal. With 264 nts, primer pair SARS-CoV REP P1.3/P2.1 revealed the longest amplicons. This might explain the significantly lower kinetics, especially for the lower input levels, observed for this primer combination (FIG. 9).

From the nine possible primer combinations, more or less arbitrarily, primer combination SARS-CoV REP P1.1/P2.2 was selected for further evaluation and in combination with molecular beacon SARS-CoV REP MB-1 will be referred to as primer/beacon mix SARS-CoV REP-1.

Another primer combination of interest in this region of the SARS-CoV genome, primer pair SARS-CoV REP P1.3/P2.3 in combination with molecular beacon SARS-CoV REP MB-1 was selected as SARS-CoV REP-2 for further studies.

Example 3

Analytical Sensitivity of the Selected Primer Pair

To determine the analytical sensitivity of the selected primer pair (P1.1/P2.2) a dilution series of SARS CoV in vitro RNA was tested with the selected primer pair. The RNA dilution series was made in NASBA water from a 1×10⁵ copies/μl RNA stock solution. Results are summarized in FIG. 5 and show a very good analytical sensitivity with positive results down to 2.5 copies of in vitro RNA in de amplification, while the negative control remained negative. In present evaluation, sensitivity of the selected primer pair (P1.3/P2.3) appeared somewhat less (one ten-fold dilution) as for the selected primer pair (P1.1/P2.2), but this is not considered to be a significant difference.

Example 4

SARS CoV REP-1 "ECL" Version

Based on the primers SARS-CoV P1.1.P2.2 primers and molecular beacon MB-1, primers and a capture probe were designed that could be used to perform real-time NASBA amplification and subsequent end-point detection by Electro-ChemiLuminescence hereafter called ECL (18). Therefore, the Basic Kit ECL-tail (Deiman, B. et al. (19)) was added to the 5'-end of SARS-CoV REP P2.2 and the hybridizing fragment of molecular beacon SARS-CoV REP MB-1 was synthesized as a biotinylated oligonucleotide resulting in SARS-CoV REP 2.2 "ECL" and SARS-CoV REP Cap-1 (Capture probe), respectively. Sequences, polarity, and genome locations of SARS-CoV REP-1 "ECL" are outlined in Table 3. For the P1 primer (SARS-CoV REP P1.1) the T7 polymerase promoter sequence is depicted in small characters. For the P2 primer (SARS-CoV REP P2.2 "ECL") the ECL tail sequence added at the 5'-end of the primer is depicted in small characters. The SARS-CoV Capture probe carries a biotin moiety at its 5'-end. Coordinates for the location of the hybridizing segments of the primers and the capture probe are derived from the genome sequence of SARS-CoV strain TOR2 (EMBL/GenBank Accession Number AY274119).

fication reactions. Results are summarized in Table 4, reflecting fluorescence signals for SARS-CoV REP-1 and both fluorescence signals and ECL counts for SARS-CoV REP-1 "ECL". The typical "all-or-nothing" results as obtained for SARS-CoV REP-1 were also obtained for the ECL-version of this primer/beacon mix and sensitivity of both primer/beacon mixtures is identical. Comparison of real-time versus ECL results for SARS-CoV REP-1 "ECL" revealed a similar result: ECL counts were either very low or "overrange" (>10⁷ counts) and dilutions found positive with real-time detection were positive with ECL detection as well.

TABLE 4

Comparison of SARS-CoV REP-1 primer/beacon mixtures and real-time versus ECL detection.

SARS CoV REP-1

| RNA input (cps per reaction) | Fluorescence signal |
|---|---|
| 10 | 9.86 |
| 5 | 9.45 |
| 1 | 9.36 |
| 0.5 | 9.53 |
| 0.1 | 9.02 |
| 0.05 | 8.98 |
| 0.01 | 1.19 |
| No Template | 1.19 |

SARS CoV REP-1 "ECL"

| RNA input (cps per reaction) | Fluorescence signal | ECL signal (counts) |
|---|---|---|
| 10 | 8.61 | 10.000.001 |
| 5 | 8.87 | 10.000.001 |
| 1 | 8.97 | 10.000.001 |
| 0.5 | 9.18 | 10.000.001 |

TABLE 3

Primers and biotinylated capture probe for the amplification and ECL-based end-point detection of a region located in the replicase gene of SARS-CoV.

| Description | Sequence (SEQ ID number) | Length | Genome location | Purity (CE) |
|---|---|---|---|---|
| SARS-CoV REP P.1.1 | 5'-aattctaatacgactcactatagggAACATAACC AGTCGGTACAGCTACTA-3' (SEQ ID 4) | 51 nt | 18,319-18,344 | 74.1% |
| SARS-CoV REP P2.2 ECL | 5'-gatgcaaggtcgcatatgagGAAGCTATTCGTCA CGTTCG-3' (SEQ ID 7) | 40 nt | 18,201-18,220 | 88.6% |
| SARS-CoV REP Cap-1 | 5'-(Biotin)-GCTGTCATGCAACTAGAGATG CTGT-3' (SEQ ID 46) | 21 nt | 18,246-18,271 | ND |

Primer/beacon mix "ECL" (containing primers SARS-CoV REP P1.1 and SARS-CoV REP P2.2 "ECL" in combination with SARS-CoV REP MB-1) was tested in real-time NASBA reactions using a dilution series of in vitro RNA (18) as input material in the reactions. For comparison, the same dilution series was amplified with the standard SARS-CoV REP-1 primer/beacon mix. Subsequently, ECL detection was performed on the SARS-CoV REP P1.1 and SARS-CoV REP P2.2 in combination with SARS-CoV REP MB-1 reactions, allowing direct comparison of ECL end-point detection versus real-time molecular beacon detection on the same amplification TABLE 4-continued Comparison of SARS-CoV REP-1 primer/beacon mixtures and real-time versus ECL detection.

| 0.1 | 8.67 | 10.000.001 |
|---|---|---|
| 0.05 | 8.69 | 10.000.001 |
| 0.01 | 1.15 | 171 |
| No Template | 1.17 | 172 |

In vitro RNA was amplified with primer/beacon mixtures SARS-CoV REP-1 and SARS-CoV REP-1 "ECL". For subsequent ECL detection, SARS-CoV REP Cap-1 was used in combination with the generic ECL probe of the NucliSens Basic Kit.

Second Set of Examples Related to RNA Issued from the Viral Gene Encoding the Nucleocapsid Protein:

Example 5

SARS-CoV Nucleocapsid Primers Design

The SARS-CoV Nucleocapsid (N) protein is encoded by the open reading frame spanning nucleotides 28,120-29,388 on the viral genome. Primers were designed for two regions in the nucleocapsid gene, the first region encompassing nucleotides 28,251-28,485 (region 1) and the second region spanning nucleotides 28,851-29,101 (region 2). For each region, initially two P1 primers (SARS-CoV N P1.1 and P1.2 for region 1; SARS-CoV N P1.3 and P1.4 for region 2) and two P2 primers (SARS-CoV N P2.1 and P2.2 for region 1; SARS-CoV N P2.3 and P2.4 for region 2) were designed. In each of the regions an additional P2 primer was chosen that hybridized closer to the sequence targeted by the molecular beacon for that region (SARS-CoV N P2.5 for region 1; SARS-CoV N P2.6 for region 2). Consequently, smaller amplicons could be generated which might have a positive impact on the sensitivity of SARS-CoV N subgenomic RNA detection. Sequences, polarity, and genome locations of all SARS-CoV N primers are shown in Table 5.

For the P1 primers (SARS-CoV N P1.1, P1.2, P1.3 and P1.4) the T7 Polymerase promoter sequence is depicted in small characters. Coordinates for the location of the primers are derived from the complete genome sequence of SARS-CoV isolate TOR2 (GenBank Accession number AY274119).

With two P1 primers and three P2 primers, six different SARS-CoV N primer combinations can be composed for each of the two regions (Table 6).

TABLE 6

SARS-CoV N primers combinations.

| Primer Combination for region 1 | Amplicon Size | Genome Location |
|---|---|---|
| SARS-CoV N P1.1/P2.1 | 203 nt | 28,251-28,453 |
| SARS-CoV N P1.1/P2.2 | 139 nt | 28,315-28,453 |
| SARS-CoV N P1.1/P2.5 | 102 nt | 28,352-28,453 |
| SARS-CoV N P1.2/P2.1 | 235 nt | 28,251-28,485 |
| SARS-CoV N P1.2/P2.2 | 171 nt | 28,315-28,485 |
| SARS-CoV N P1.2/P2.5 | 134 nt | 28,352-28,485 |

TABLE 5

Primers for the amplification in real-time of two regions located in the Nucleocapsid gene of SARS-CoV.

| Description | Sequence (SEQ ID number) | Length | Genome Location | Purity (CE) |
|---|---|---|---|---|
| Region 1 | | | | |
| SARS-CoV N P1.1 | 5'-aattctaatacgactcactatagggAGAAGTACCA TCT GGGGCTGA-3' (T7 + SEQ ID 15) | 46 nt | 28,433-28,453 | 85.5% |
| SARS-CoV N P1.2 | 5'-aattctaatacgactcactatagggAAGTGAAGCT TCT GGGCCAGTTCCTA-3' (T7 + SEQ ID 16) | 51 nt | 28,460-28,485 | 85.1% |
| SARS-CoV N P2.1 | 5'-AGGTTTACCCAATAATACTGCGT-3' (SEQ ID 18) | 23 nt | 28,251-28,273 | 90.2% |
| SARS-CoV N P2.2 | 5'-AGATTCCCTCGAGGCCAGGGCGT-3' (SEQ ID 19) | 23 nt | 28,315-28,337 | 91.5% |
| SARS-CoV N P2.5 | 5'-ATAGTGGTCCAGATGACCAAAT-3' (SEQ ID 20) | 22 nt | 28,352-28,373 | 90.0% |
| Region 2 | | | | |
| SARS-CoV N P1.3 | 5'-aattctaatacgactcactatagggAAGAATGCAGAG GCA CTTGGAGCA-3' (SEQ ID 41) | 49 nt | 29,043-29,066 | 82.1% |
| SARS-CoV N P1.4 | 5'-aattctaatacgactcactatagggAAGGTGTGACTT CCATGC CAA-3' (SEQ ID 42) | 46 nt | 29,081-29,101 | 81.8% |
| SARS-CoV N P2.3 | 5'-CCAAACTGTCACTAAGAAATCTGCT-3' (SEQ ID 27) | 25 nt | 28,851-28,875 | 87.5% |
| SARS-CoV N P2.4 | 5'-CTCAAGCATTTGGGAGACGTGGT-3' (SEQ ID 28) | 23 nt | 28,934-28,956 | 82.8% |
| SARS-CoV N P2.6 | 5'-CAGAACAAACCCAAGGAAATT-3' (SEQ ID 29) | 21 nt | 28,958-28,978 | 89.8% |

TABLE 6-continued

SARS-CoV N primers combinations.

| Primer Combination for region 2 | Amplicon Size | Genome Location |
|---|---|---|
| SARS-CoV N P1.3/P2.3 | 216 nt | 28,851-29,066 |
| SARS-CoV N P1.3/P2.4 | 133 nt | 28,934-29,066 |
| SARS-CoV N P1.3/P2.6 | 109 nt | 28,958-29,066 |
| SARS-CoV N P1.4/P2.3 | 251 nt | 28,851-29,101 |
| SARS-CoV N P1.4/P2.4 | 168 nt | 28,934-29,101 |
| SARS-CoV N P1.4/P2.6 | 144 nt | 28,958-29,101 |

Example 6

SARS-CoV Nucleocapsid Molecular Beacons Design

Figure 12B:
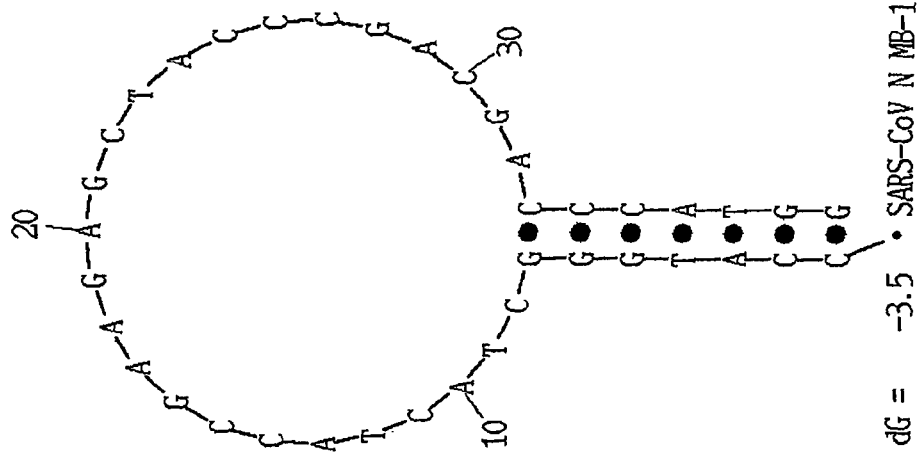
Figure 12A:
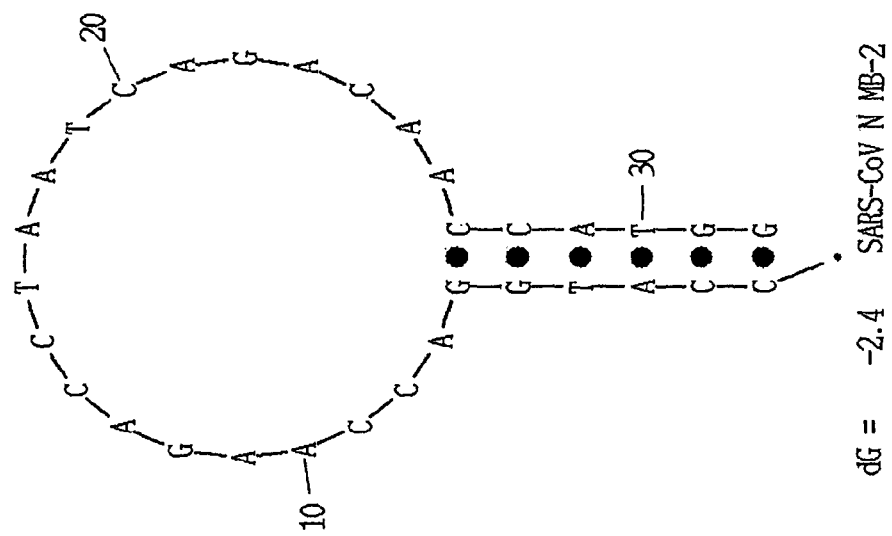
Figure 13:
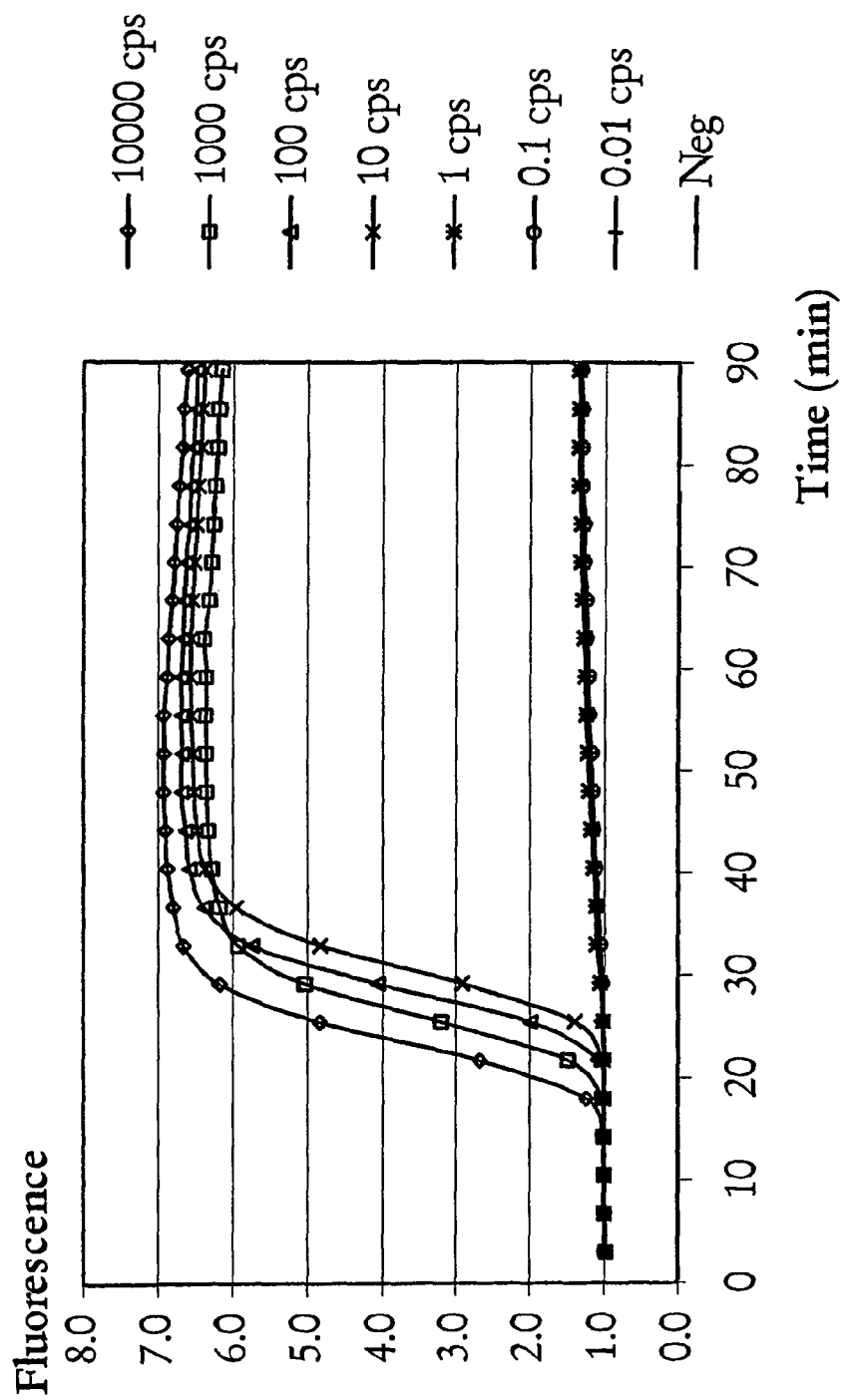
Figure 14:
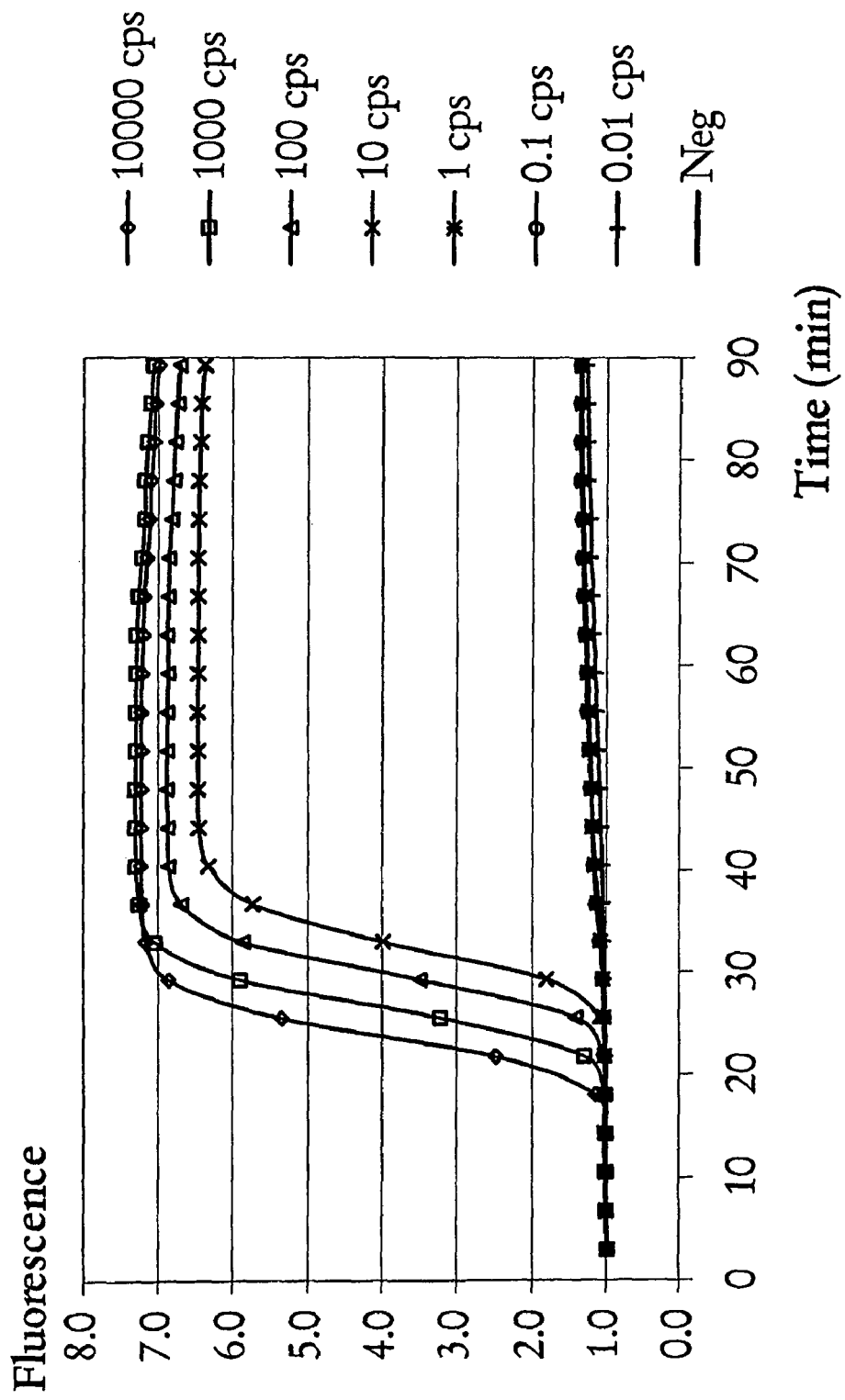
Figure 15:
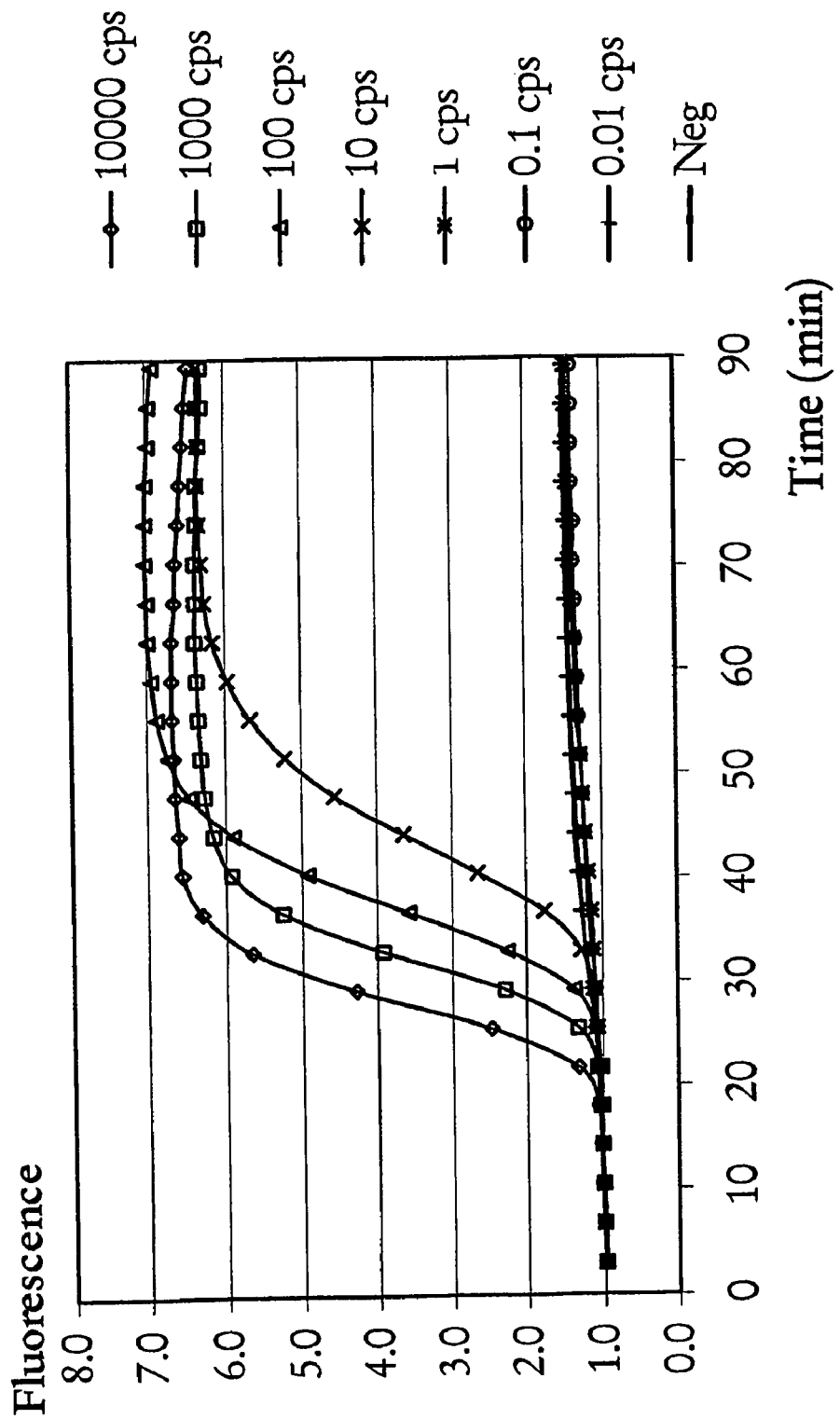
Figure 16:
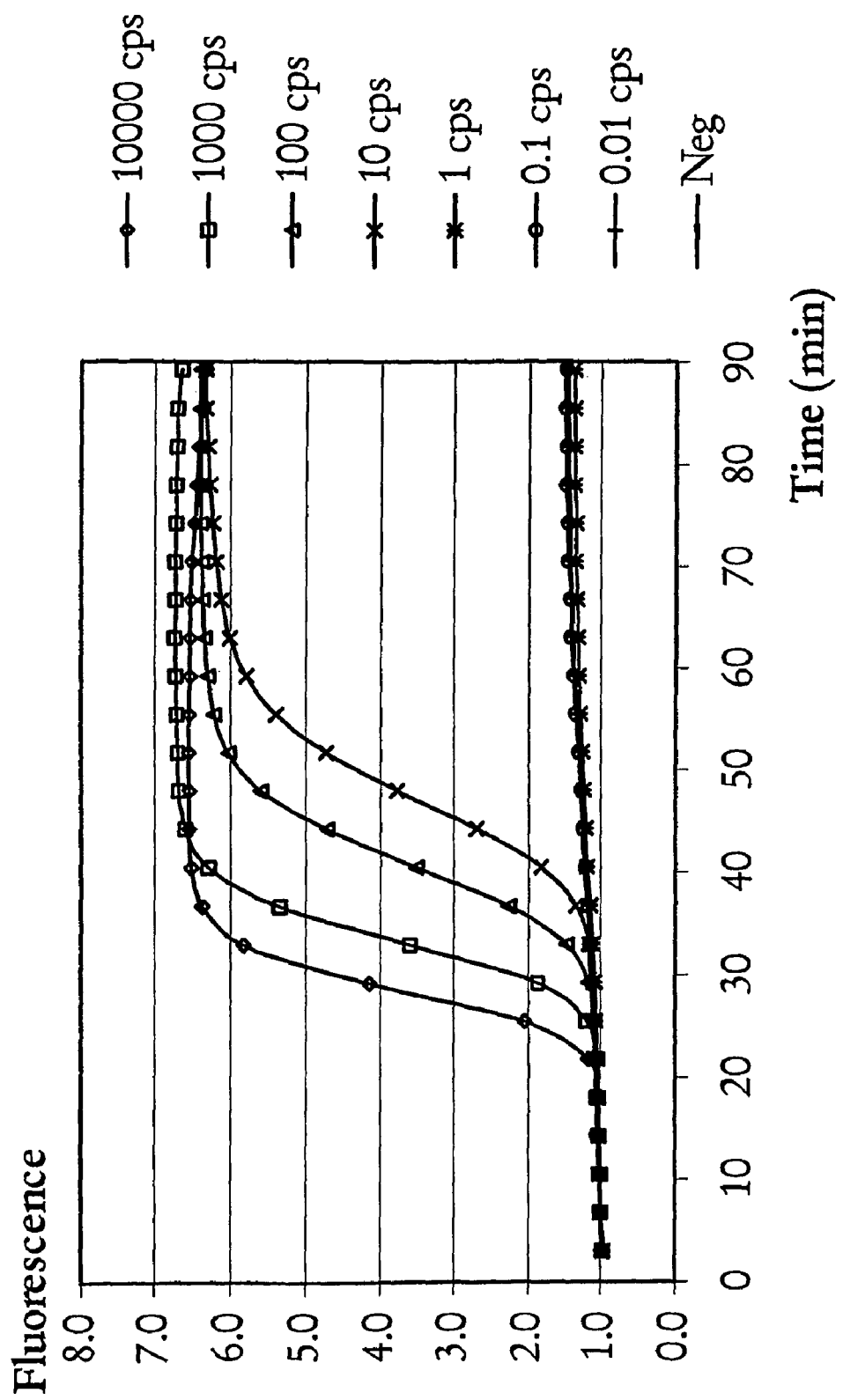
Figure 17:
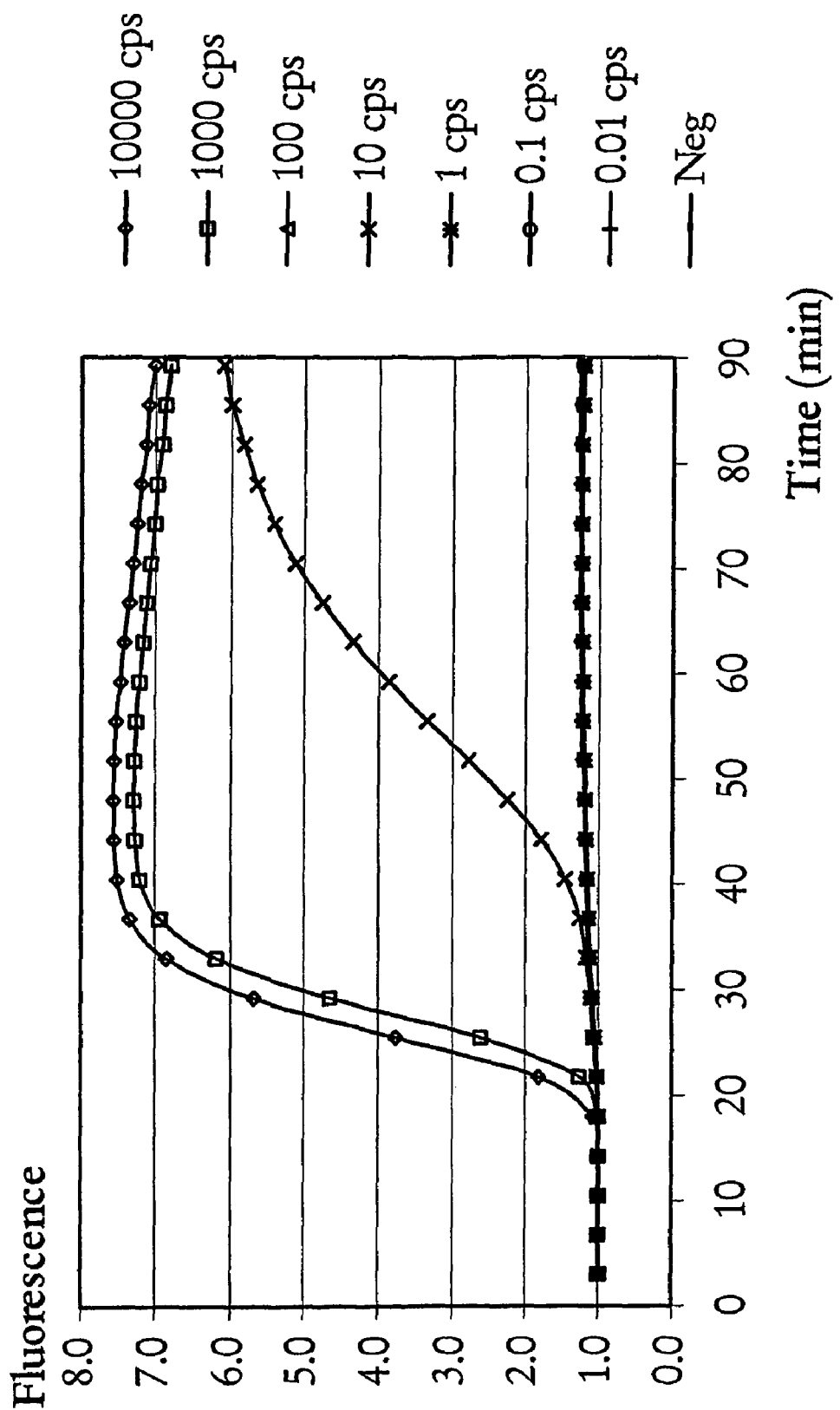
Figure 18:
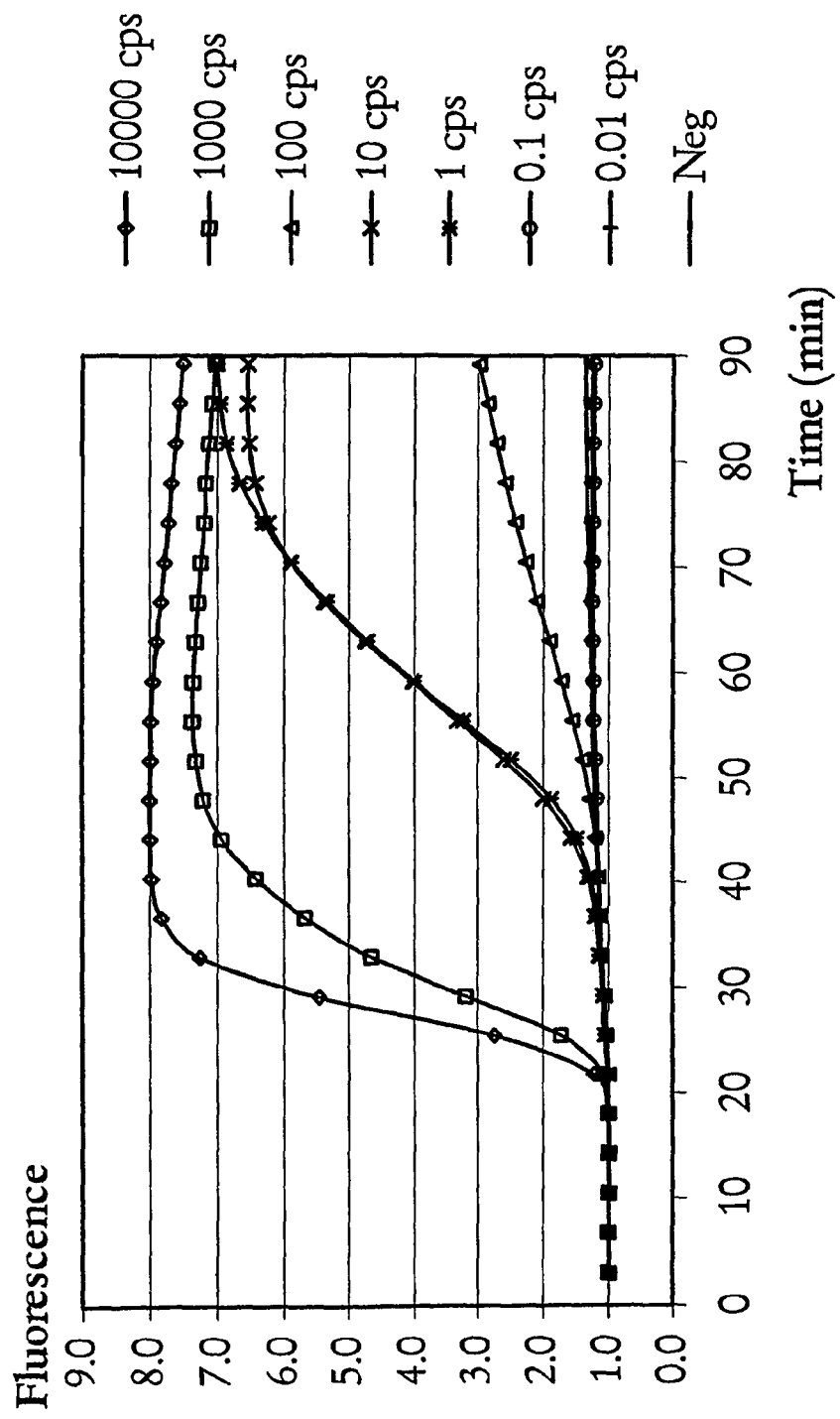
Figure 19:
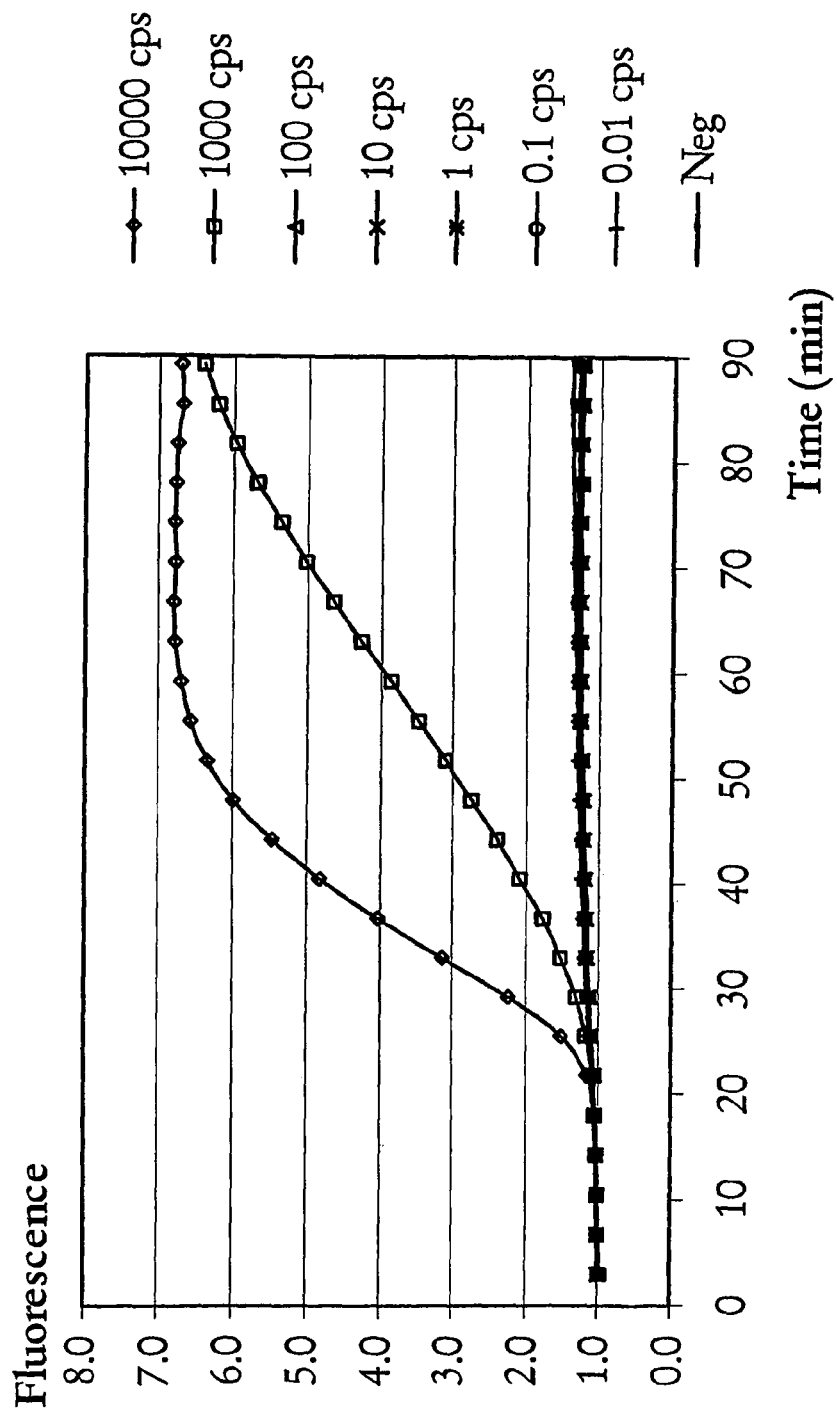
Figure 20:
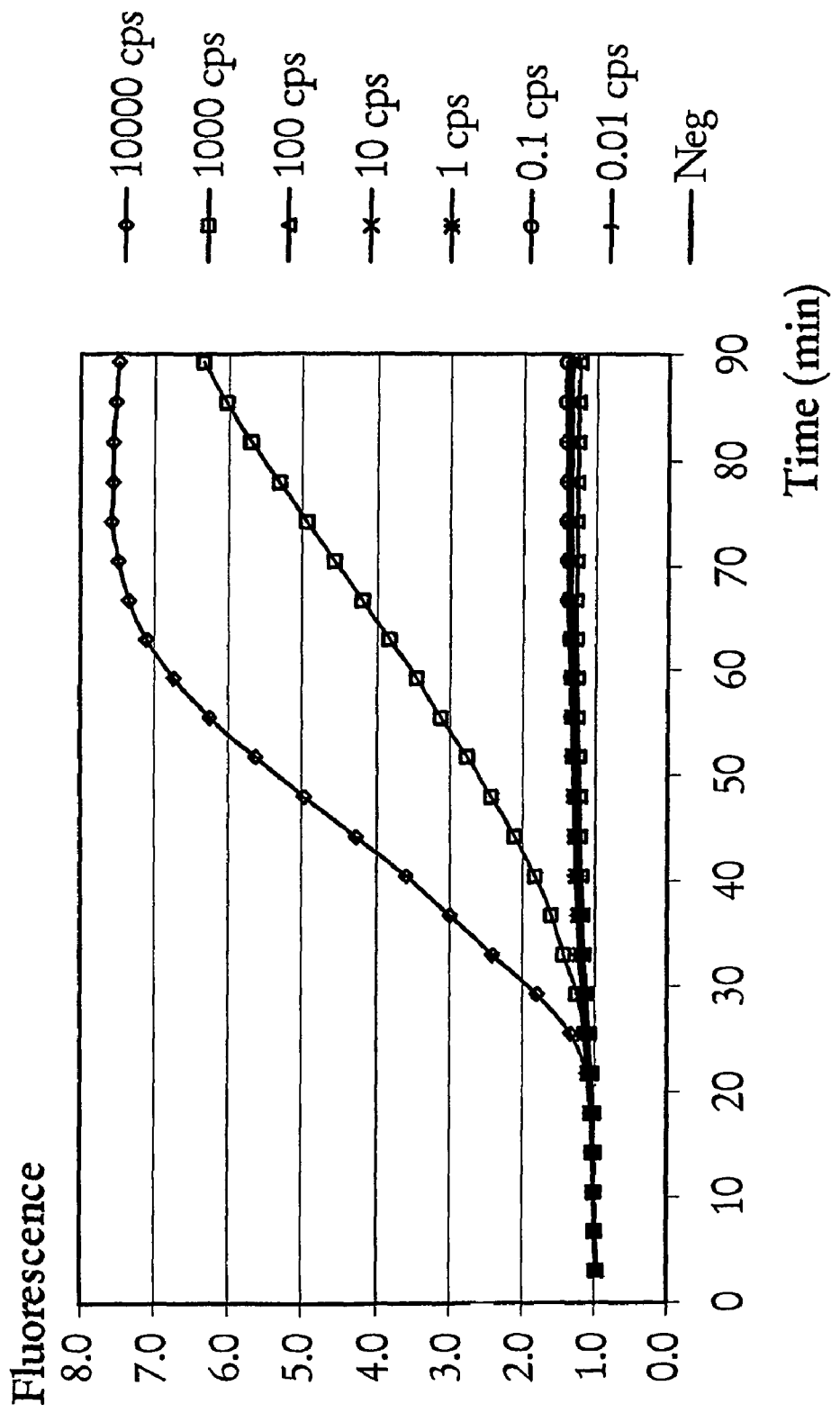
Figure 21:
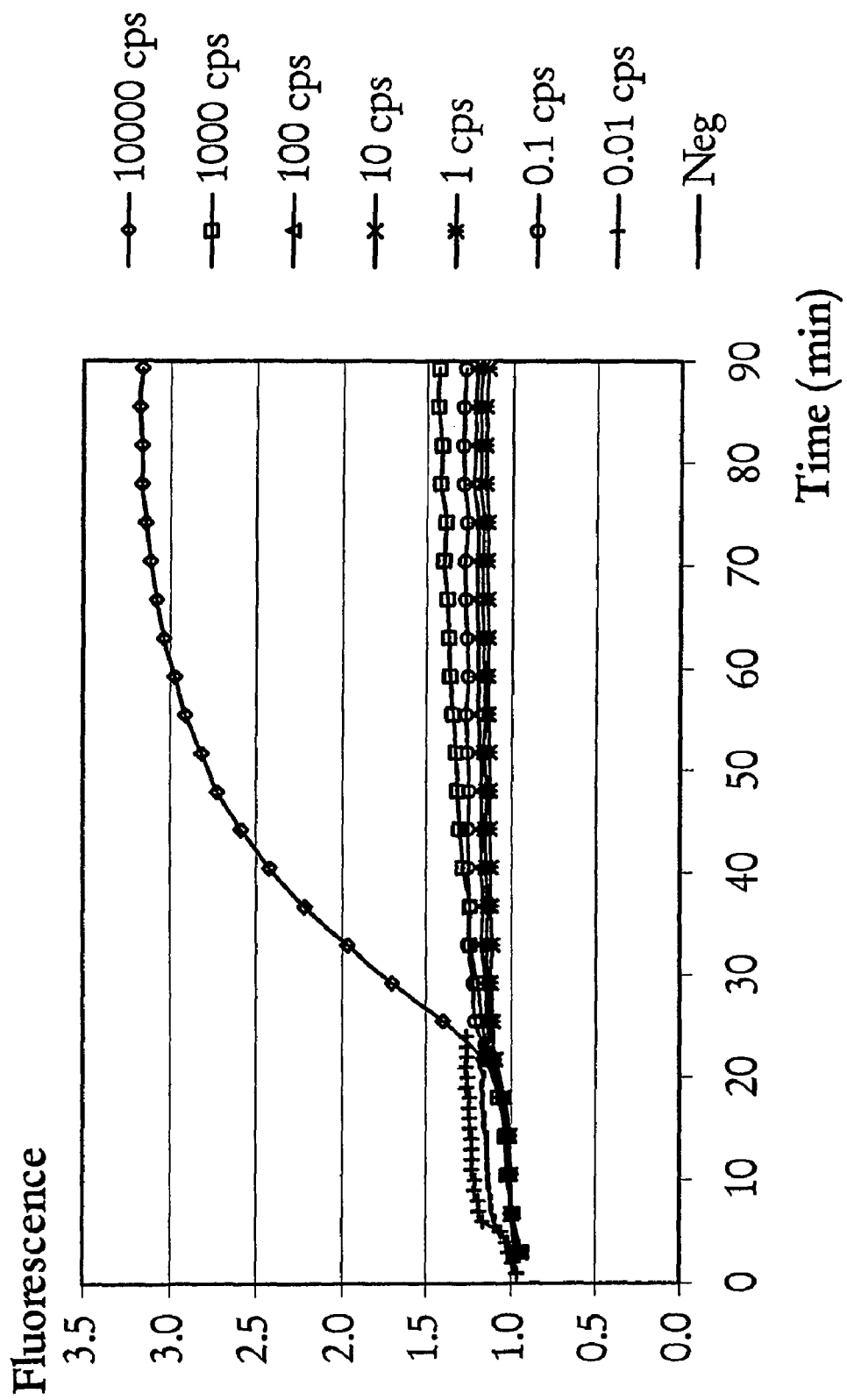
Figure 22:
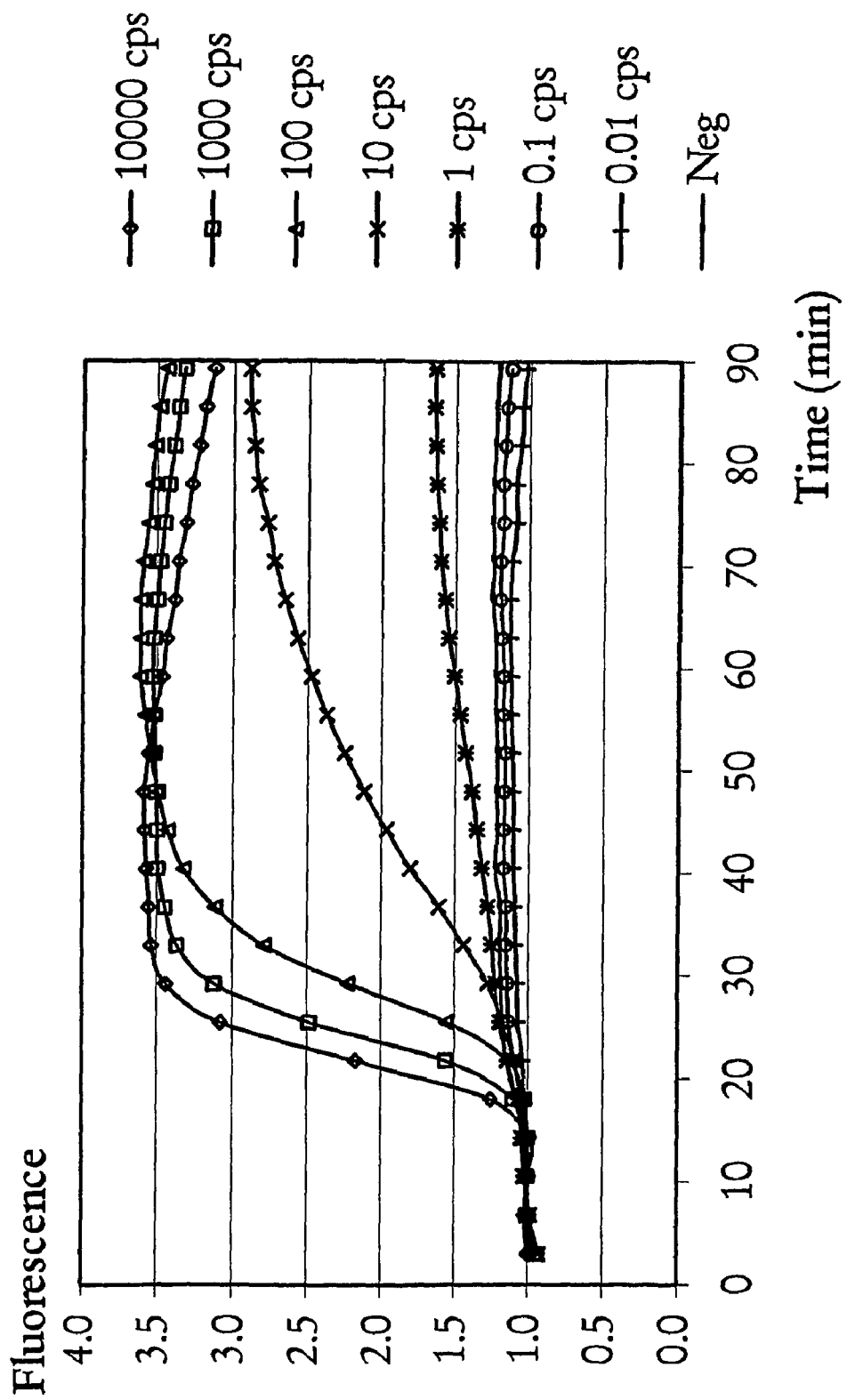
Figure 23:
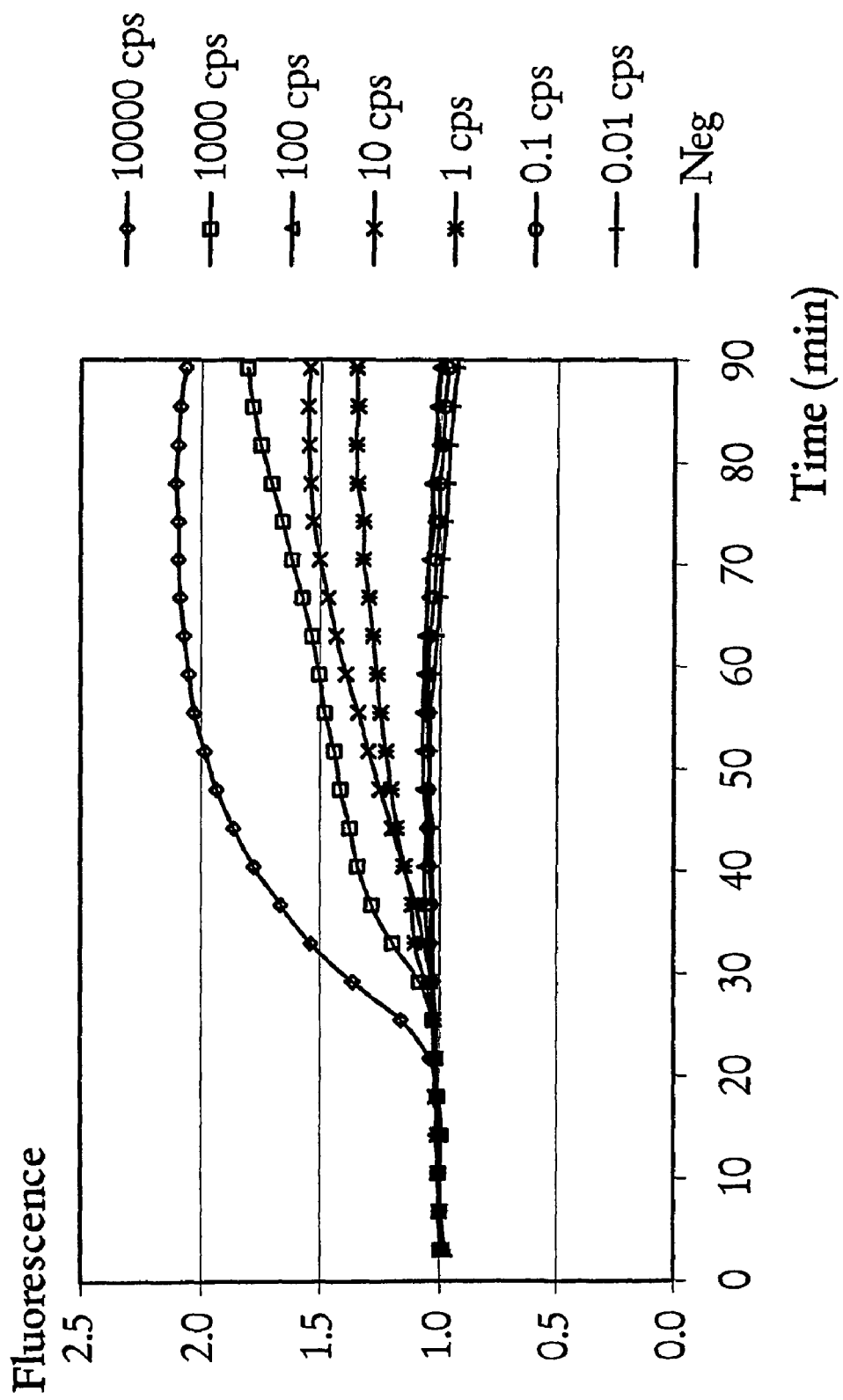
Figure 24:
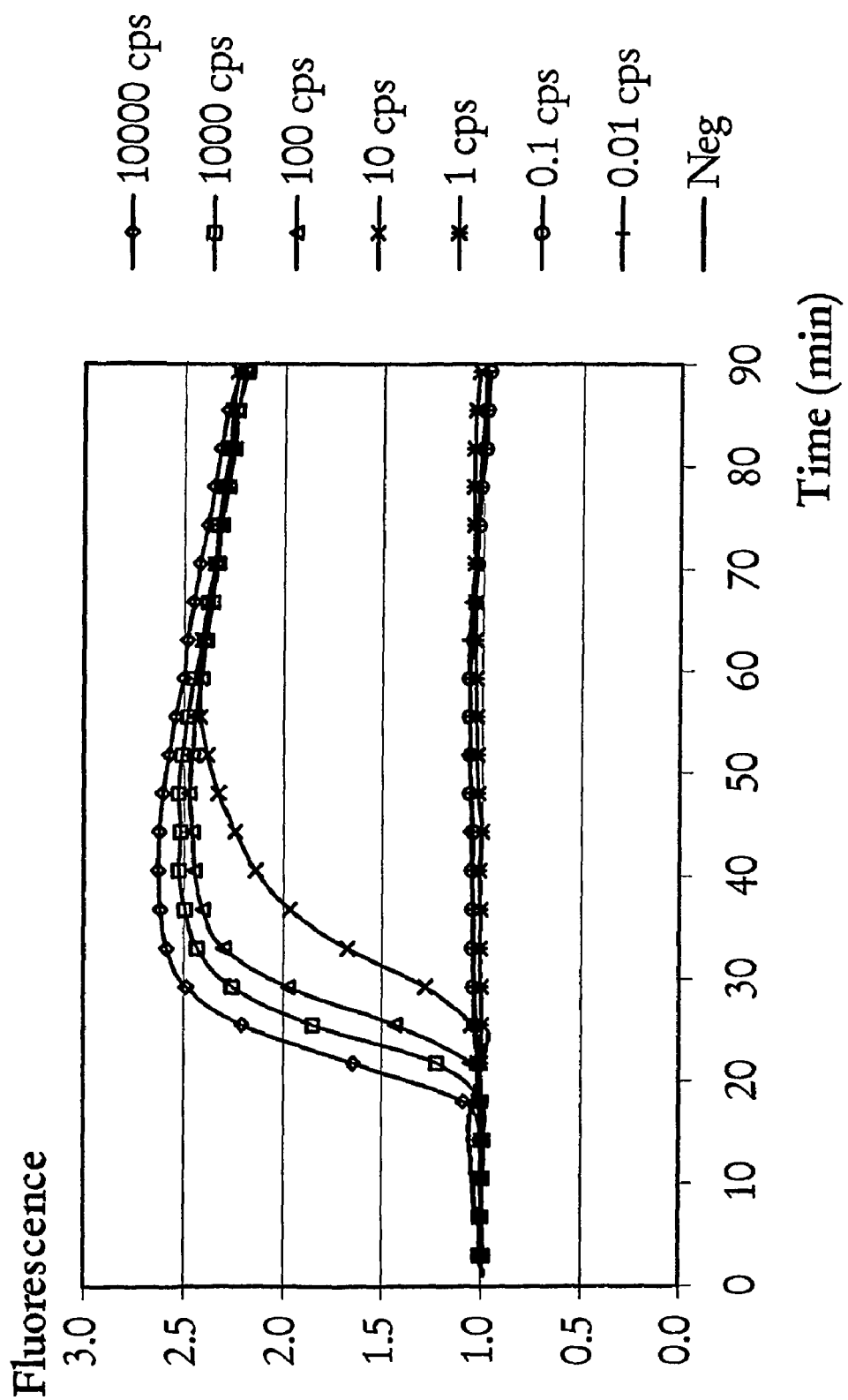
Figure 25:
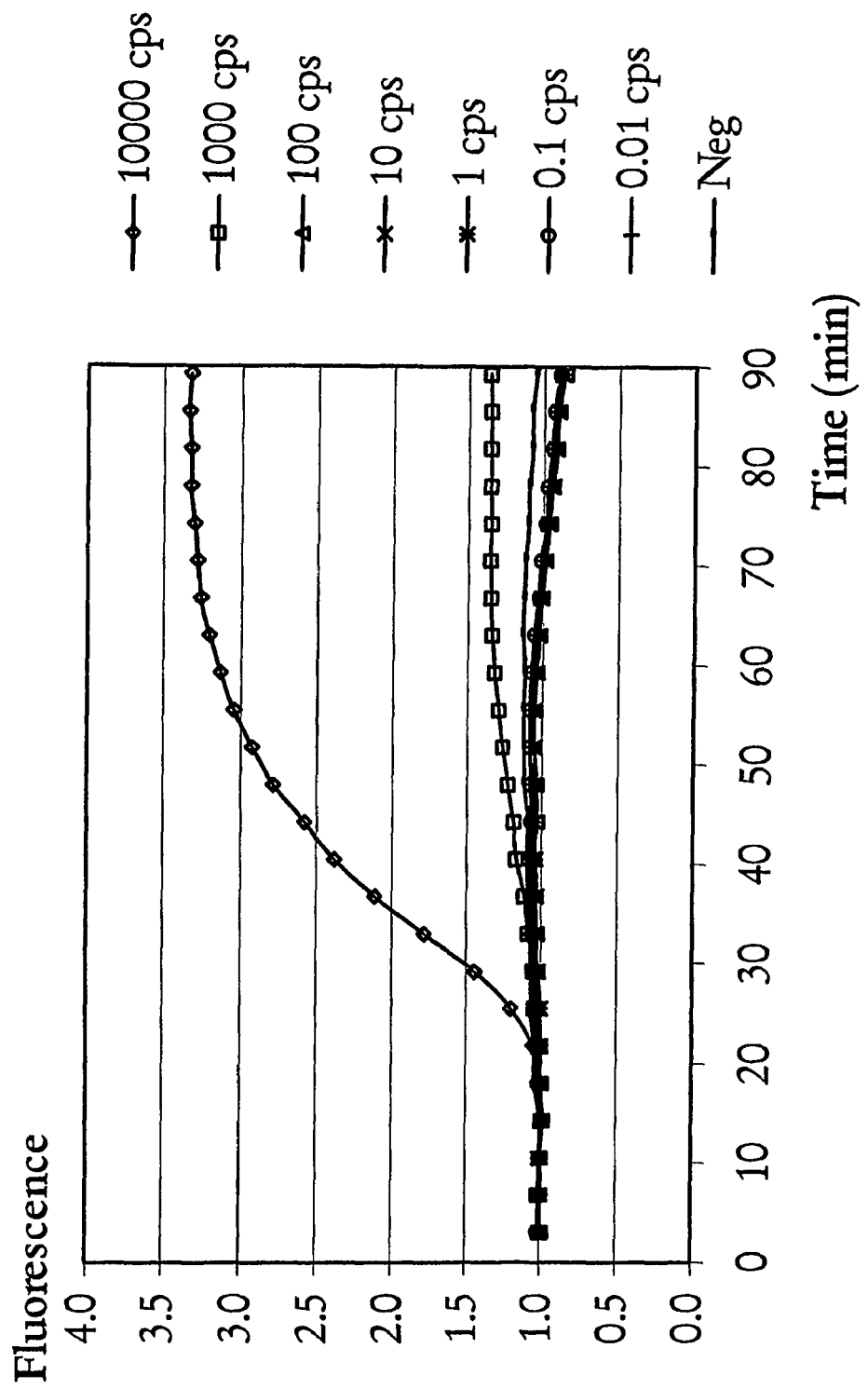
Figure 26:
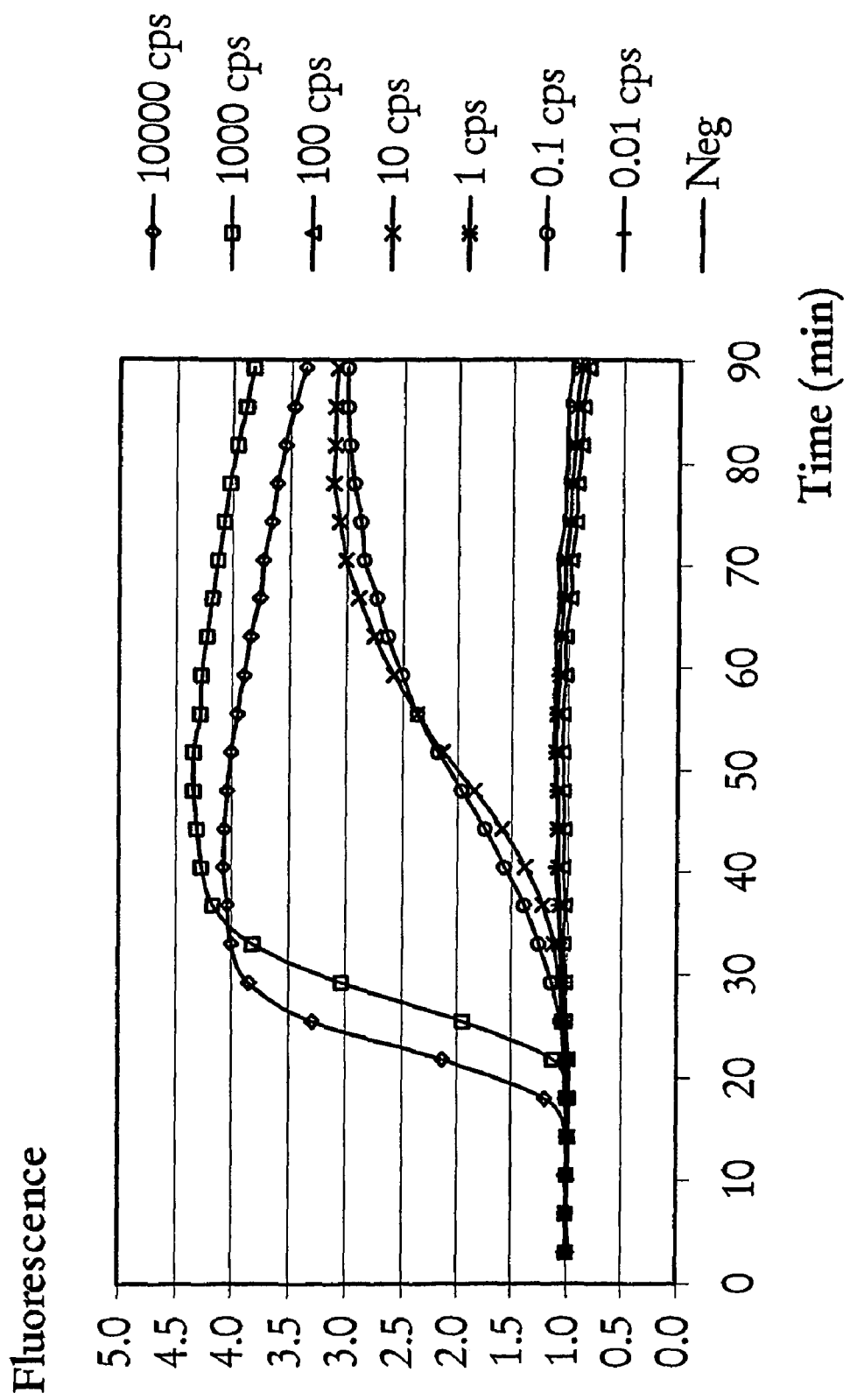
Figure 27:
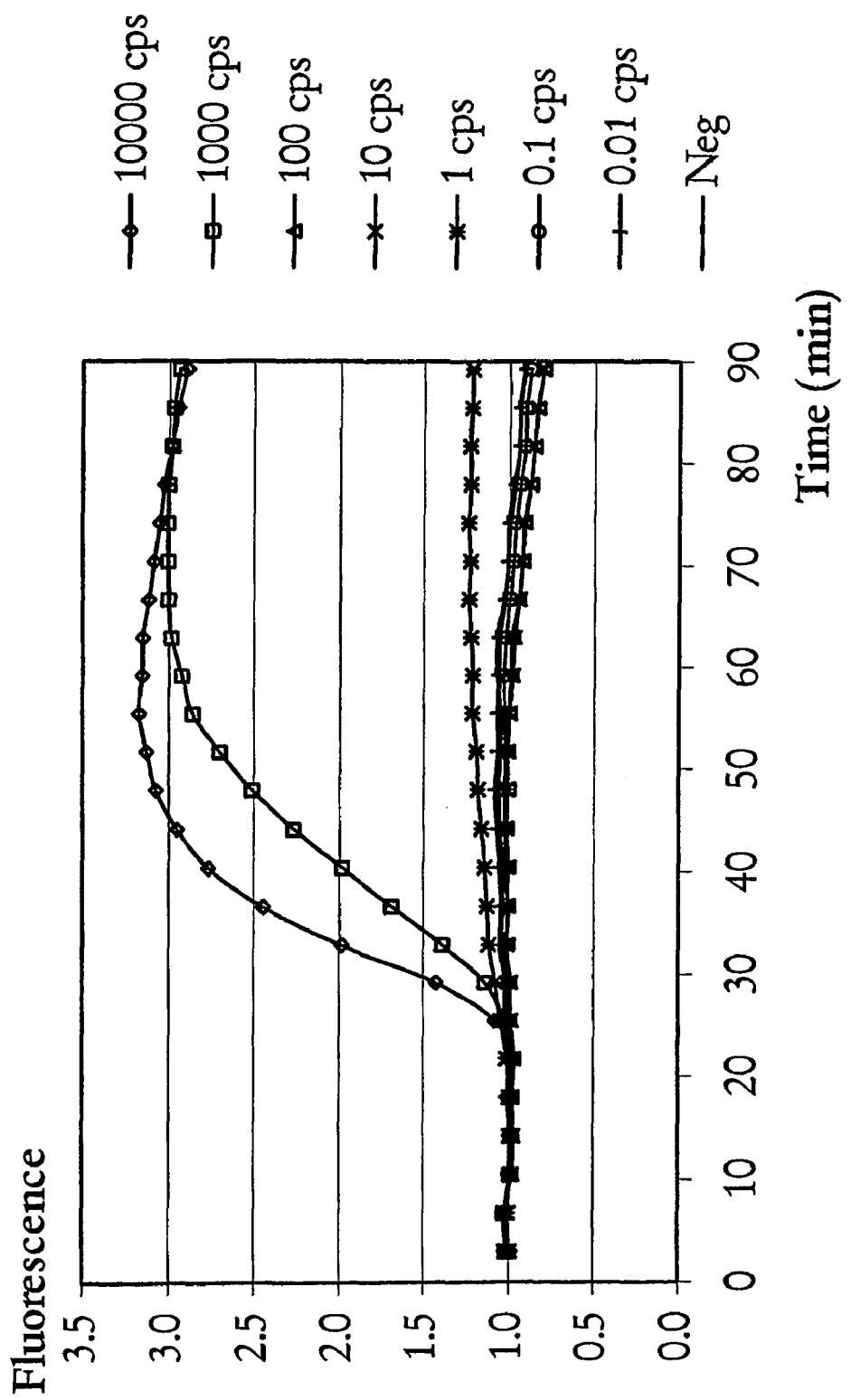
Figure 28:
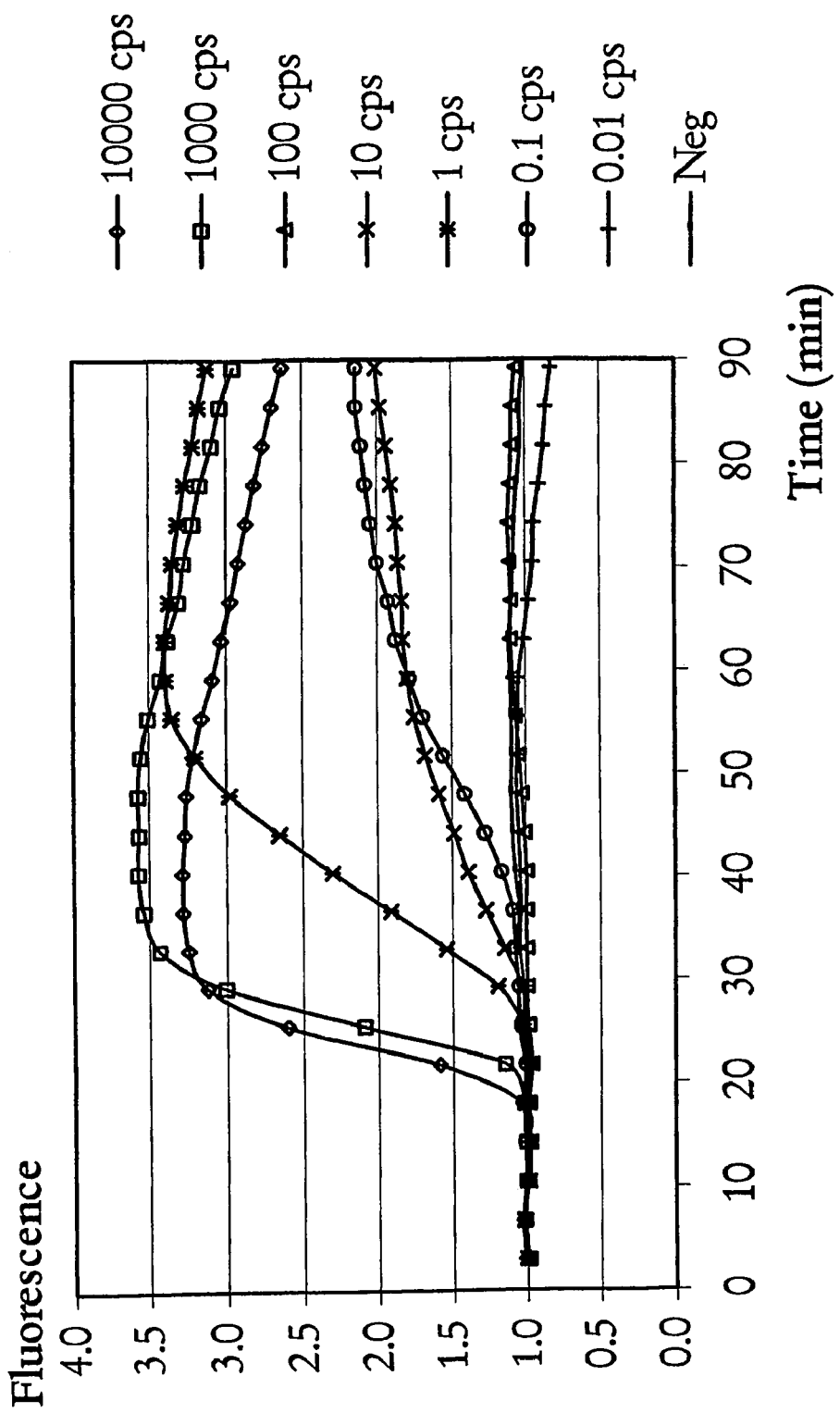
Figure 29:
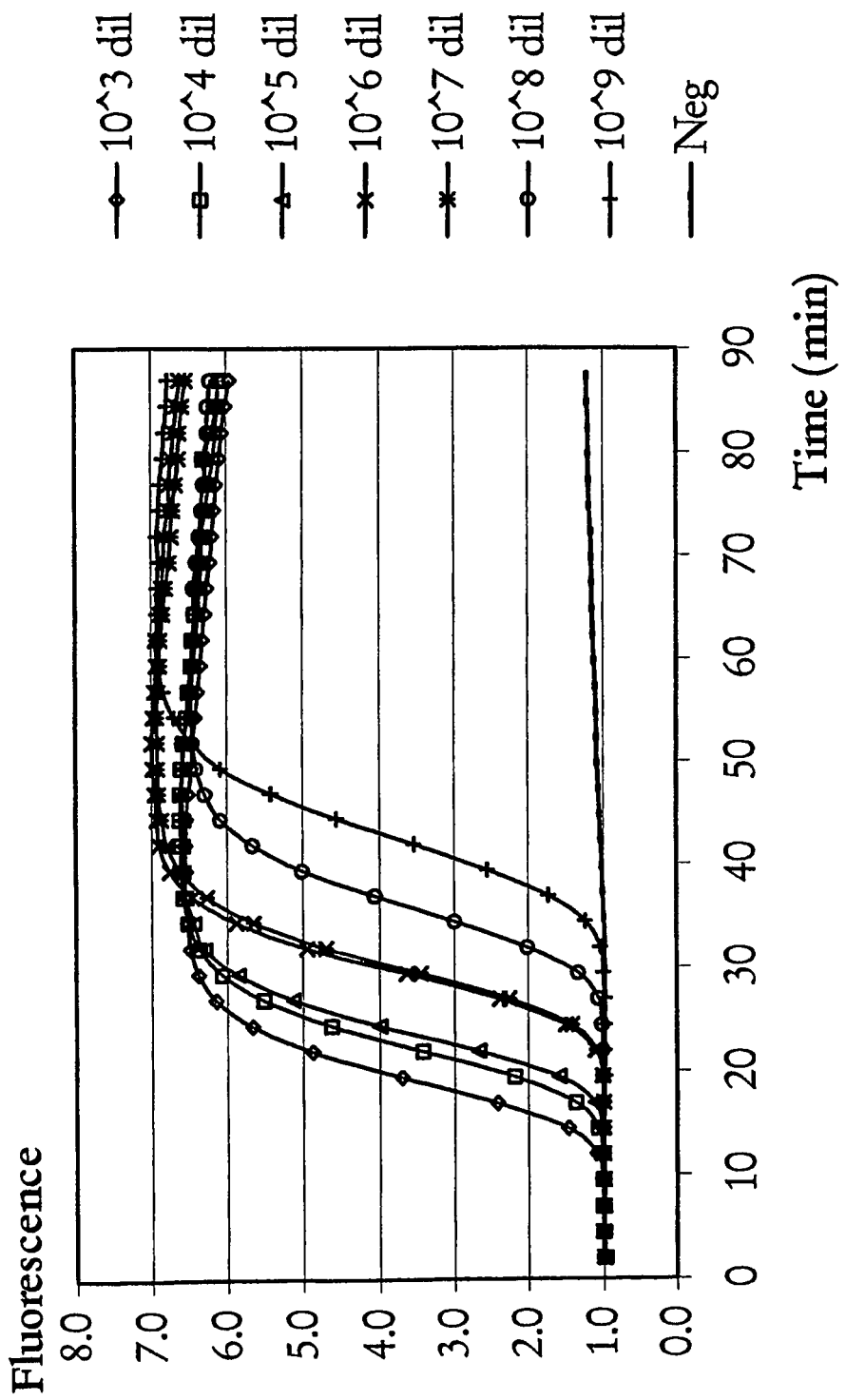
Figure 30:
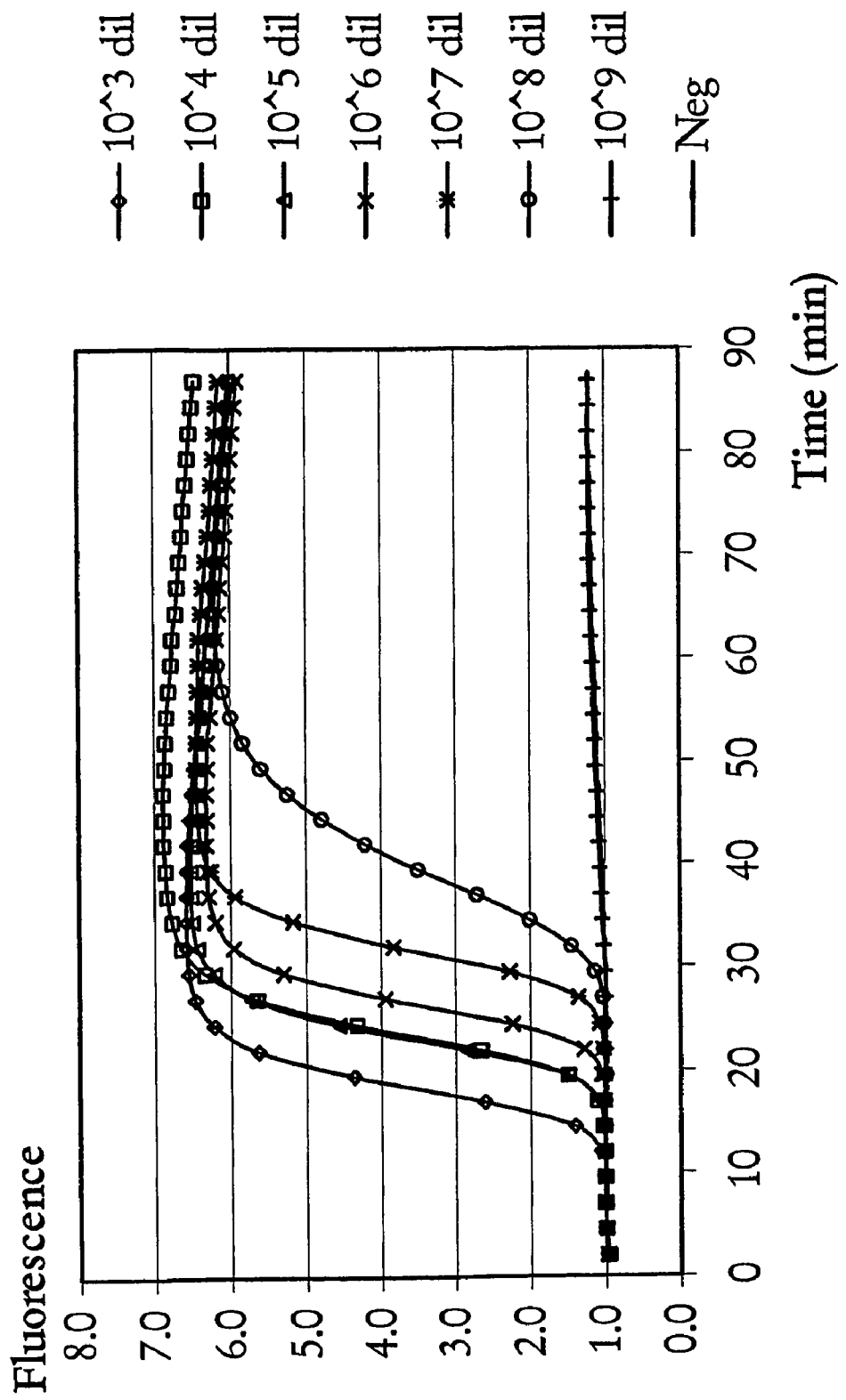
Figure 31:
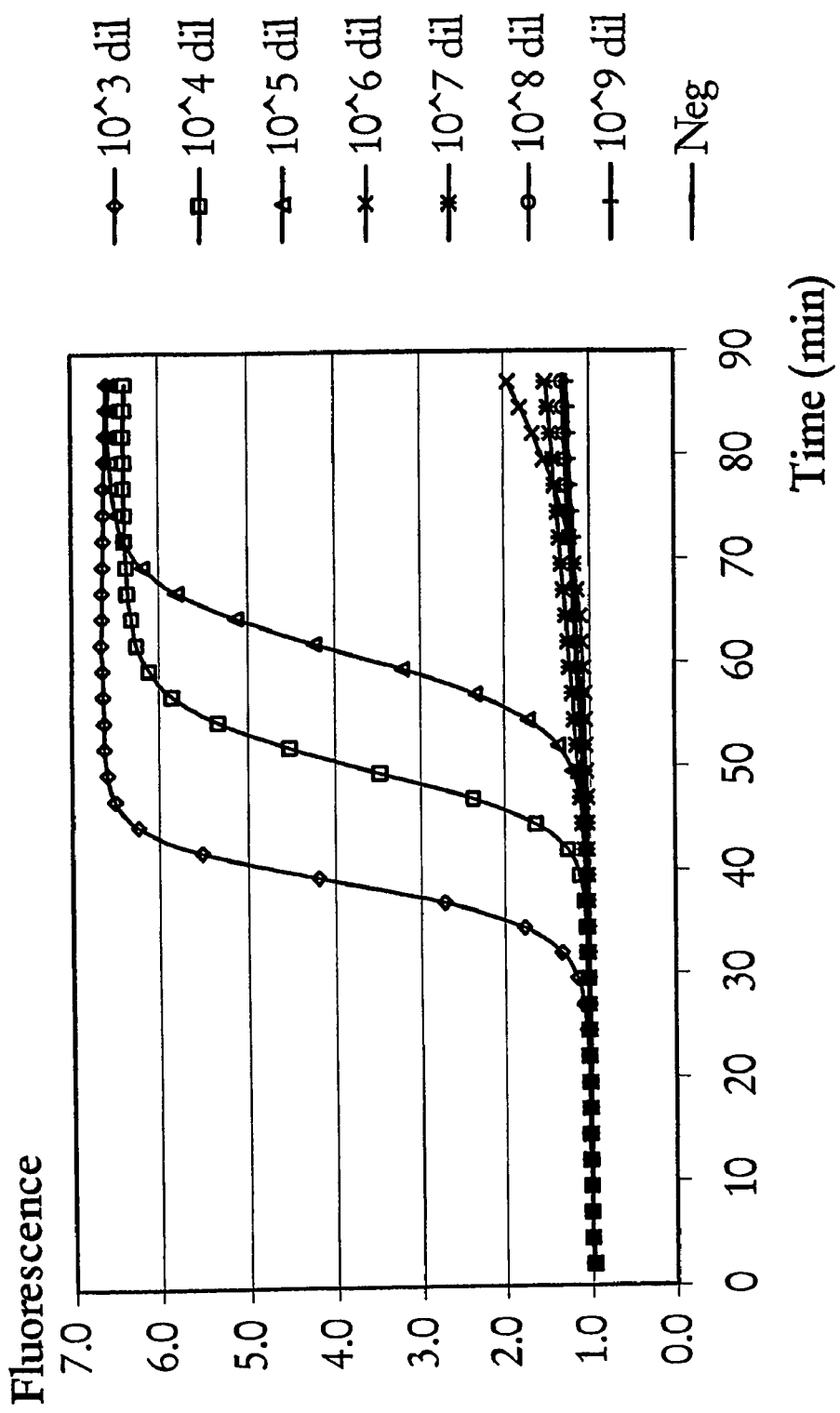
Figure 32:
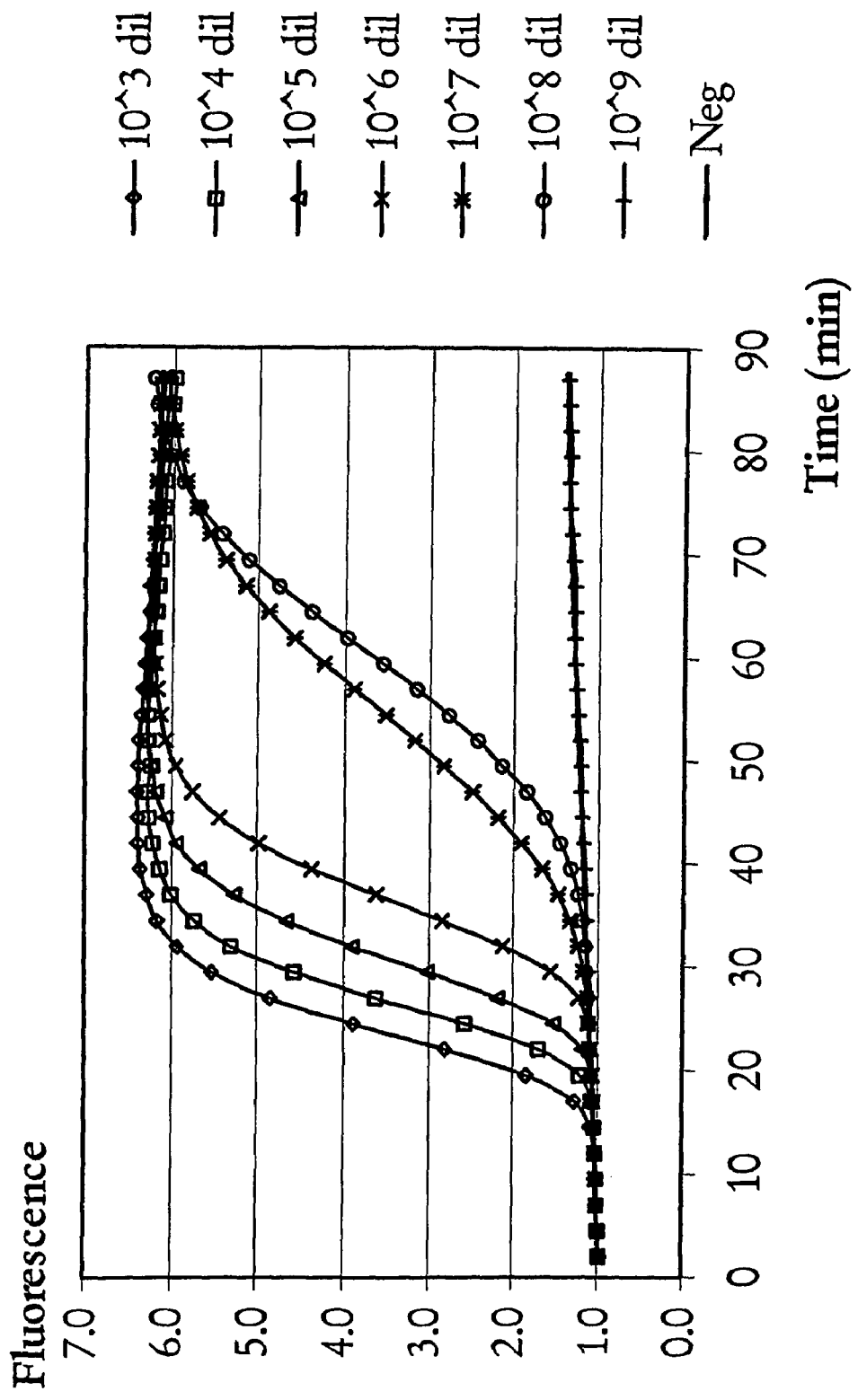
Figure 33:
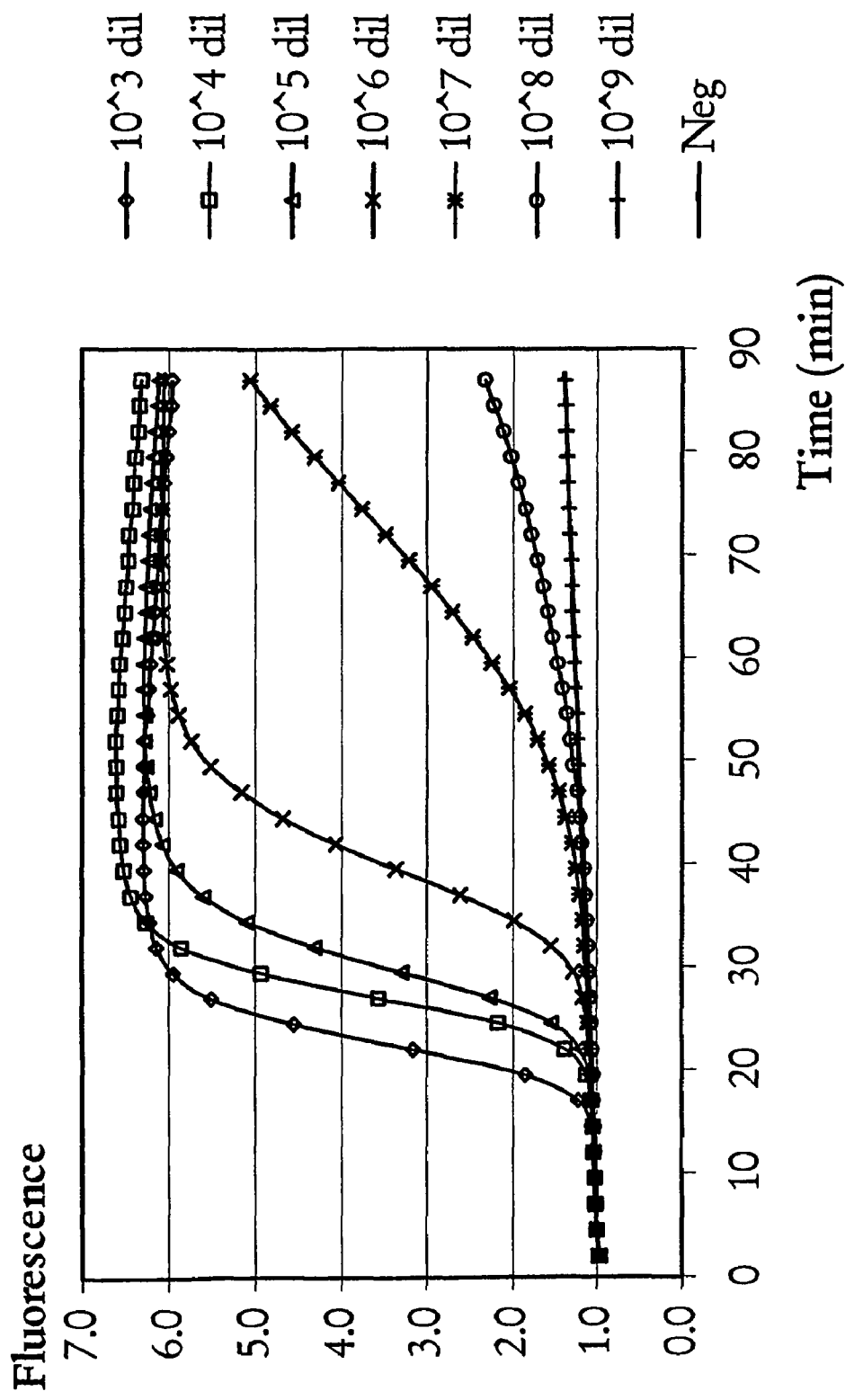
Figure 34:
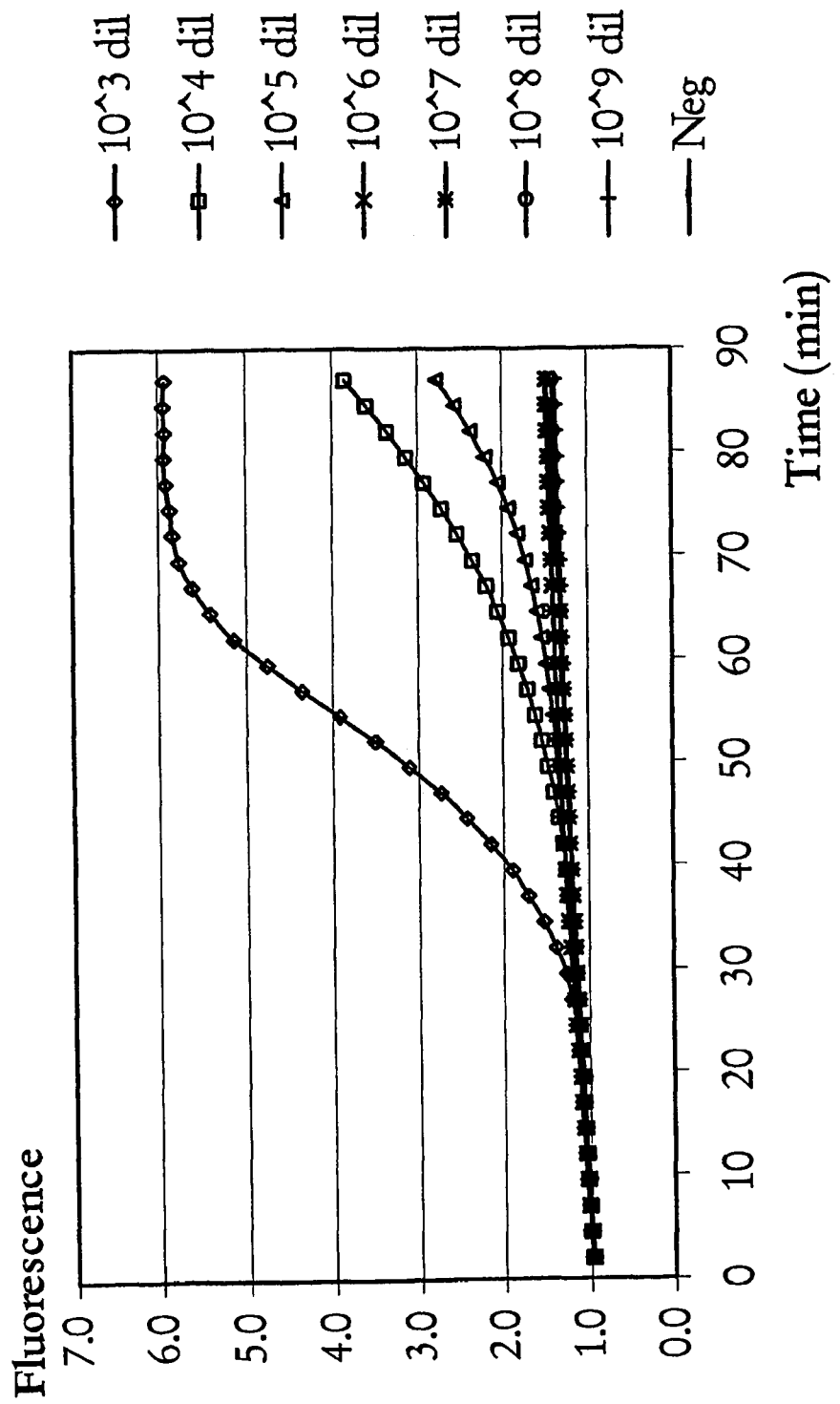
Figure 35:
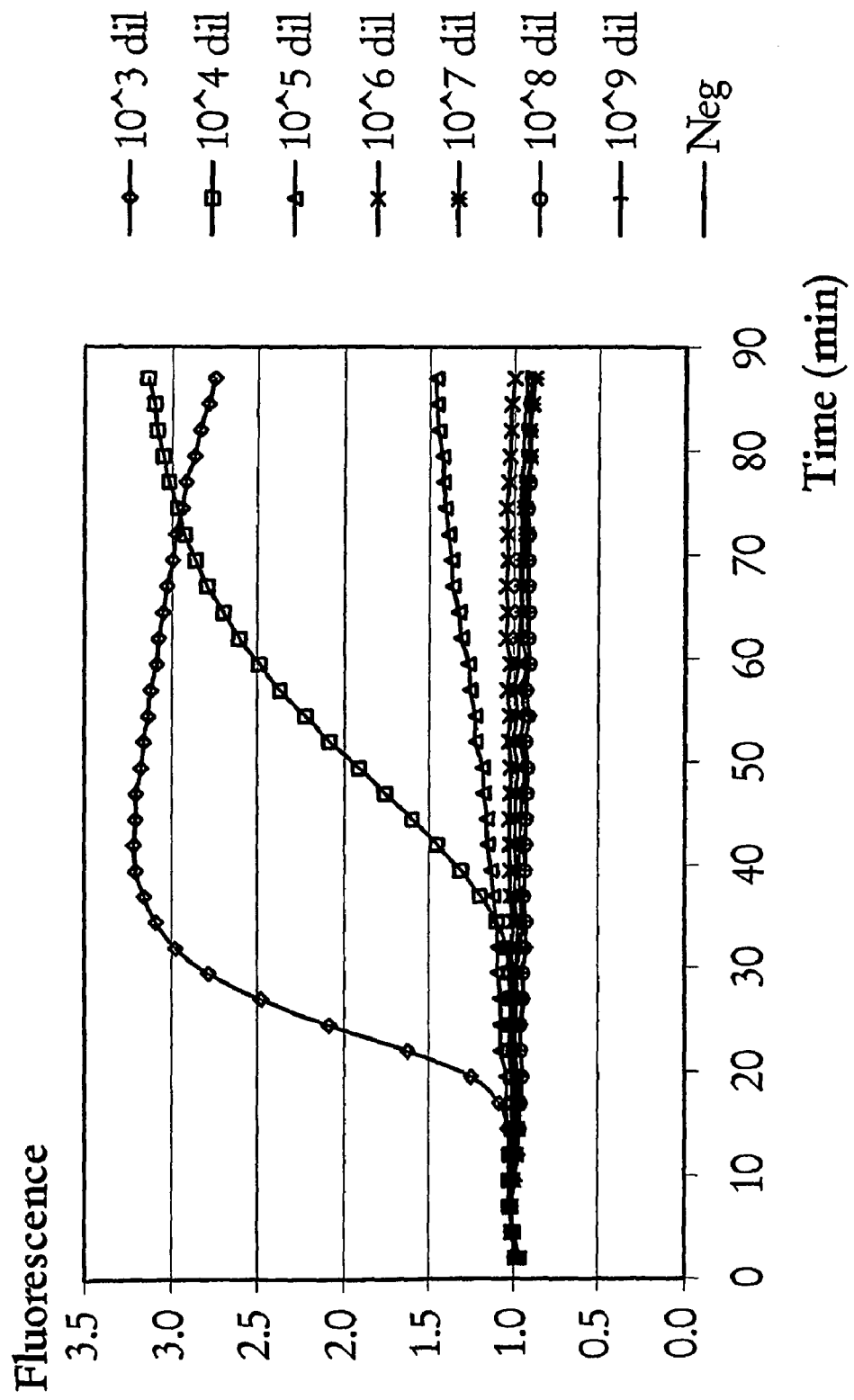
Figure 36:
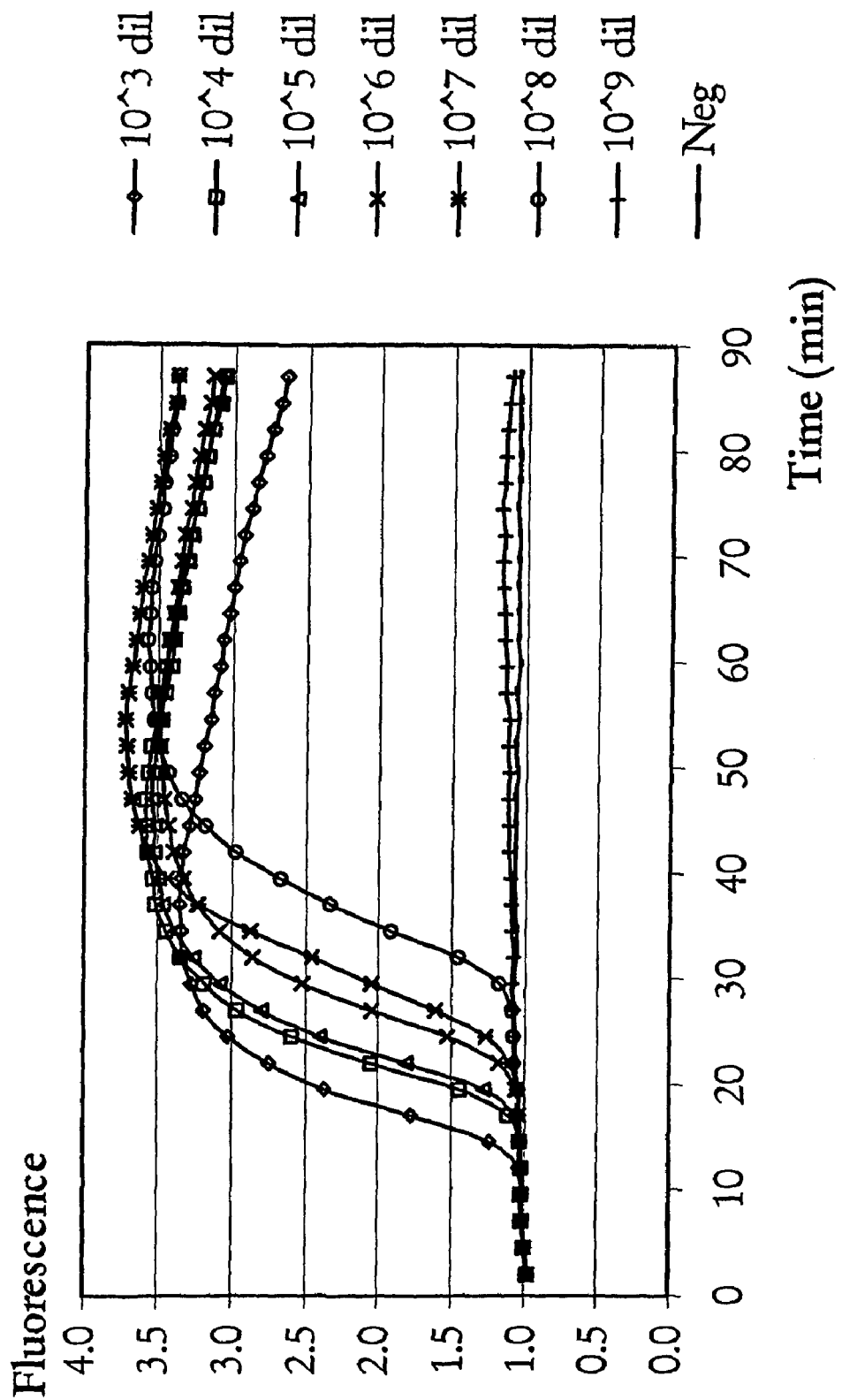
Figure 37:
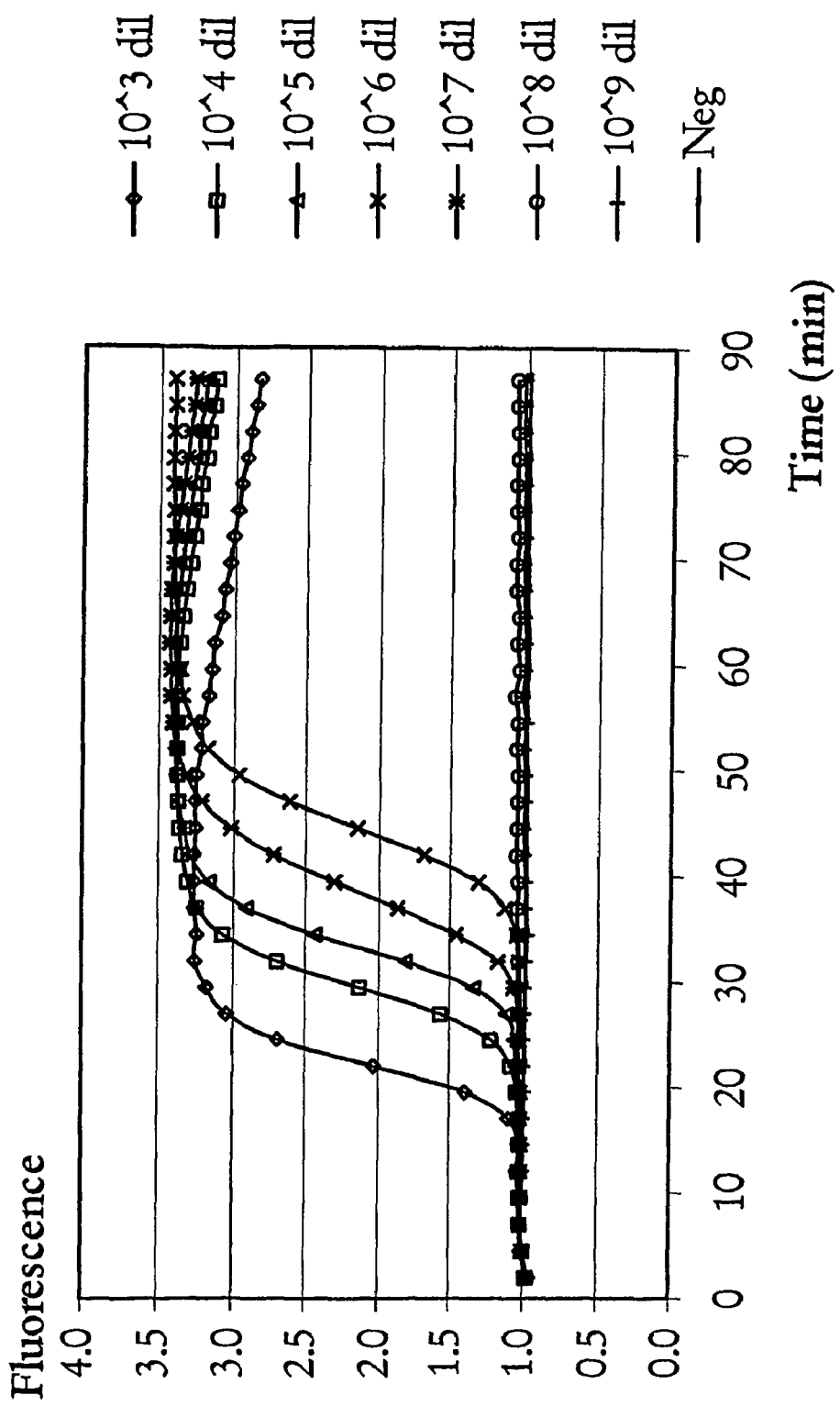
Figure 38:
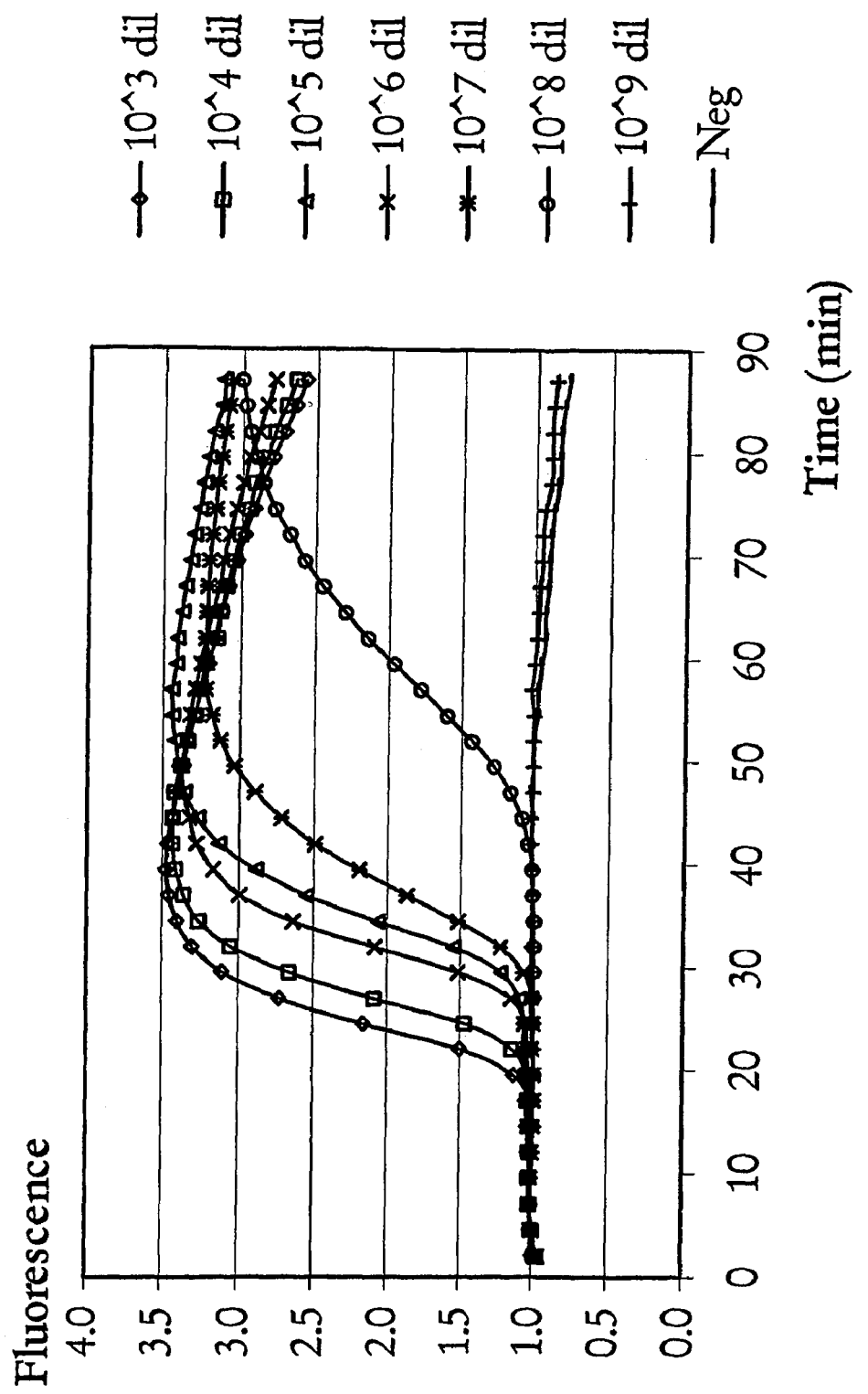
Figure 39:
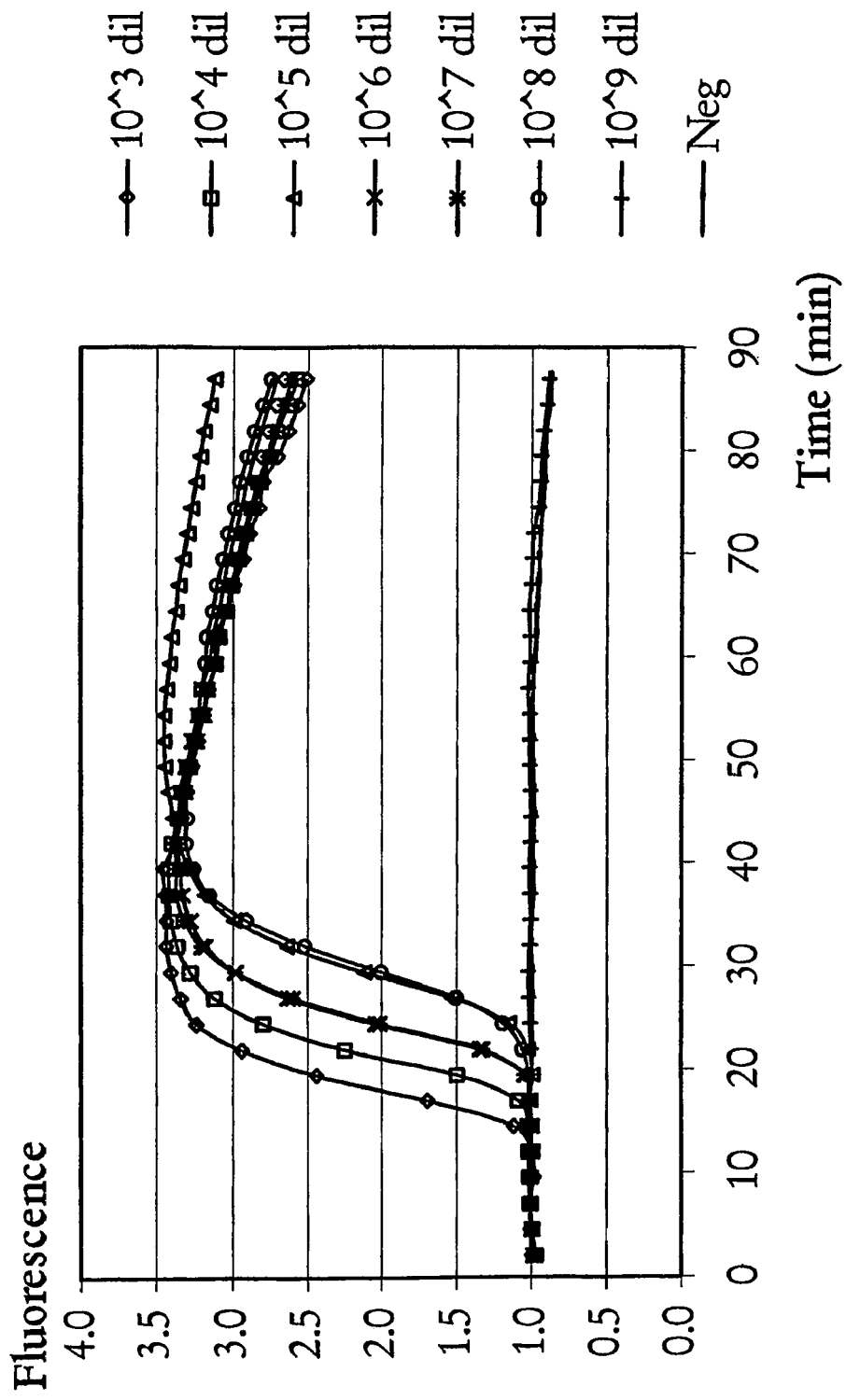

For the detection of the amplicons that can be generated with the different SARS-CoV N primers outlined in Table 5, a molecular beacon was designed for each of the two selected target regions in the N gene. The molecular beacons were designated SARS-CoV N MB-1 for the upstream (region 1) region and SARS-CoV N MB-2 for the downstream region (region 2). Correct folding of the molecular beacons was checked using mfold (17). Predicted secondary structures for SARS-CoV N MB-1 and SARS-CoV N MB-2 are shown in FIG. 12. The mfold web server ((http://www.bioinfo.rpi.edu/applications/mfold/) was used to predict the most preferred secondary structures for molecular beacons SARS-CoV N MB-1 and SARS-CoV N MB-2. Under NASBA reaction conditions [41° C.; 100 mM Na$^+$; 12 mM Mg$^{2+}$], both molecular beacons revealed the desired hairpin structure. Molecular beacon syntheses were analysed for their purity by capillary electrophoresis (CE). Molecular beacon features are summarized in Table 7.

genome sequence of SARS-CoV isolate TOR2 (GenBank Accession number AY274119).

Example 7

Selection of Primer Pair/Beacon Combination for the Amplification and Detection of SARS CoV N RNA For each of the regions chosen for amplification in the SARS-CoV Nucleocapsid gene sequence, six different primer combinations can be composed with the primers shown in Table 5. In Table 6, all combinations are summarized, together with the size of the corresponding RNA amplicons.

Initially, four SARS-CoV N primer pairs for region 1 that could be formed with P1.1, P1.2, P2.1, and P2.2 (Table 6) were tested in real-time NASBA reactions using molecular beacon SARS-CoV N MB-1 labelled with FAM (Table 7) for detection. Input RNA for these reactions was prepared from a cultured SARS-CoV virus stock (provided by Robert Koch Institute, Berlin, Germany) by extracting nucleic acid from a ten-fold dilution series containing 10,000 down to 0.1 geq of the virus. Results are shown in FIGS. 13-16. Combined with either of the P2 primers, SARS-CoV N P1.1 revealed a better performance as P1.2 (compare FIGS. 13 and 14 with FIGS. 15 and 16), although not in terms of sensitivity but with respect to kinetics and time-to-positivity values for the different dilutions.

In a follow-up experiment, the different primer combinations were compared again. Similar nucleic acid extracts were used as input material although the isolates were not prepared freshly as in the previous experiment (FIGS. 13-16), but had been stored at −70° C. for a while. Results are summarized in FIGS. 17-20. For reasons not understood, poor results were obtained for the nucleic acid extract originating from 100 geq. Nevertheless, relative comparison of the different primer combinations again identified P1.1 as the best performing P1 primer. Combination of this P1 primer with P2.2 appeared to be the most favourable primer pair because SARS-CoV N P1.1/P2.2 was the combination capable of most efficiently detecting the nucleic acid extract resulting from 1 geq and to reveal a positive albeit low signal for the "100 geq" nucleic

TABLE 7

Molecular beacon probes for the detection in real-time of two regions located in the Nucleocapsid gene of SARS-CoV.

| Description | Sequence (SEQ ID number) | Length | Genome Location | Purity (CE) |
|---|---|---|---|---|
| SARS-CoV N MB-1 | 5'-(6-FAM)-ccatgggCTACTACCGAAGAGCTACCCG ACGAcccatgg-(DabSyl)-3' (label + SEQ ID22 + quencher) | 39 nt | 28,377-28,401 | 88.2% |
| SARS-CoV N MB-2 | 5'-(6-FAM)-ccatggACCAAGACCTAATCAGACAAccatgg-(DabSyl)-3' (label + SEQ ID 30 + quencher) | 32 nt | 28,985-29,004 | 75.5% |

For the molecular beacons (SARS-CoV N MB-1 and MB-2) the arm sequences at the 5'-end and at the 3'-end are depicted in small characters. Fluorophore 6-FAM is covalently linked to the 5'-end of the molecular beacons; the quenching moiety DabSyl is covalently linked to the 3'-end of the molecular beacons. Coordinates for the location of the molecular beacon probes are derived from the complete acid extract (FIG. 18) that unexpectedly tested negative for the other primer combinations.

In a comparable way as for region 1, four primer combinations for region 2 that can be compiled from primers SARS-CoV N P1.3, P1.4, P2.3, and P2.4 (Table 6) were analysed, now using FAM-labelled molecular beacon SARS-CoV N MB-2 (Table 7) for real-time detection. Results for freshly prepared nucleic acid extracts are shown in FIGS. 21-24. In contrast to the primer pairs for region 1 in which a P1 primer was the dominating factor, for region 2 a P2 primer, viz. SARS-CoV N P2.4, appeared to be the crucial primer. It revealed a much better performance as the other P2 primer (compare FIGS. 21 and 23, 22 and 24), while combination with either SARS-CoV N P1.3 or P1.4 did not make too much of a difference (see FIGS. 22 and 24). Although kinetics for the "10 geq" nucleic acid extract for SARS-CoV N P1.3/P2.4 were slower as for the SARS-CoV N P1.4/P2.4 primer combination, the low but evidently positive signal for the next dilution, i.e. the "1 geq" nucleic acid extract, (FIG. 22) pleads in favour of the former primer combination.

Analysis of stored nucleic acid extracts containing genomic viral RNA with the region 2 primer combinations confirmed the results as obtained for the fresh specimens. As can be seen from FIGS. 25-28, again P2.4 appeared to be the key primer. Combination with either P1.3 or P1.4 revealed similar results although the nucleic acid extract resulting from 1 geq was missed by the SARS-CoV N P1.3/P2.4 primer pair whereas the next dilution in line was well detected. With all four primer combinations, poor results were obtained for the "100 geq" nucleic acid extract, confirming the poor results for this isolate with the region 1 primer combinations (FIGS. 17-20).

In conclusion, this first endeavour to come and get to a well performing primer pair for the detection of SARS-CoV subgenomic mRNA encoding the nucleocapsid protein revealed SARS-CoV N P1.1/P2.2 in region 1 and either SARS-CoV N P1.3/P2.4 or SARS-CoV N P1.4/P2.4 in region 2 as the most likely candidates. Overall comparison of the three primer combinations identified SARS-CoV N P1.1/P2.2 (region 1) in combination with SARS-CoV N MB-1 as the most favourable primer pair, mainly based on the shape of the fluorescence curves and the absolute fluorescence signals that could be obtained with this primer/beacon mixture. Therefore, this primer/beacon mixture was selected as SARS-CoV N-1 for further evaluation.

In an attempt to further improve the sensitivity of SARS-CoV N mRNA detection, an additional P2 primer was designed for both regions, viz. SARS-CoV N P2.5 for region 1 and SARS-CoV N P2.6 for region 2 (Table 5). In either case, this new P2 primer was located closer to the P1 primer resulting in a smaller amplicon size as obtained for the initial primer combinations (Table 6).

The six SARS-CoV N primer pairs that could now be formed for each of the two regions (Table 6) were tested in real-time NASBA reactions using the FAM-labelled SARS-CoV N molecular beacon designed for each of the regions (Table 7) for detection. Input RNA for these reactions was prepared from a cultured SARS-CoV virus stock (provided by Erasmus Medical Center, Rotterdam, The Netherlands). Nucleic acid was extracted from a 100-fold dilution of the original virus stock. From the resulting nucleic acid extract, a ten-fold dilution series was prepared containing nucleic acid as if extracted from $10^3$-fold down to $10^9$-fold dilutions of the original virus stock.

Results for the SARS-CoV N primer pairs in region 1 are shown in FIGS. 29-34. Remarkably, primer combinations containing the new SARS-CoV N P2.5 primer (FIGS. 31 and 34) demonstrated a significantly lower sensitivity as the other primer pairs instead of an anticipated better performance. This was somewhat unexpected since this P2 primer revealed shorter amplicons (102 nts and 134 nts in combination with P1.1 or P1.2, respectively; see also Table 6) and, therefore, was expected to result in more efficient amplification. Comparison of the remaining primer combinations confirmed the already observed superiority of SARS-CoV N P1.1 over SARS-CoV N P1.2. However, in contrast to earlier observations (FIGS. 13-20), now SARS-CoV N P2.1 appeared to be superior over SARS-CoV N P2.2, which again would not be logical in terms of amplicon length (203 nts versus 139 nts for P2.1 and P2.2, respectively; see also Table 6). The overall conclusion of this comparison is twofold:

for each of the two P1 primers: the larger the amplicon size, the better the performance of the underlying primer combination; and P1.1 revealed a better performance as P1.2.

Figure 40:
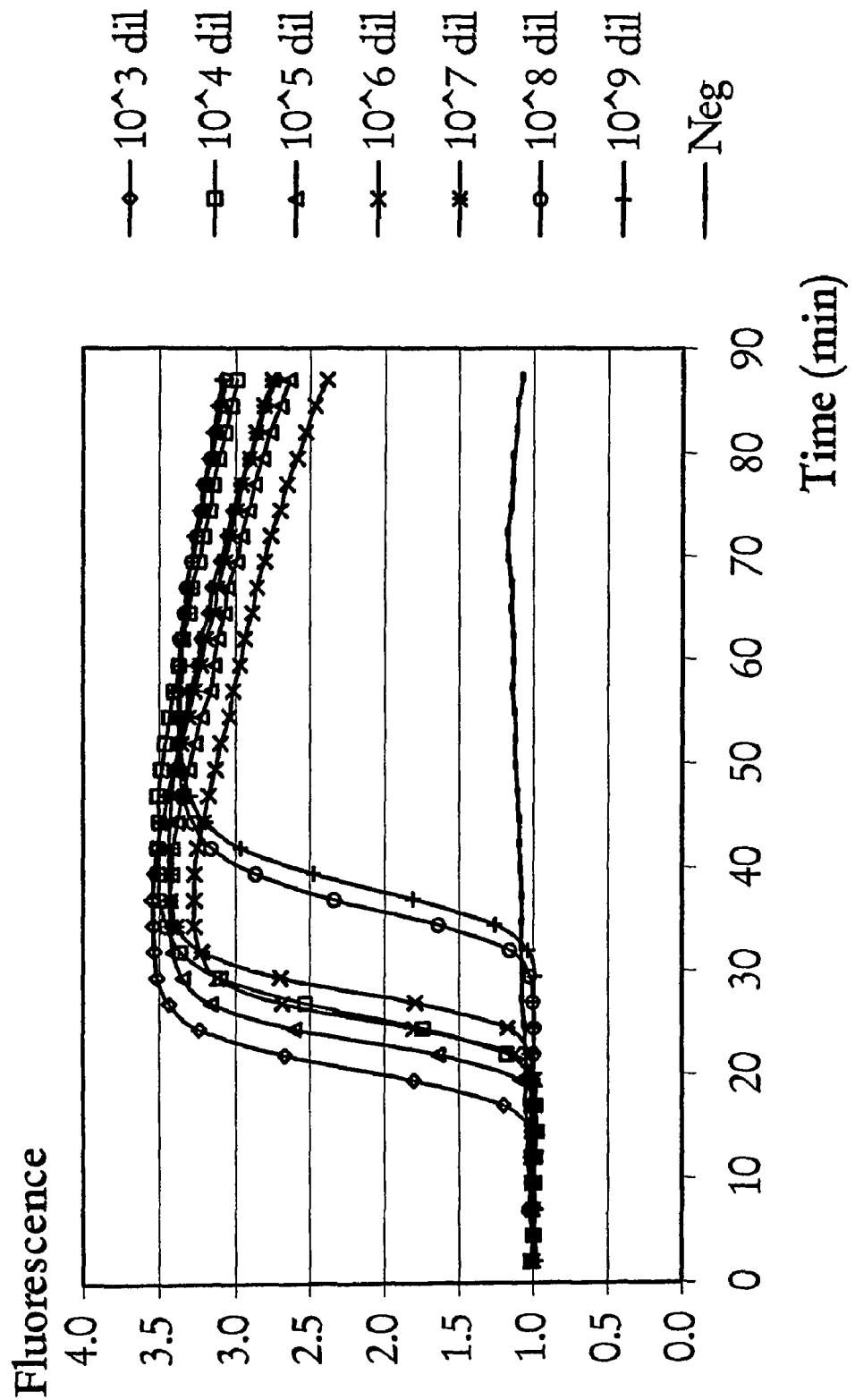

Results for region 2 including the additional P2.6 primer are shown in FIGS. 35-40. When combined with SARS-CoV N P1.3, the new P2 primer did not reveal the anticipated higher sensitivity (FIG. 37), but instead showed a somewhat poorer performance as the SARS-CoV N P1.3/P2.4 primer pair both in terms of sensitivity and in time-to-positivity values for the individual dilutions. However, in combination with the other P1 primer chosen in this region and resulting in primer pair SARS-CoV N P1.4/P2.6, sensitivity indeed increased, reflected by the result obtained for the nucleic acid extract obtained for the $10^9$ dilution of the virus stock that only tested positive with this region 2 primer pair (FIG. 40).

Next to SARS-CoV N P1.4/P2.6 and in line with previous observations (see FIGS. 21-28), also SARS-CoV N P1.3/P2.4 (FIG. 36) and SARS-CoV N P1.4/P2.4 (FIG. 39) again were identified as better performing primer combinations in this region and again these primer combinations mutually were nearly indistinguishable.

Third Set of Examples Related to RNA Encompassing the 3'-Non Coding Region (3'-NCR):

Example 8

SARS-CoV 3'-NCR Primers Design

The subgenomic mRNA transcripts of SARS-CoV form a 3'-co-terminal nested set with the viral genome and, consequently, have a common 3'-end sequence. Excluding the poly (A)-tail, this 3'-untranslated or non-coding region (3'-NCR) is 339 nucleotides in length and encompasses genomic positions 29,389-29,727.

Primers were designed for the amplification of fragments of the 3'-NCR between genomic nucleotides 29,447-29,713. Sequences, polarity, and genomic locations of these SARS-CoV 3'-NCR primers are shown in Table 8.

TABLE 8

Primers for the amplification in real-time of a region
located in the 3'-untranslated sequence of SARS-CoV.

| Description | Sequence (SEQ ID number) | Length | Genome Location | Purity (CE) |
|---|---|---|---|---|
| SARS-CoV 3'-NCR P1.5 | 5'-aattctaatacgactcactatagggGGGCTCTT CCATATA GGCA-3' | 44 nt | 29,642-29,660 | 83.3% |

TABLE 8-continued

| Primers for the amplification in real-time of a region located in the 3'-untranslated sequence of SARS-CoV. | | | | |
|---|---|---|---|---|
| Description | Sequence (SEQ ID number) | Length | Genome Location | Purity (CE) |
| | (T7 + SEQ ID 32) | | | |
| SARS-CoV 3'-NCR P1.6 | 5'-aattctaatacgactcactatagggAAGCTATT AAAATC ACATGGGGA-3' (T7 + SEQ ID 33) | 48 nt | 29,691-29,713 | 85.6% |
| SARS-CoV 3'-NCR P2.5 | 5'-TACGATACATAGTCTACTCTTGT-3' (SEQ ID 35) | 23 nt | 29,447-29,469 | 91.7% |
| SARS-CoV 3'-NCR P2.6 | 5'-TAACTAAACAGCACAAGTAGGT-3' (SEQ ID 36) | 22 nt | 29,486-29,507 | 86.5% |
| SARS-CoV 3'-NCR P2.7 | 5'-TAGCAATCTTTAATCAATGT-3' (SEQ ID 37) | 20 nt | 29,529-29,548 | 91.3% |

For the P1 primers (SARS-CoV 3'-NCR P1.5 and P1.6) the T7 Polymerase promoter sequence is depicted in small characters. Coordinates for the location of the primers are derived from the complete genome sequence of SARS-CoV isolate TOR2 (GenBank Accession number AY274119).

Two P1 primers (SARS-CoV 3'-NCR P1.5 and P1.6) and three P2 primers (SARS-CoV 3'-NCR P2.5, P2.6, and P2.7) were derived from the viral genome sequence and enabled the composition of six different primer pairs (Table 9).

TABLE 9

| SARS-CoV 3'-NCR primer combinations. | | |
|---|---|---|
| Primer Combination | Amplicon Size | Genome Location |
| SARS-CoV 3'-NCR P1.5/P2.5 | 214 nt | 29,447-29,660 |
| SARS-CoV 3'-NCR P1.5/P2.6 | 175 nt | 29,486-29,660 |
| SARS-CoV 3'-NCR P1.5/P2.7 | 132 nt | 29,529-29,660 |
| SARS-CoV 3'-NCR P1.6/P2.5 | 267 nt | 29,447-29,713 |

TABLE 9-continued

| SARS-CoV 3'-NCR primer combinations. | | |
|---|---|---|
| Primer Combination | Amplicon Size | Genome Location |
| SARS-CoV 3'-NCR P1.6/P2.6 | 228 nt | 29,486-29,713 |
| SARS-CoV 3'-NCR P1.6/P2.7 | 185 nt | 29,529-29,713 |

Primer pairs that can be formed with the SARS-CoV 3'-NCR primers (Table 8) are given together with the size and genome location of the resulting amplicons.

Example 9

SARS-CoV 3'-NCR Molecular Beacon Design

Molecular beacon SARS-CoV 3'-NCR MB-1 was designed as shown in Table 10 for the detection of amplicons that can be generated with the SARS-CoV 3'-NCR primers outlined in Table 8.

TABLE 10

| Molecular beacon for the detection in real-time of amplicons generated from a region located in the 3'-untranslated sequence of SARS-CoV. | | | | |
|---|---|---|---|---|
| Description | Sequence | Length | Genome Location | Purity (CE) |
| SARS-CoV 3'-NCR MB-1 | 5'-(6-FAM)-ccatgcGCCACCACATTTTCATCGAG gcatgg-(DabSyl)-3' (label + SEQ ID 47 + quencher) | 32 nt | 29,574-29,595 | 84.6% |

For the molecular beacon (SARS-CoV 3'-NCR MB-1) the arm sequences at the 5'-end and at the 3'-end are depicted in small characters. Fluorophore 6-FAM is covalently linked to the 5'-end of the molecular beacon; the quenching moiety DabSyl is covalently linked to the 3'-end of the molecular beacon. Coordinates for the location of the molecular beacon probe are derived from the complete genome sequence of SARS-CoV isolate TOR2 (GenBank Accession number AY274119).

Figure 41:
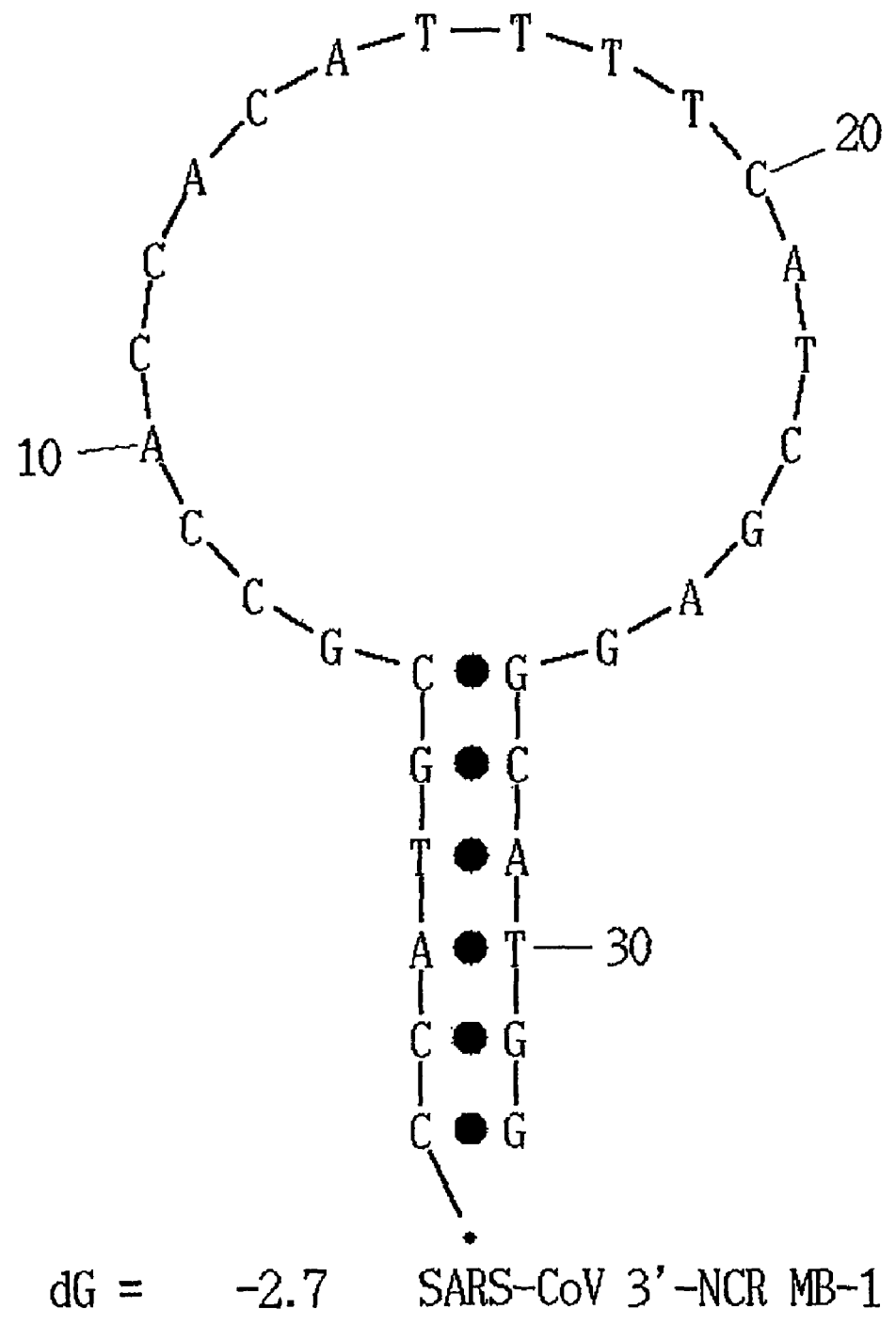

Correct folding of the molecular beacon was checked using mfold (17). The secondary structure as predicted for SARS-CoV 3'-NCR MB-1 is shown in FIG. 41. Under NASBA reaction conditions [41° C.; 100 mM Na$^+$; 12 mM Mg$^{2+}$], the molecular beacon revealed the desired hairpin structure.

Synthesis of the molecular beacon was analysed by capillary electrophoresis (CE) and revealed a purity of about 84.6% (Table 10).

Example 10

Selection of Primer Pair/Beacon Combination for the Amplification and Detection of SARS-CoV 3'-NCR Six different primer combinations could be formed with the SARS-CoV 3'-NCR primers shown in Table 8. Primer combinations are depicted in Table 9 together with the size of the resulting RNA amplicons.

The different SARS-CoV 3'-NCR primer pairs were combined with the FAM-labelled SARS-CoV 3'-NCR molecular beacon (Table 10) and tested in real-time NASBA reactions. Input RNA for these reactions was prepared from a cultured SARS-CoV virus stock (provided by Robert Koch Institute, Berlin, Germany). From a nucleic acid extract prepared from 1000 geq of the virus, a ten-fold dilution series in water was prepared. This dilution series contained nucleic acid levels as if extracted from 100 geq down to 0.01 geq.

Figure 42:
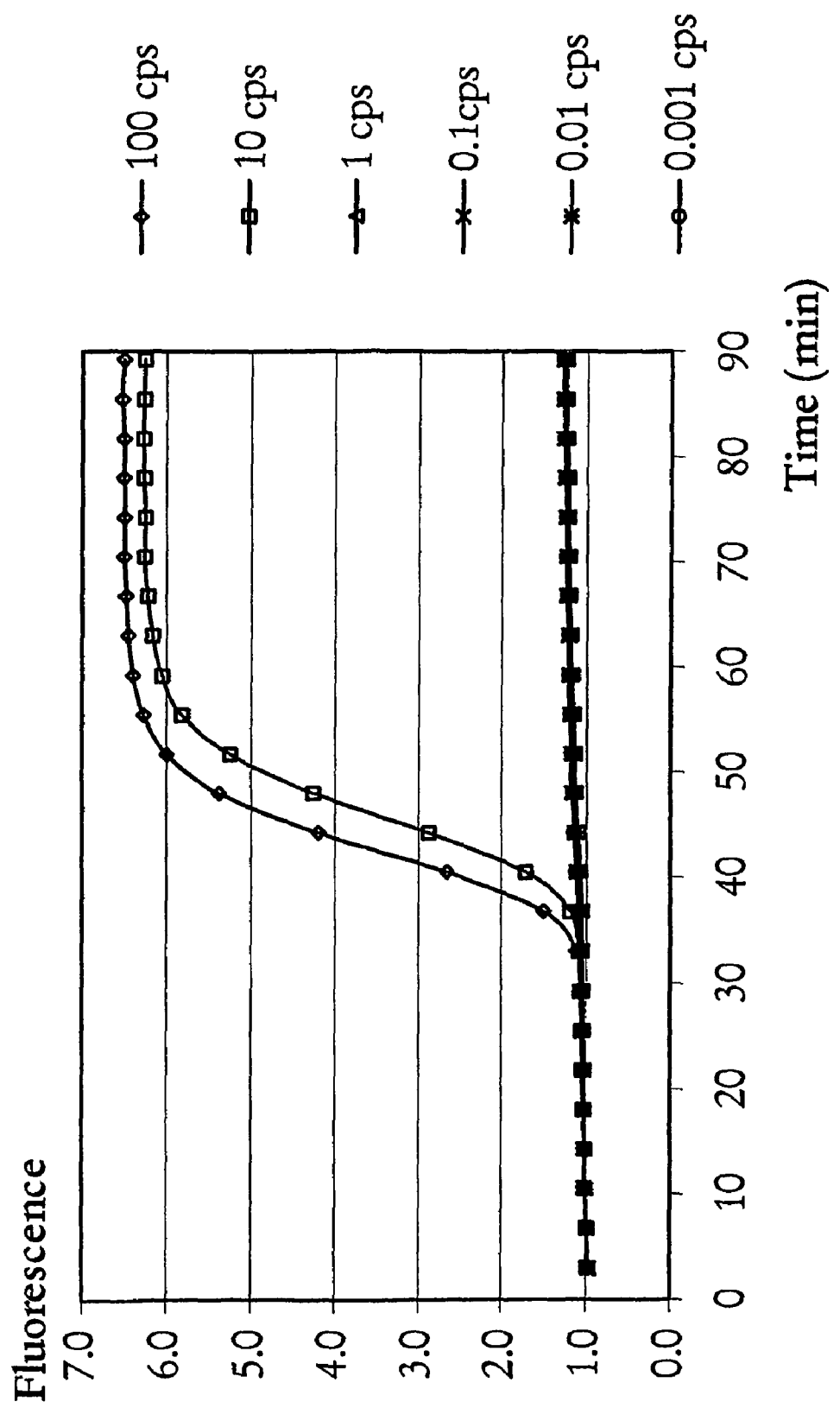
Figure 43:
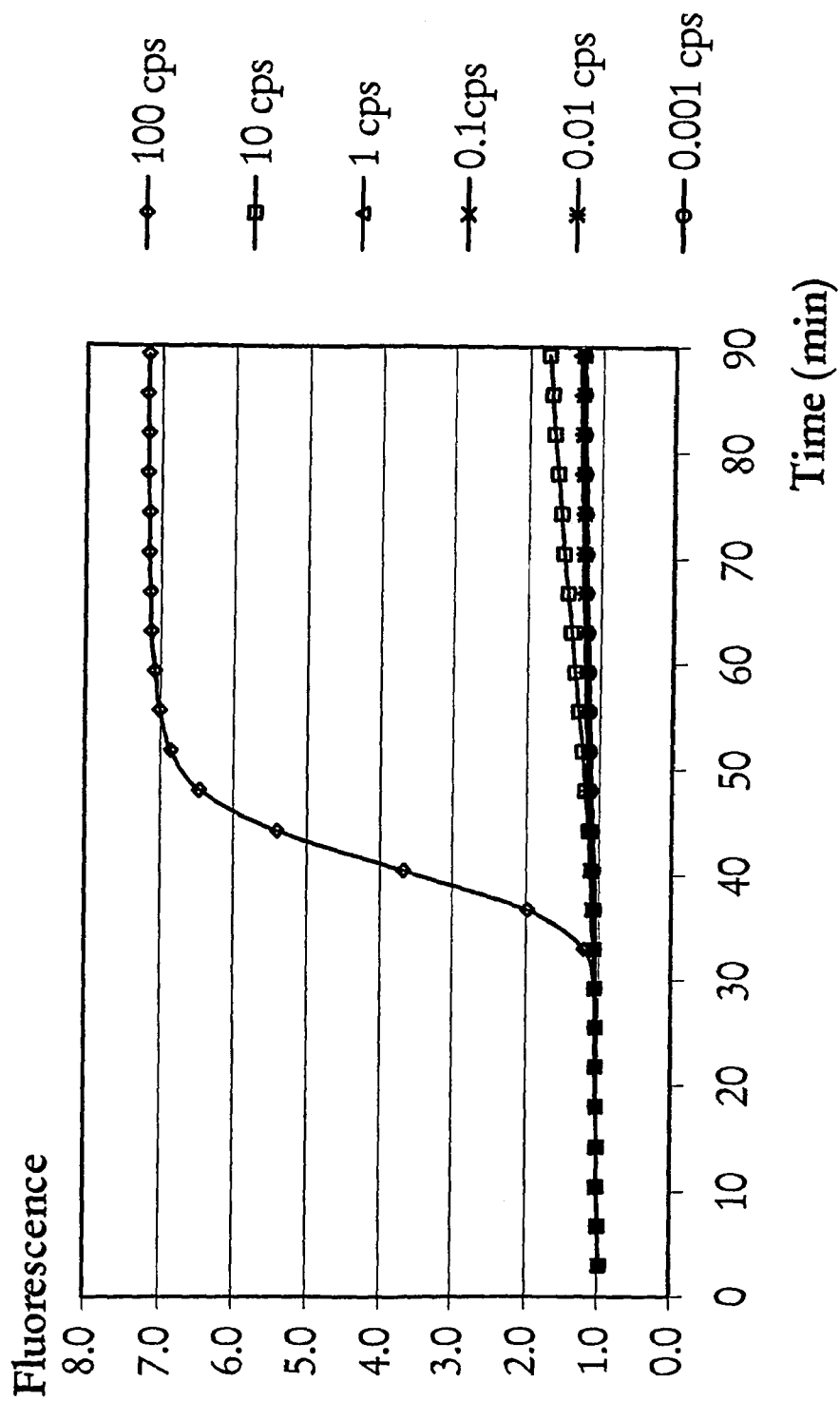
Figure 44:
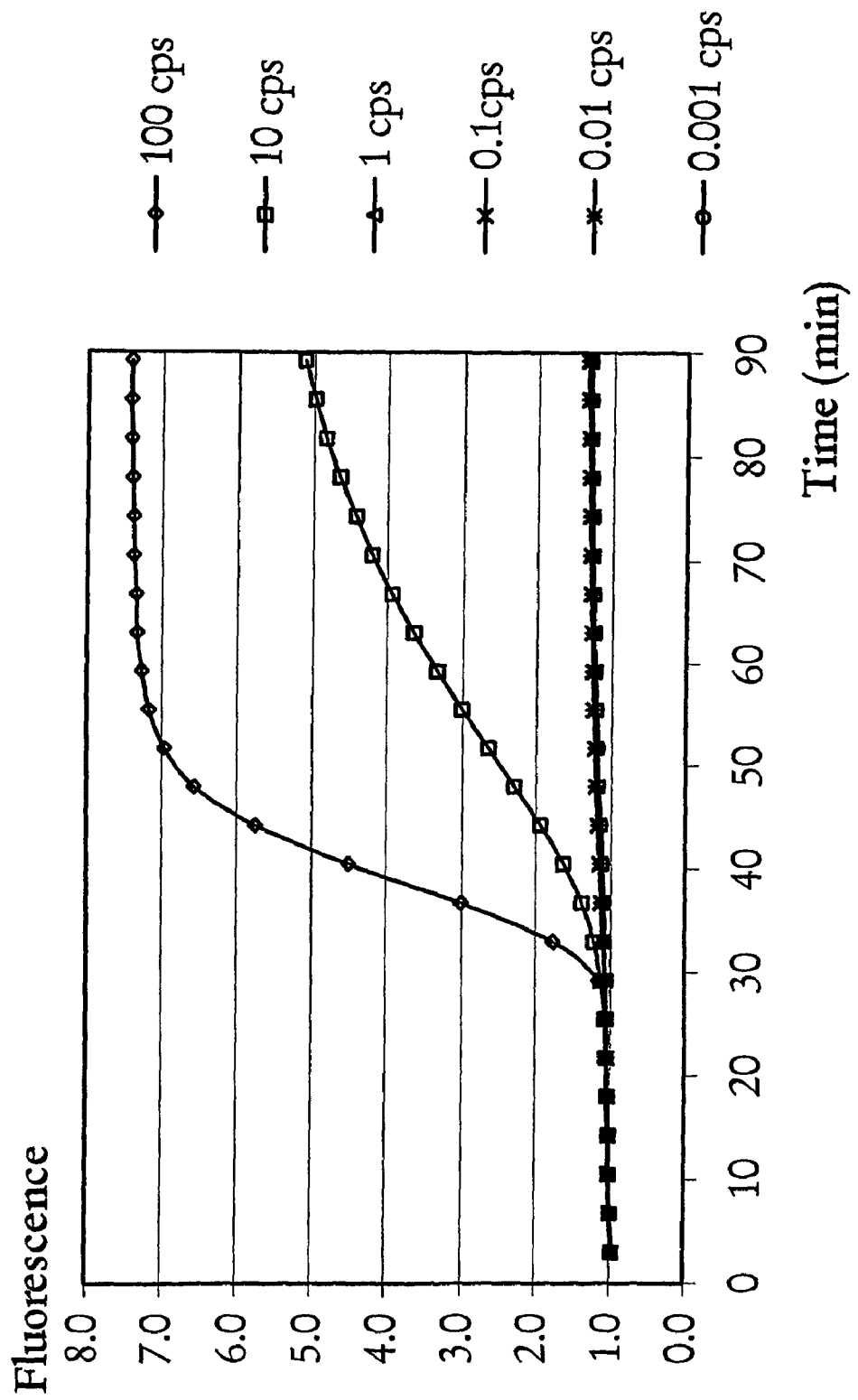
Figure 45:
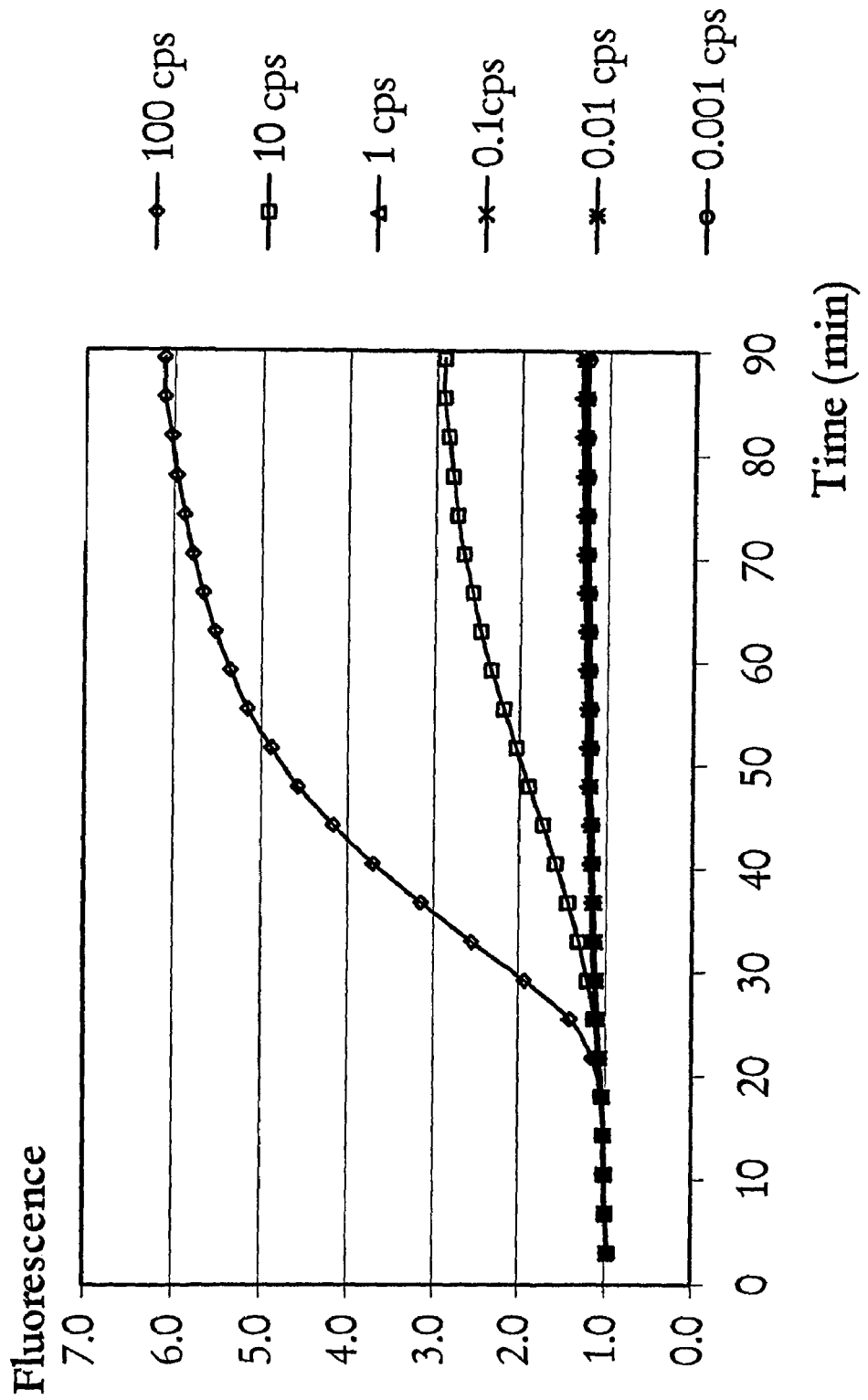
Figure 46:
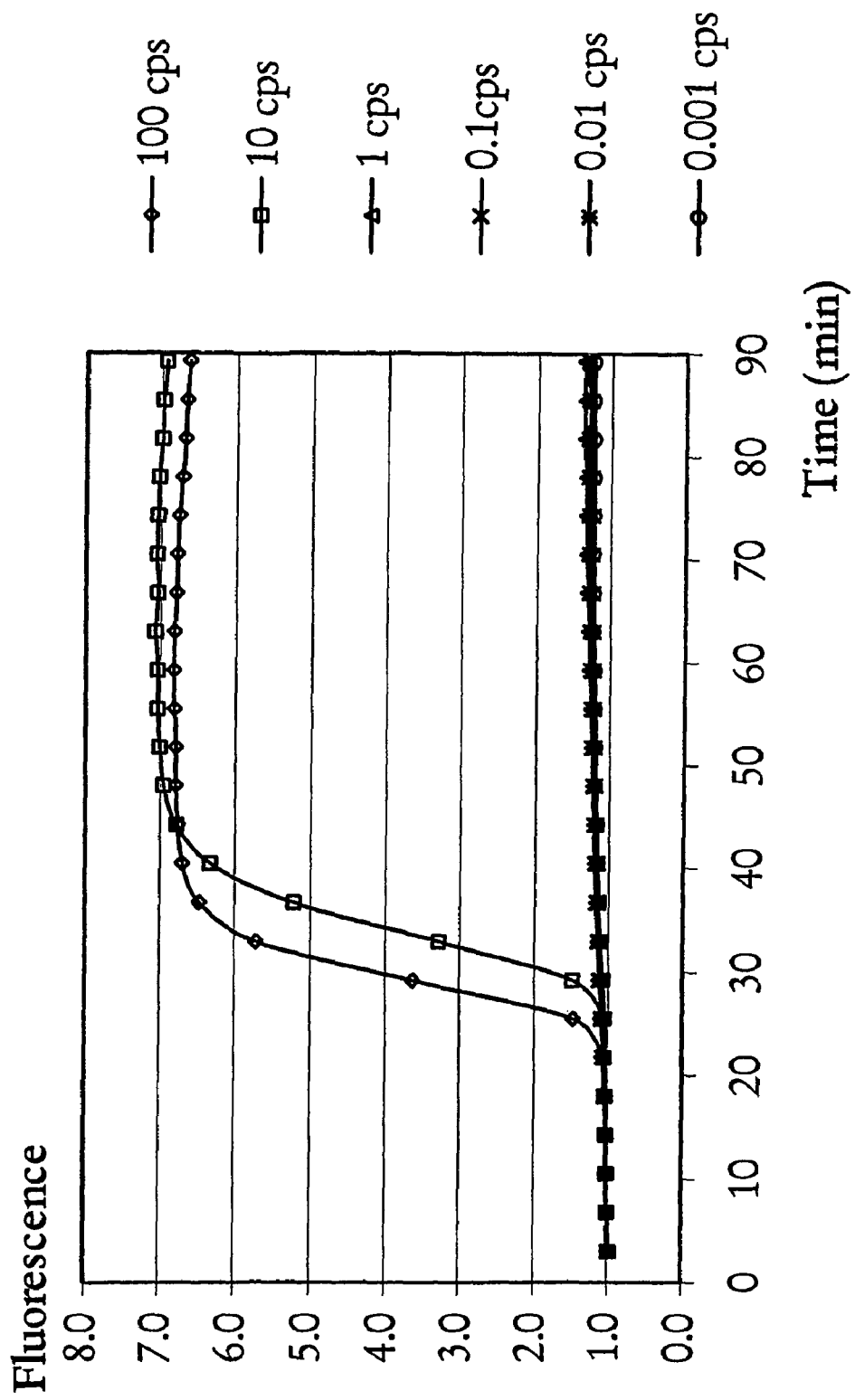
Figure 47:
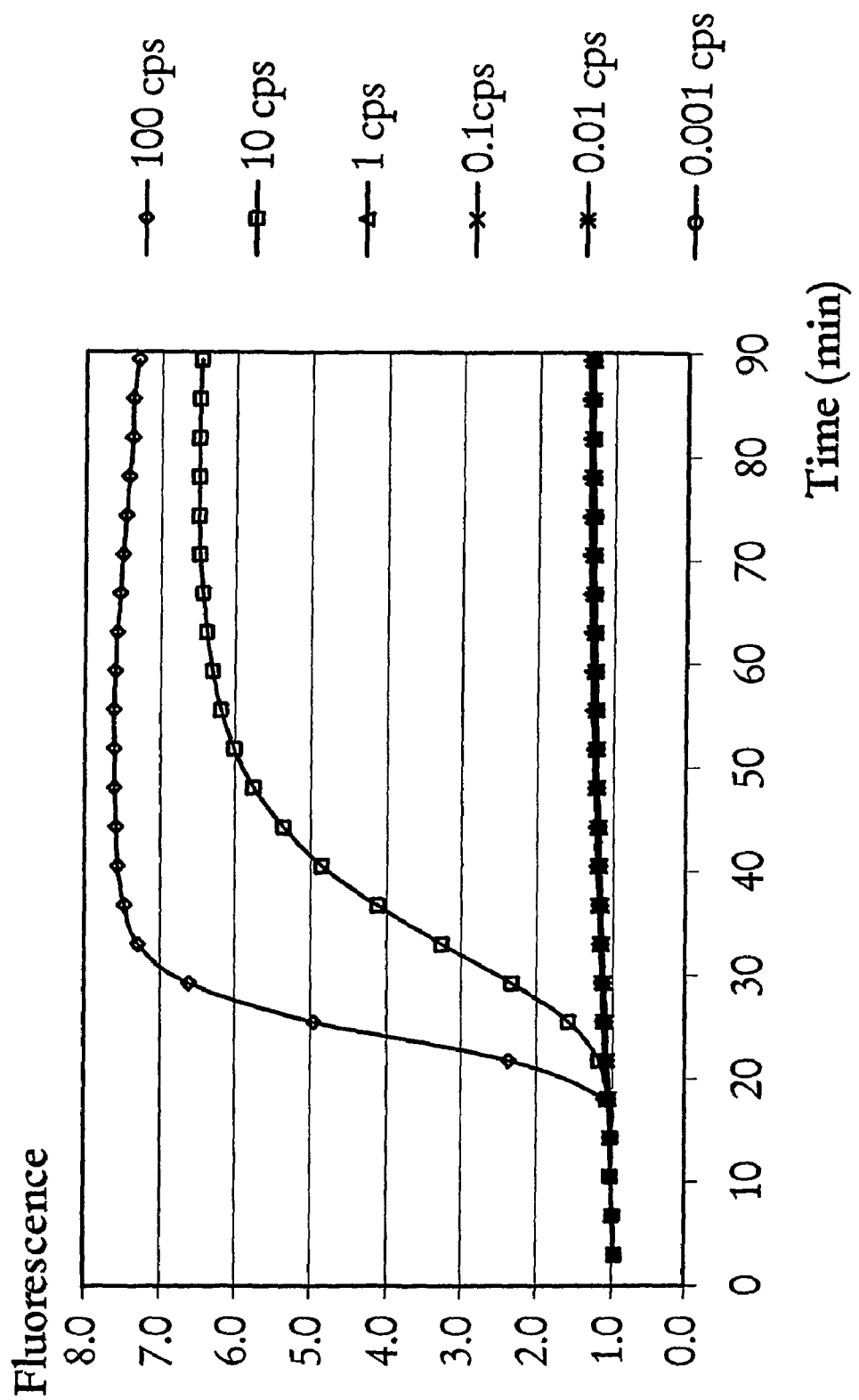
Figure 48:
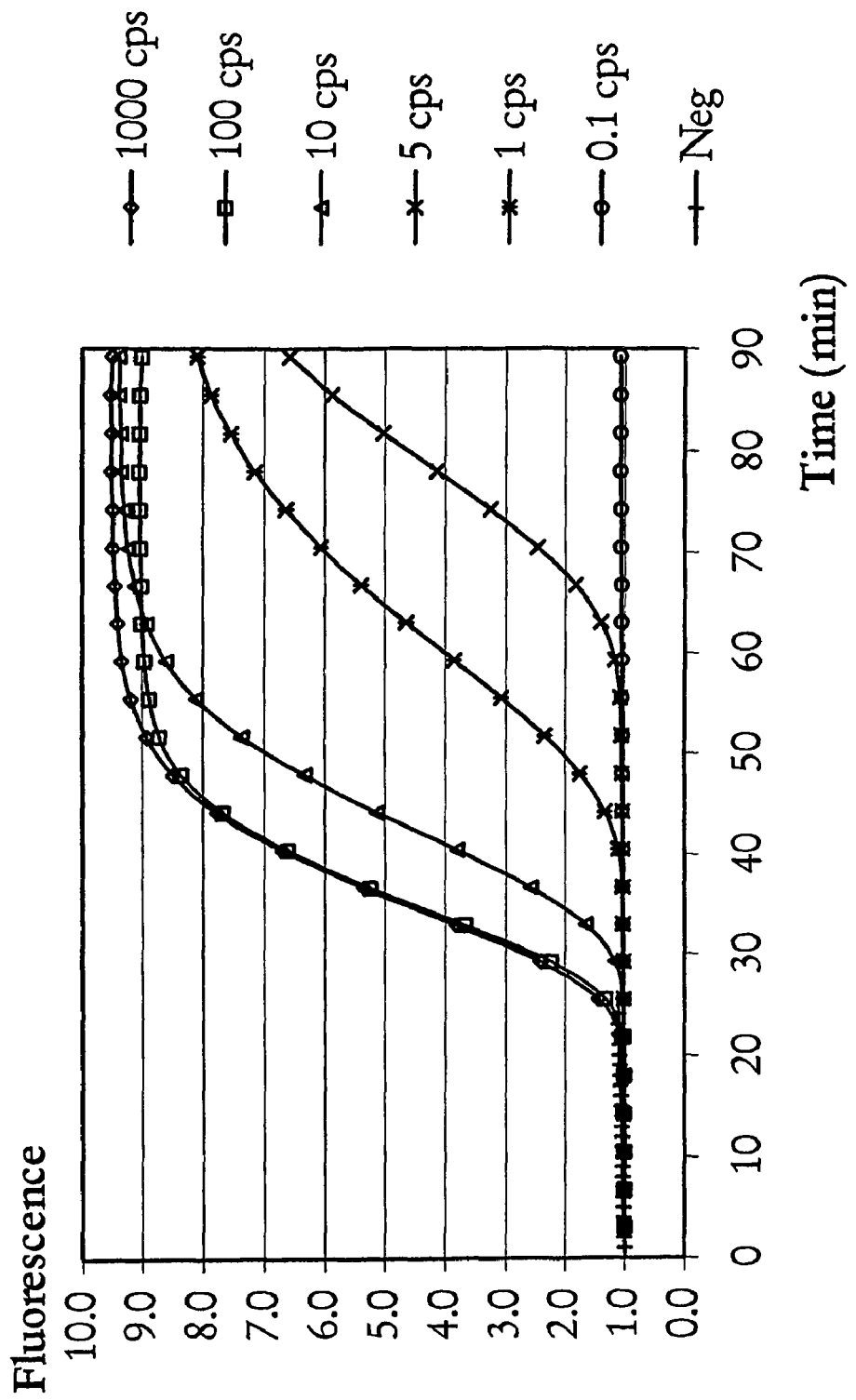
FIGS. 48-51 show the analysis of SARS-CoV genomic RNA, strain Frankfurt, with different primer/beacon mixtures. RNA was extracted from cultured SARS-CoV and amplified with 5 different SARS-CoV primer/beacon mixtures (Table 11).
Figure 49:
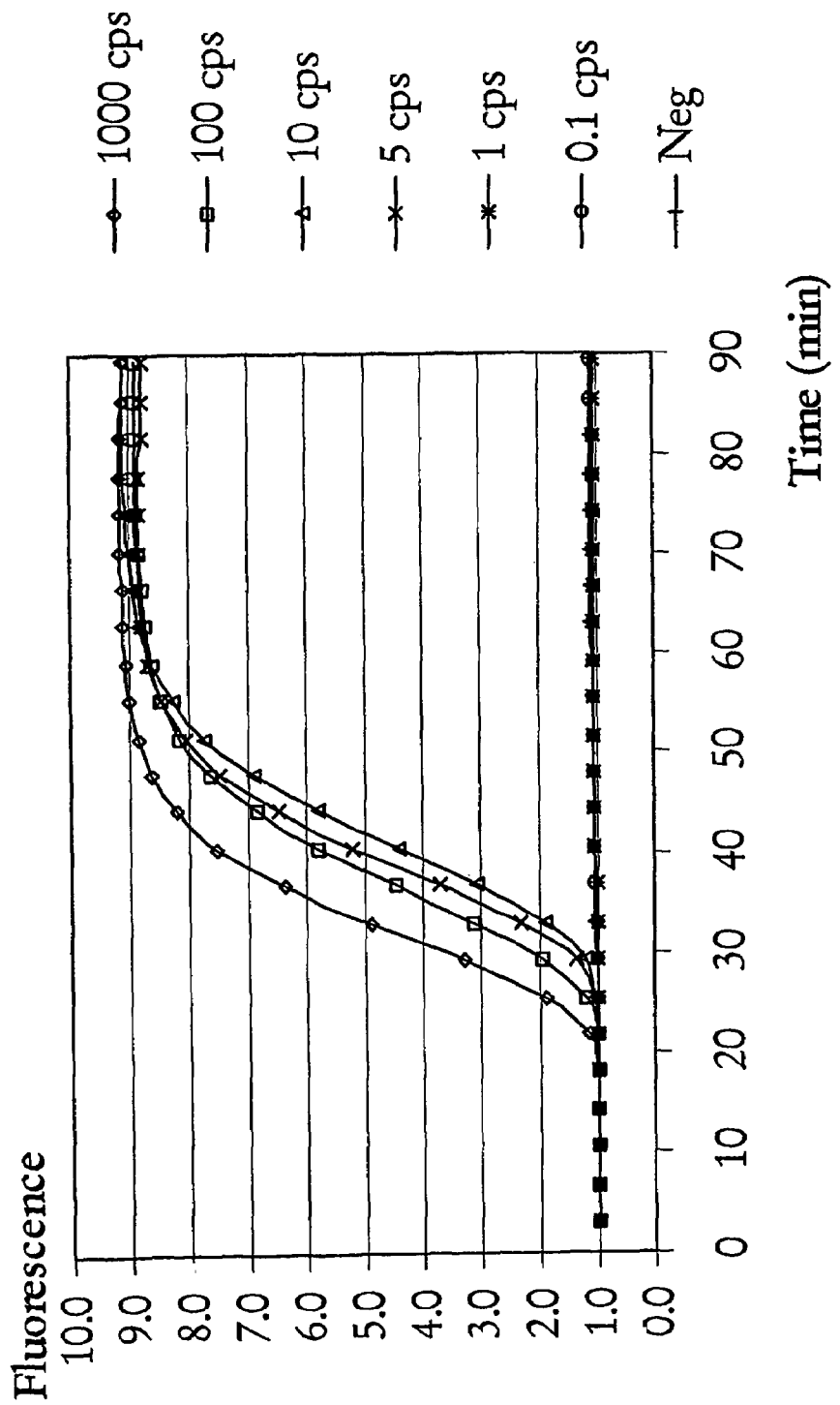
Figure 50:
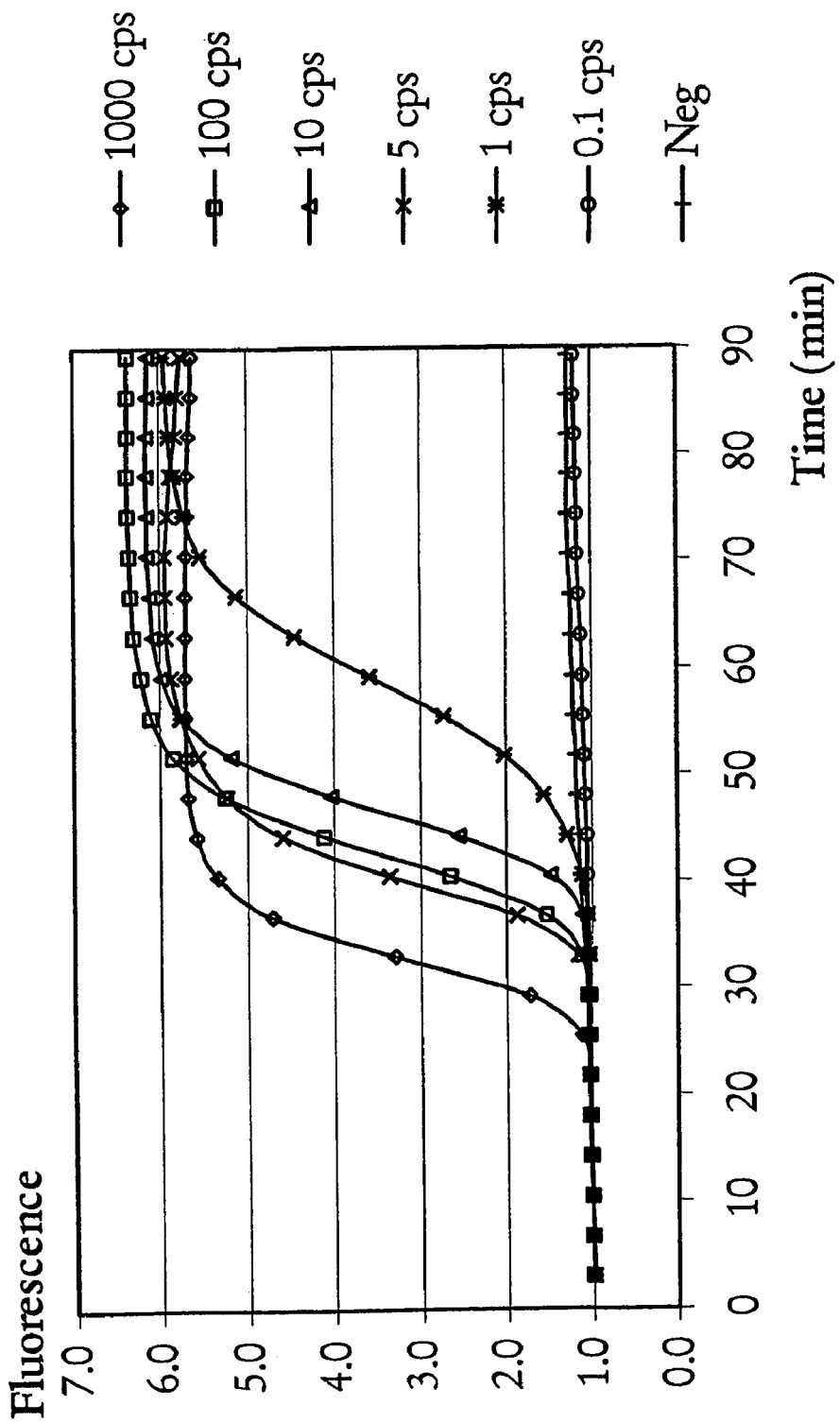
Figure 51:
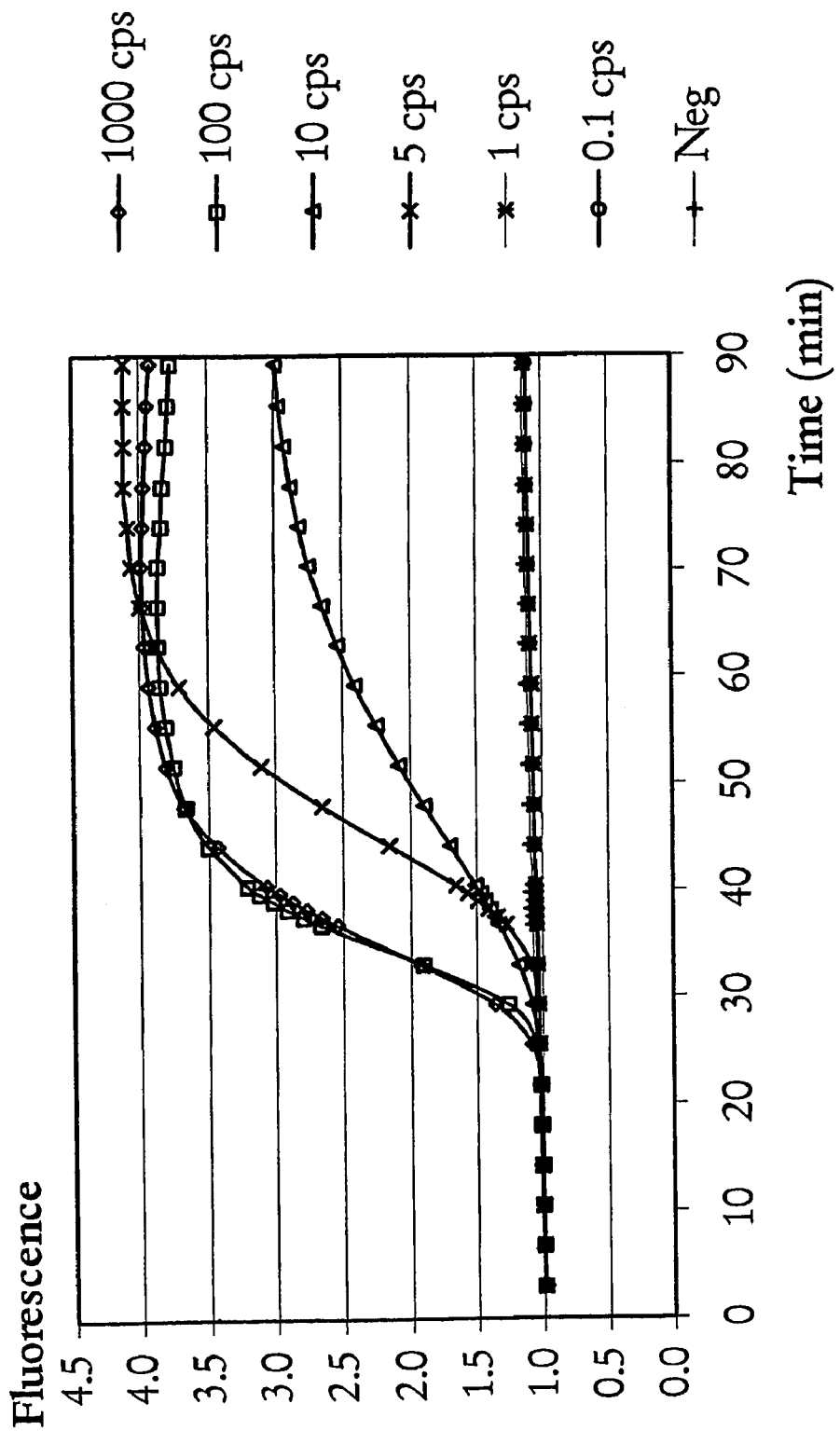
Figure 52:
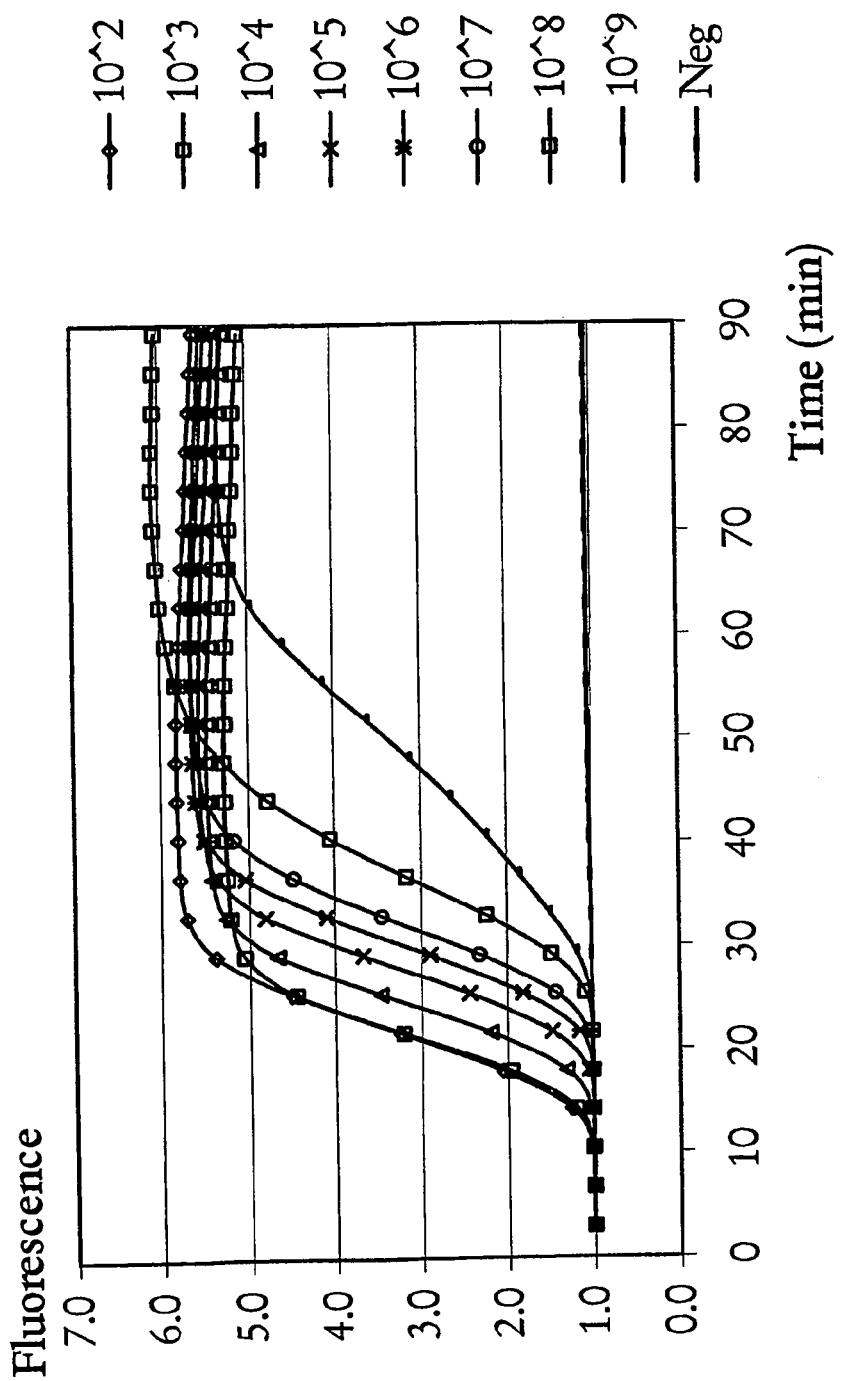
FIGS. 52-55 show an analysis of SARS-CoV genomic RNA (Rotterdam preparation) with different primer/beacon mixtures. RNA was extracted from cultured SARS-CoV and amplified with 5 different SARS-CoV primer/beacon mixtures (Table 11).
Figure 53:
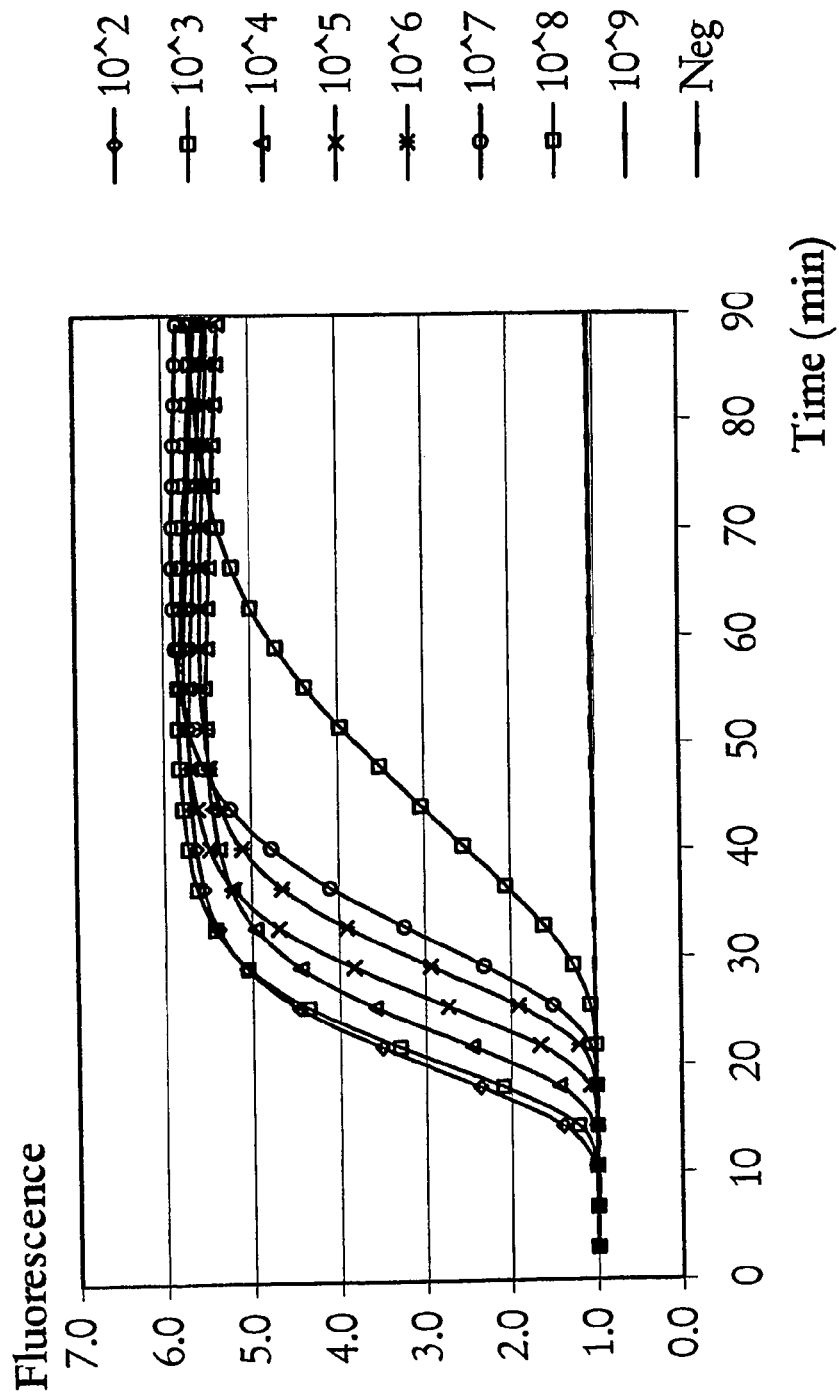
Figure 54:
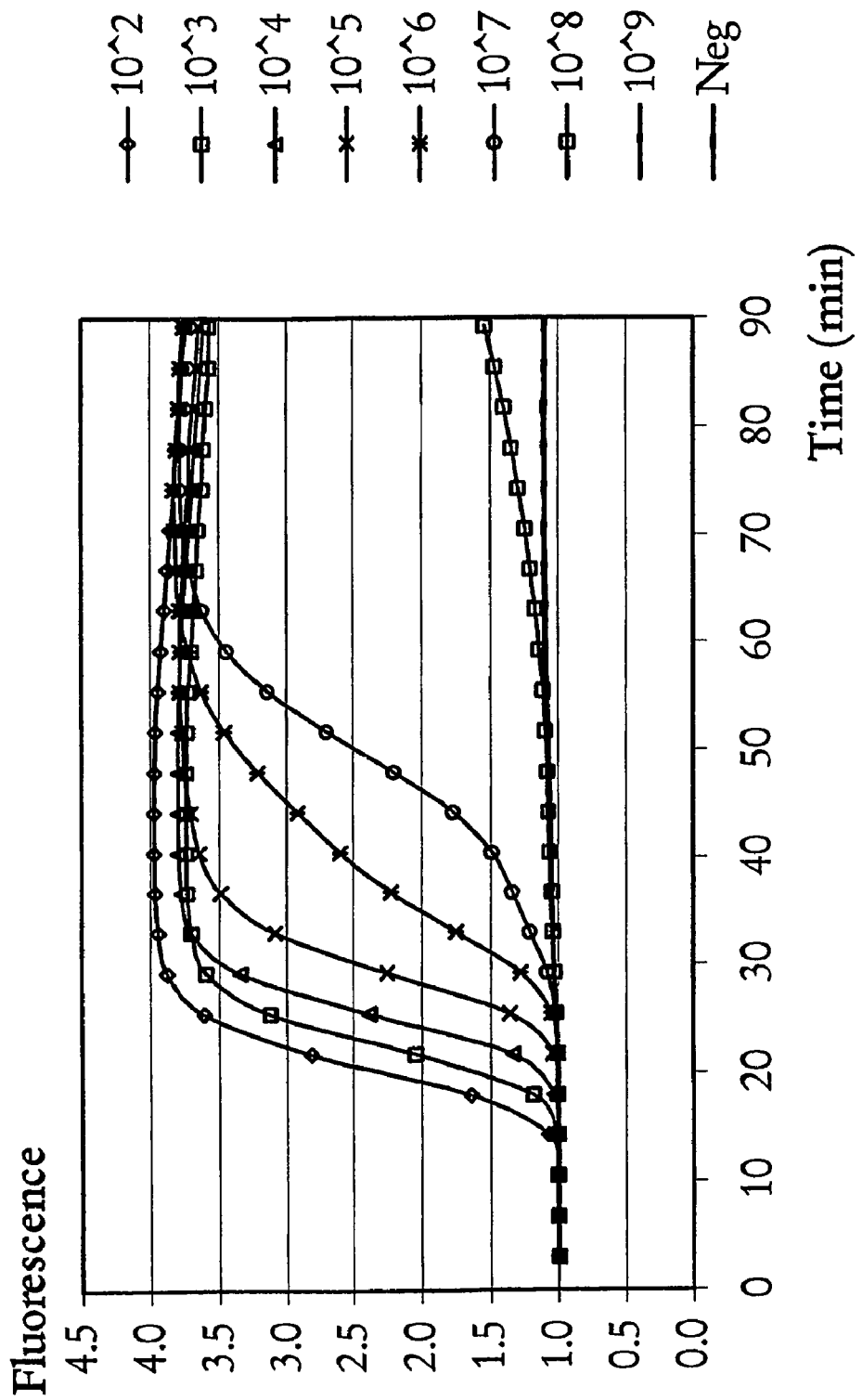
Figure 55:
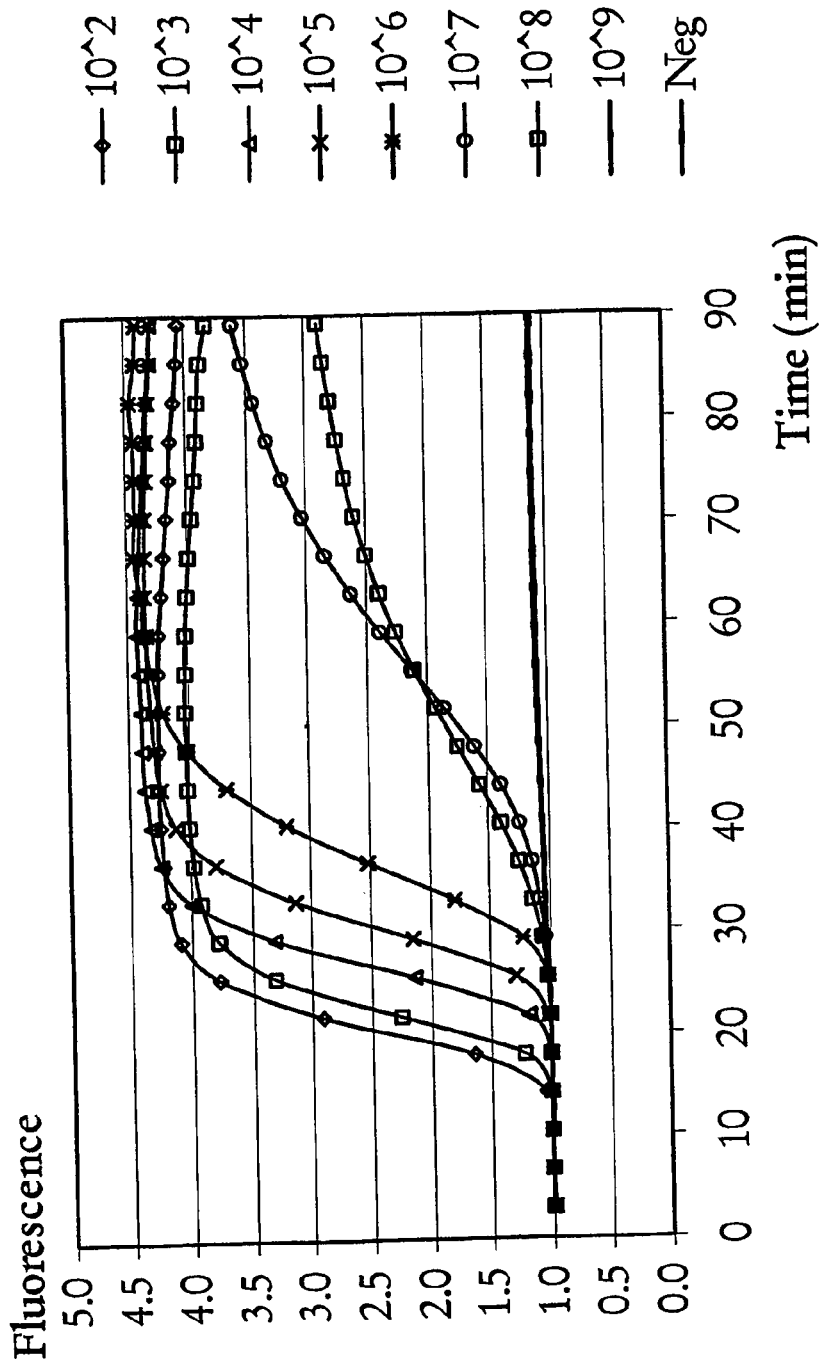
Figure 56:
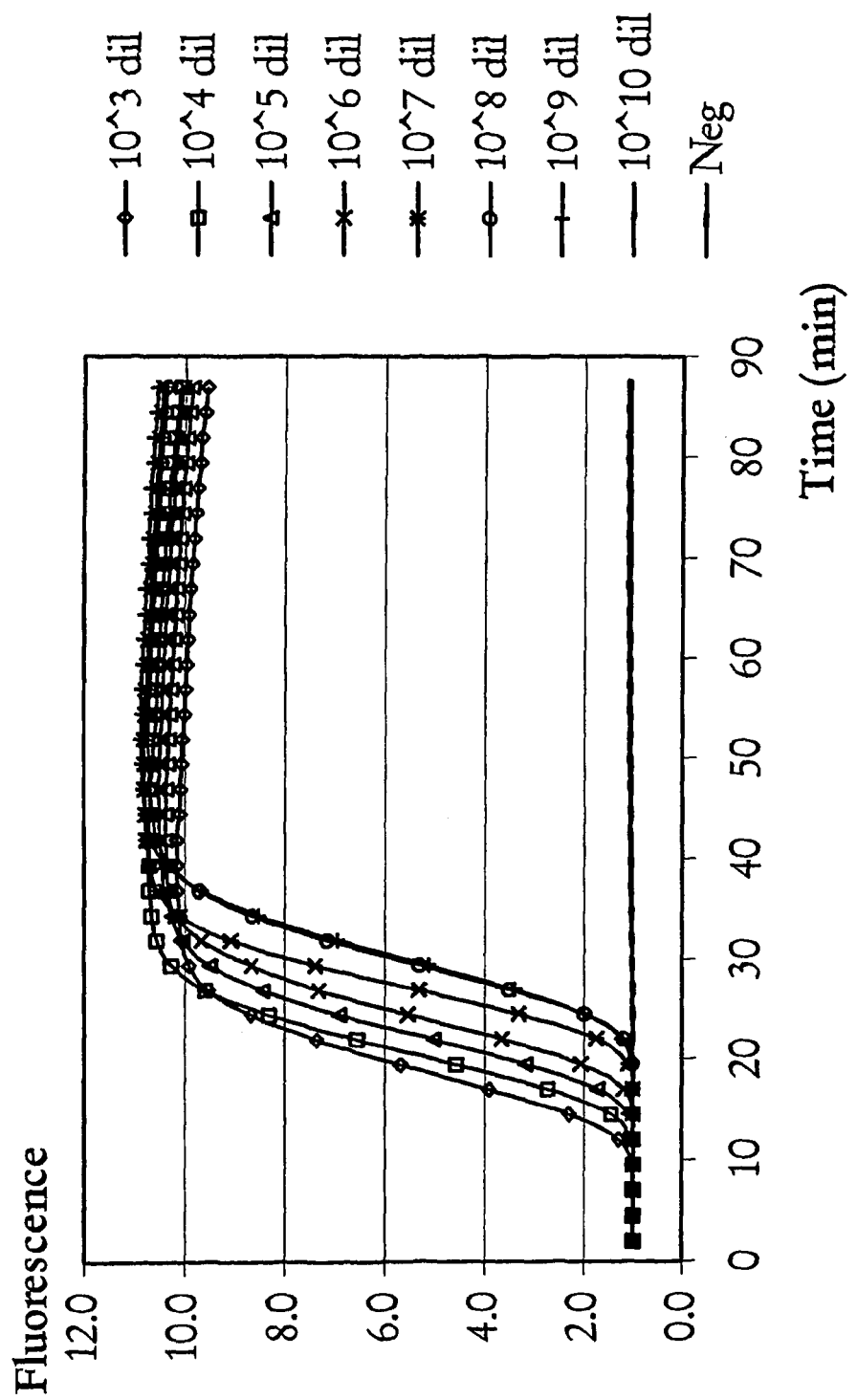
FIGS. 56-60 show an analysis of SARS-CoV genomic RNA (Rotterdam preparation) with different primer/beacon mixtures. RNA was extracted from cultured SARS-CoV and amplified with 5 different SARS-CoV primer/beacon mixtures (Table 11).
Figure 57:
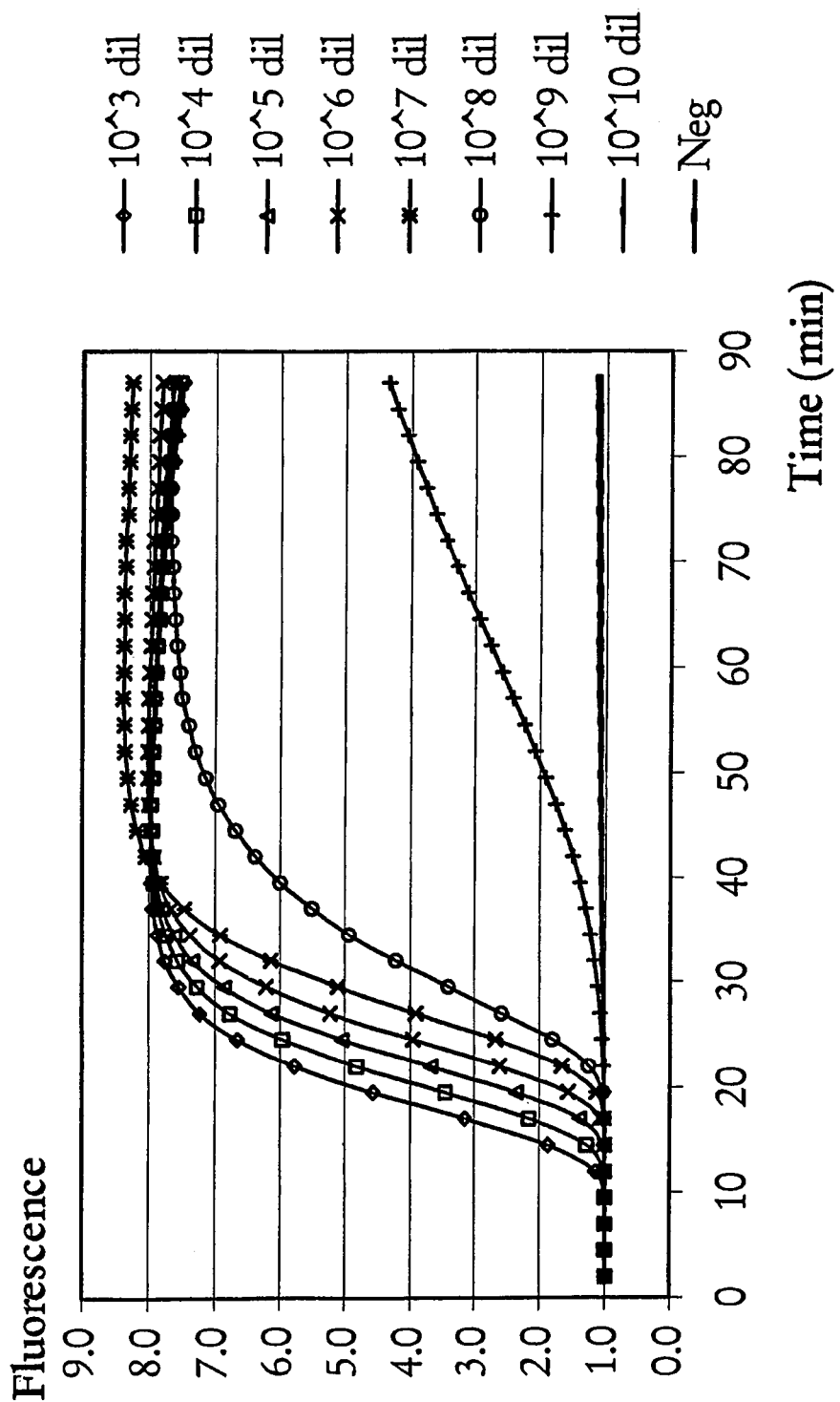
Figure 58:
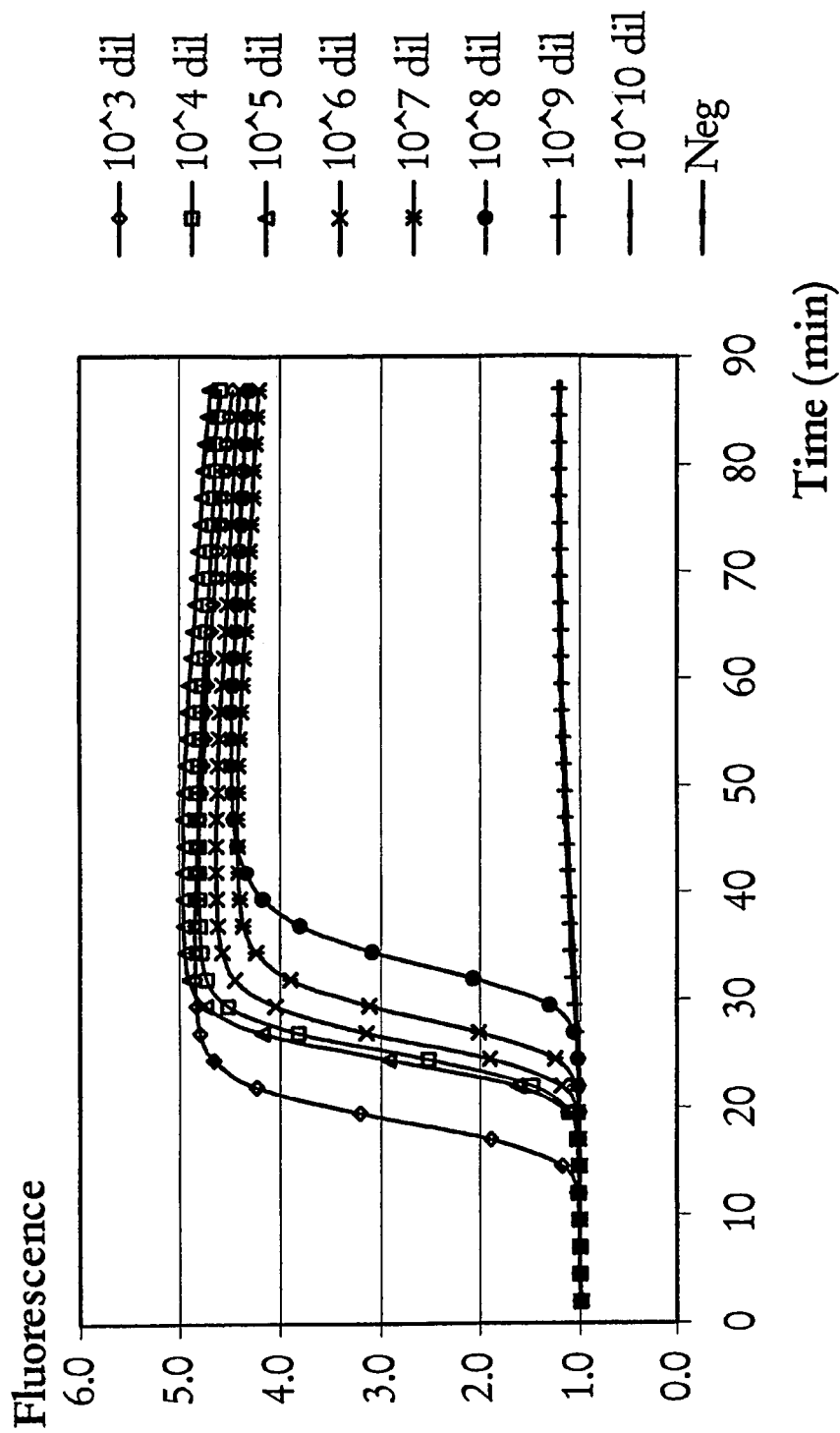
Figure 59:
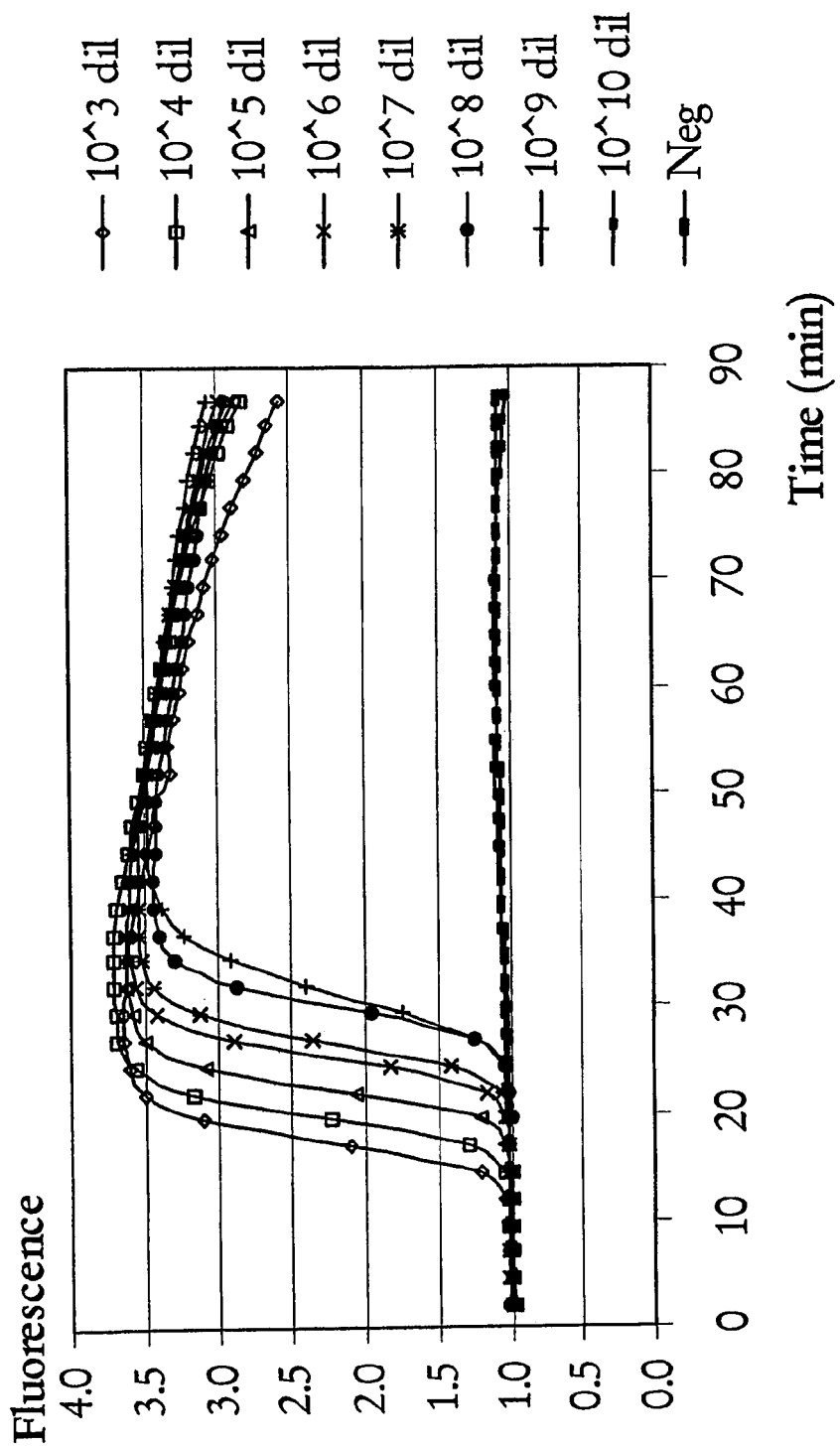
Figure 60:
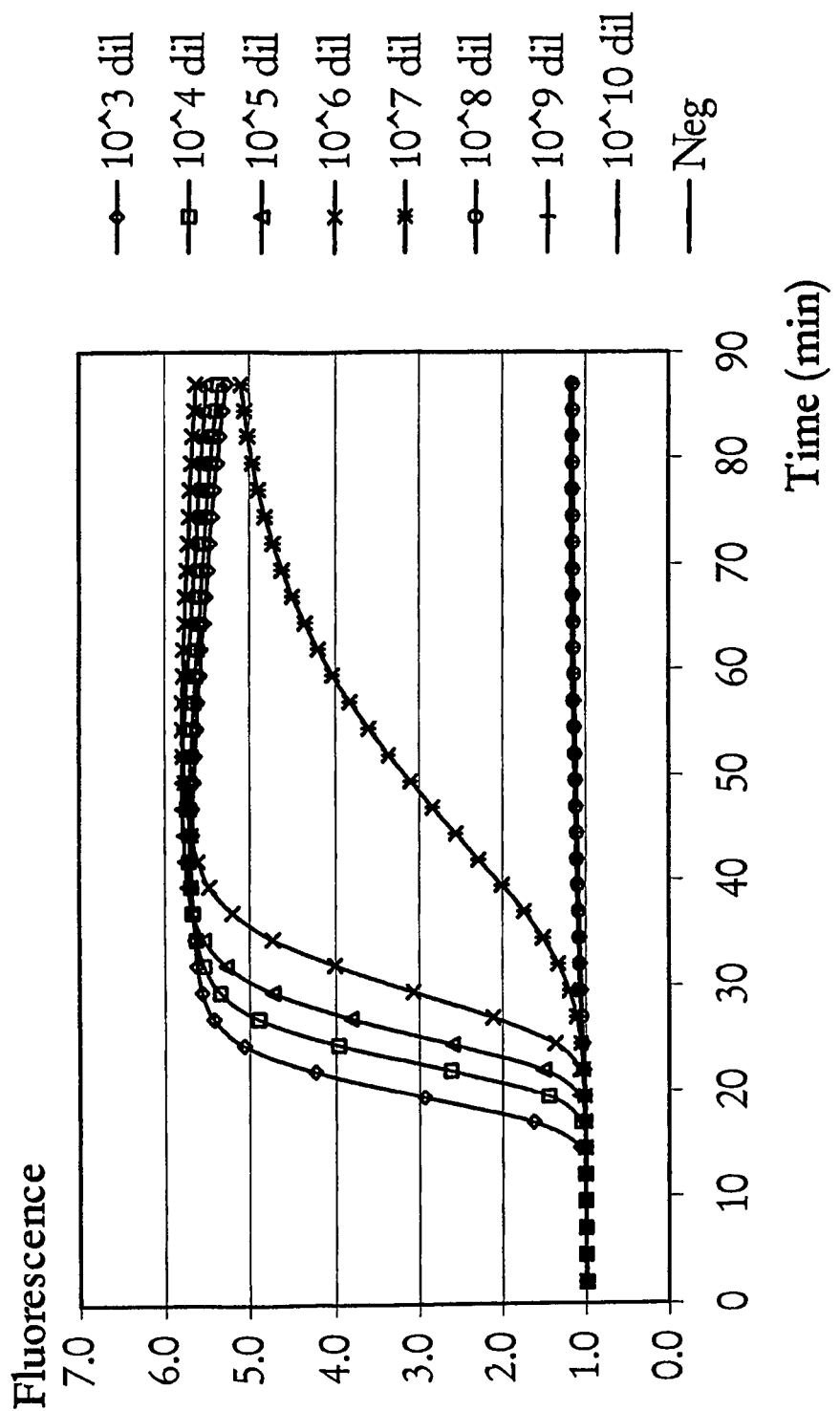

Results for the six primer combinations are shown in FIGS. 42-47 and do not identify a preferred P1 or P2 primer but rather two unrelated primer combinations being SARS-CoV 3'-NCR P1.5/P2.5 and P1.6/P2.6 (FIGS. 42 and 46 respectively). For the other primer combinations, a lower sensitivity (SARS-CoV 3'-NCR P1.5/P2.6; FIG. 43) or poorer kinetics, especially for the lower input levels (FIGS. 44, 45 and 47), were observed.

Showing "steeper" and faster (i.e. shorter TTP values) kinetics, primer pair SARS-CoV 3'-NCR P1.6/P2.6 was chosen for further evaluation and in combination with molecular beacon SARS-CoV 3'-NCR MB-1 will be referred to as primer/beacon mix SARS-CoV 3'-NCR.

Comparison of SARS-CoV Primer/Molecular Beacon Mixtures for Different Regions of the Genome:

Upon analysis of several different primer combinations in three regions of the viral genome, viz. the replicase gene, the nucleocapsid gene, and the untranslated 'leader' sequence at the 3'-end of the genome, the best performing primer/beacon mixtures for each of the regions were selected for mutual comparison. In Table 11 these primer/beacon mixtures and their individual components are summarized.

TABLE 11

SARS-CoV primer/beacon mixtures targeting different regions on the SARS-CoV viral genome and their individual constituents.

| Primer/beacon mix | P1 primer | P2 primer | Molecular beacon |
|---|---|---|---|
| SARS-CoV REP-1 | SARS-CoV REP P1.1 | SARS-CoV REP P2.2 | SARS-CoV REP MB-1 |
| SARS-CoV REP-2 | SARS-CoV REP P1.3 | SARS-CoV REP P2.3 | SARS-CoV REP MB-1 |
| SARS-CoV N-1 | SARS-CoV N P1.1 | SARS-CoV N P2.2 | SARS-CoV N MB-1 |
| SARS-CoV N-2 | SARS-CoV N P1.4 | SARS-CoV N P2.6 | SARS-CoV N MB-2 |
| SARS-CoV 3'-NCR | SARS-CoV 3'-NCR P1.6 | SARS-CoV 3'-NCR P2.6 | SARS-CoV 3'-NCR MB-1 |

Example 11

Cultured SARS-CoV Virus Strains—First Sample

A first comparison of the different primer/beacon mixtures was made on viral genomic RNA extracted from a cultured SARS-CoV specimen that was kindly provided by the Robert Koch Institute in Berlin, Germany. This cultured SARS-CoV virus originated from the SARS case cluster from Frankfurt, Germany (10). Based on this virus stock with a known concentration of virus particles (in genome equivalents (geq) per ml), a ten-fold dilution series was prepared. RNA was extracted in duplicate from 2000 geq down to 0.2 geq of the virus using SAME extraction (see "Materials and Methods" section) and finally eluted in 50 μl elution buffer. Consequently, RNA resulting from 200 geq down to 0.02 geq was amplified with five different primer/beacon mixtures that were selected for further evaluation (Table 11).

Typical analyses are shown in FIGS. 48-51 and overall results are summarized in Table 12.

TABLE 12

Analysis of SARS-CoV genomic RNA, strain Frankfurt, with different primer/beacon mixtures (Results from two analyses were compiled).

| RNA in ampl. a (geq) | SARS-CoV REP-1 | SARS-CoV REP-2 | SARS-CoV N-1 | SARS-CoV 3'-NCR |
|---|---|---|---|---|
| 200 | 2/2 | 2/2 | 2/2 | 2/2 |
| 20 | 2/2 | 2/2 | 2/2 | 2/2 |
| 2 | 2/2 | 2/2 | 2/2 | 1/2 |
| 0.2 | 2/2 | 2/2 | 2/2 | 2/2 |
| 0.1 | 1/2 | 0/2 | 2/2 | 0/2 |
| 0.02 | 0/2 | 0/2 | 0/2 | 0/2 | a = assuming 100% recovery in nucleic acid extraction

SARS-CoV N-1 and SARS-CoV REP-1 and REP-2 primer/beacon mixtures revealed the highest sensitivity. SARS-CoV N-1 was the most sensitive combination although differences with the SARS-CoV REP mixtures were minimal. SARS-CoV 3'-NCR showed intermediate sensitivity.

Example 12

Cultured SARS-CoV Virus Strains—Second Sample

For a second comparison, cultured virus from a different source was used. This virus stock originated from the Erasmus Medical Center in Rotterdam, The Netherlands. Concentration of virus particles in this virus preparation was unknown. Therefore, a limiting dilution series was prepared ranging from a 100-fold dilution of the original virus culture down to a $10^9$-fold dilution. RNA was extracted from each dilution using SAME extraction (see "Materials and Methods" section) and amplified with each of the selected primer/beacon mixtures (Table 11). Typical analyses are shown in FIGS. 52-55 and overall results of three dilution series are summarized in Table 13)

TABLE 13

Analysis of SARS-CoV genomic RNA, strain Rotterdam, with different primer/beacon mixtures (Results from three analyses were compiled).

| Virus stock dilution Factor | SARS-CoV REP-1 | SARS-CoV REP-2 | SARS-CoV N-1 | SARS-CoV 3'-NCR |
|---|---|---|---|---|
| $10^2$ | 3/3 | 3/3 | 3/3 | 3/3 |
| $10^3$ | 3/3 | 3/3 | 3/3 | 3/3 |
| $10^4$ | 3/3 | 3/3 | 3/3 | 3/3 |
| $10^5$ | 3/3 | 3/3 | 3/3 | 3/3 |
| $10^6$ | 3/3 | 3/3 | 3/3 | 3/3 |
| $10^7$ | 2/3 | 3/3 | 3/3 | 3/3 |
| $10^8$ | 1/3 | 1/3 | 2/3 | 1/3 |
| $10^9$ | 1/3 | 0/3 | 0/3 | 0/3 |
| Neg | 0/3 | 0/3 | 0/3 | 0/3 |

In line with the results found for the virus from Frankfurt, again SARS-CoV N-1 and SARS-CoV REP primer/beacon mixtures turned out to be the most sensitive combinations. Looking at the lower virus concentrations (107-109 dilutions), SARS-CoV N-1 revealed the most consistent results. However, SARS-CoV REP-1 was the only primer/beacon mixture to detect the $10^9$-fold dilution albeit in only one out of three tests.

Example 13

Cultured SARS-CoV Virus Strains—Third Sample

For a third comparison, again cultured virus from the Erasmus Medical Center in Rotterdam, The Netherlands, was used. Concentration of virus particles in this virus preparation was unknown. Therefore, a limiting dilution series was prepared ranging from a $10^3$-fold dilution of the original virus culture down to a $10^{10}$-fold dilution. RNA was extracted from each dilution using SAME extraction (see "Materials and Methods" section) and amplified with each of the selected primer/beacon mixtures (Table 11). Analyses are shown in FIGS. 56-60. In this comparison, SARS-CoV REP-1 (FIG. 56), SARS CoV REP-2 (FIG. 57) and SARS-CoV N-2 (FIG. 59) appeared to be the most sensitive primer/beacon mixtures. However, the differences with SARS CoV N-1 (FIG. 58) was only one 10-fold dilution. SARS CoV 3'-NCR (FIG. 60) again revealed the lowest sensitivity as was also observed in the other comparisons that were made on cultured viral materials.

BIBLIOGRAPHY (1) Marra, M A, Jones, S J M, Astell, C R et al. The genomic sequence of the SARS-associated Coronavirus. www-.sciencexpress.org/1 May 2003/page 1-5/10.1126/science.1085953

(2) Rota, P A, Oberste M S, Monroe, S S et al. Characterization of a Novel Coronavirus Associated with Severe Acute Respiratory Syndrome. www.sciencexpress.org/1 May 2003/Page 1-7/10.1126/science.1085952

(3) Anonymous. Acute respiratory syndrome in China—update 3: disease outbreak reported. Geneva: World Health Organization, February 2003.

(4) Update: outbreak of severe acute respiratory syndrome—worldwide, 2003. MMWR Morb Mortal Wkly Rep 2003; 52:241-8.

(5) Tsang K W, Ho P L, Ooi G C, et al. A cluster of cases of severe acute respiratory syndrome in Hong Kong. N Engl J Med 2003; 348:1975-83.

(6) Lee N, Hui D, Wu A, et al. A major outbreak of severe acute respiratory syndrome in Hong Kong. N Engl J Med 2003; 348:1984-92.

(7) Poutanen S M, Low D E, Henry B, et al. Identification of severe acute respiratory syndrome in Canada. N Engl J Med 2003; 348:1993-2003.

(8) Bitsch, A. et al., J. Infect. Dis 167, 740-743, 1993

(9) Meyer, T. et al., Mol. Cell Probes. 8, 261-271, 1994

(10) Drosten, C, Gunther, S, Preiser, W et al. Identification of a novel Coronavirus in patients with Severe Acute Respiratory Syndrome. N Engl J Med, 2003, 348, 1967-76.

(12) Compton J. Nucleic acid sequence based amplification—Nature 1991 Volume 350 pages 91-2.

(13) Ksiazek, T G, Erdman, D, Goldsmith, C S et al. A Novel Coronavirus Associated with Severe Acute Respiratory Syndrome. N Engl J Med, 2003, 348, 1953-66.

(14) Sawicki G. S. et al. Adv. Exp. Med. Biol., volume 440, from page 215, 1998.

(15) Lai M. M. C. et al. in Fields Virology, D. M. Knipe, P. M. Howley, Eds (Lippincott Williams and Wilkins, New York, $4^{th}$ edition, 2001), Ch 35.

(16) Tyagi, S. and Kramer, K. R. (1996) Molecular beacons: probes that fluoresce upon hybridization. Nature Biotechnology; 14:303-308.

(17) Zuker, M. (2003) Mfold web server for nucleic acid folding and hybridization prediction. *Nucleic Acids Research* 31, 3406-3415.

(18) Kenten, J. H., Gudibande, S., Link, J., Willey, J. J., Curfman, B., Major, E. O., Massey, R. J. (1992) Improved Electrochemiluminescent label for DNA probe assays for HIV-1 PCR products. *Clinical Chemistry* 38, 873-879.

(19) Deiman, B.; van Aarle, P.; and Sillekens, P. (2002) Characteristics and applications of nucleic acid sequence-based amplification (NASBA). Molecular Biotechnology 20, 163-179

The invention claimed is:

1. A pair of oligonucleotides for amplification of a target sequence of the genome of SARS coronavirus, said pair selected from the group consisting of:
   (a) a first oligonucleotide sequence of: SEQ ID NO:4: TAGTAGCTGT ACCGACTGGT TATGTT, or the complementary nucleotide sequence of SEQ ID NO:4, and a second oligonucleotide sequence of: SEQ ID NO:7: GAAGCTATTC GTCACGTTCG, or the complementary nucleotide sequence of SEQ ID NO:7;
   (b) a first oligonucleotide sequence of SEQ ID NO:3: TCCACCAGGT GACCAGTTTA AACATCTT, or the complementary nucleotide sequence of SEQ ID NO:3, and a second oligonucleotide sequence of SEQ ID NO:8: TGCGTGGATT GGCTTTGATG T, or the complementary nucleotide sequence of SEQ ID NO:8;
   (c) a first oligonucleotide sequence of SEQ ID NO:25: TTGGCATGGA AGTCACACCT T, or the complementary nucleotide sequence of SEQ ID NO:25, and a second oligonucleotide sequence of SEQ ID NO:29: CAGAACAAAC CCAAGGAAAT T, or the complementary nucleotide sequence of SEQ ID NO:29; and any combination thereof.

2. A pair of oligonucleotides for amplification of a target sequence located within the gene encoding the nucleocapsid protein of the SARS coronavirus, said pair consisting essentially of:

a first oligonucleotide being 10-50 nucleotides in length and comprising at least 10 contiguous nucleotides of a nucleotide sequence selected from the group consisting of:

SEQ ID NO:15: TCAGCCCCAG ATGGTACTTC T; and
the complementary nucleotide sequence of SEQ ID NO:15; and a second oligonucleotide being 10-50 nucleotides in length and comprising at least 10 contiguous nucleotides of a nucleotide sequence selected from the group consisting of:

SEQ ID NO:19: AGATTCCCTC GAGGCCAGGG CGT; and
the complementary nucleotide sequence of SEQ ID NO:19.

3. A pair of oligonucleotides for amplification of a target sequence of the genome of SARS coronavirus, said pair selected from the group consisting of:
 (a) a first oligonucleotide sequence of: SEQ ID NO:10: aattctaata cgactcacta tagggAACAT AACCAGTCGG TACAGCTACT A, and a second oligonucleotide sequence of: SEQ ID NO:7: GAAGCTATTC GTCACGTTCG, or the complementary nucleotide sequence of SEQ ID NO:7;
 (b) a first oligonucleotide sequence of SEQ ID NO:9: aattctaata cgactcacta tagggAAGAT GTTTAAACTG GTCACCTGGT GGA, and a second oligonucleotide sequence of SEQ ID NO:8: TGCGTGGATT GGCTTTGATG T, or the complementary nucleotide sequence of SEQ ID NO: 8;
 (c) a first oligonucleotide sequence of SEQ ID NO:42: aattctaata cgactcacta tagggAAGGT GTGACTTCCA TGCCAA, and a second oligonucleotide sequence of SEQ ID NO:29: CAGAACAAAC CCAAGGAAAT T, or the complementary nucleotide sequence of SEQ ID NO:29; and any combination thereof.

4. An oligonucleotide probe to detect an amplified target sequence located within the genome of SARS coronavirus, said target sequence amplified with the pair of oligonucleotides according to claim 1, wherein the probe comprises a molecular beacon selected from the group consisting of:

SEQ ID NO: 13: 5'- [6-FAM]-ccatgggCTGTCATGCAACTAGAGATGCTGTcccatgg- [DabSyl]-3';
SEQ ID NO: 45: 5'- [6-FAM]-cgcgatGTTCGTGCGTGGATTGGCTTatcgcg- [DabCyl]-3';
and SEQ ID NO: 30: 5'-[6-FAM]-ccatggACCAAGACCTAATCAGACAAccatgg- [DabSyl]-3'.

5. A method for detecting SARS coronavirus nucleic acid in a sample, comprising:
 (a) employing the sample in a nucleic acid amplification reaction under conditions whereby amplification of SARS coronavirus nucleic acid can occur; and
 (b) detecting amplified SARS coronavirus nucleic acid in the sample using the pair of oligonucleotides of claim 1.

6. A method for detecting SARS coronavirus nucleic acid in a sample, comprising:
 (a) contacting the sample with the pair of oligonucleotides of claim 1 under conditions whereby amplification of SARS coronavirus nucleic acid can occur; and
 (b) detecting amplified SARS coronavirus nucleic acid.

7. The method according to claim 6, wherein detecting the amplified nucleic acid comprises contacting the amplified SARS coronavirus nucleic acid with an oligonucleotide probe under conditions whereby hybridization can occur, said probe comprising a molecular beacon probe selected from the group consisting of:

SEQ ID NO: 13: 5'- [6-FAM]-ccatgggCTGTCATGCAACTAGAGATGCTGTeccatgg-[DabSyl]-3'; SEQ ID NO: 45: 5'- [6-FAM]-cgcgatGTTCGTGCGTGGATTGGCTTatcgcg-[DabCyl]-3'; and SEQ ID NO: 30: 5'-[6-FAM]-ccatggACCAAGACCTAATCAGACAAccatgg-[DabSyl]-3'.---.

8. The method according to claim 6, wherein the nucleic acid amplification comprises a NASBA transcription based amplification technique, and the first oligonucleotide is operably linked to a promoter sequence recognized by a DNA dependent RNA polymerase.

9. A test kit for the detection of SARS coronavirus in a sample, comprising:
 the pair of oligonucleotides according to claim 1,
 an oligonucleotide, for use as a probe, said probe comprising a molecular beacon probe selected from the group consisting of:

SEQ ID NO: 13: 5'- [6-FAM]-ccatgggCTGTCATGCAACTAGAGATGCTGTeccatgg-[DabSyl]-3'; SEQ ID NO: 45: 5'- [6-FAM]-cgcgatGTTCGTGCGTGGATTGGCTTatcgcg-[DabCyl]-3'; and SEQ ID NO: 30: 5'-[6-FAM]-ccatggACCAAGACCTAATCAGACAAccatgg-[DabSyl]-3'.---.

and
 suitable amplification reagents.

10. The test kit according to claim 9, wherein the suitable amplification reagents enable a NASBA transcription based amplification technique.

11. The pair of oligonucleotides according to claim 2, wherein the first oligonucleotide is operably linked to a promoter sequence recognized by a DNA dependent RNA polymerase.

12. The pair of oligonucleotides according to claim 11, wherein the first oligonucleotide consists of the nucleotide sequence of:

SEQ ID NO: 39: aattctaata cgactcacta tagggAGAAG TACCATCTGG GGCTGA.

13. An oligonucleotide probe to detect an amplified target sequence located within the genome of SARS coronavirus, said target sequence amplified with the pair of oligonucleotides according to claim 2, wherein the probe comprises a molecular beacon of:

SEQ ID NO: 22: 5'[6-FAM]-ccatgggCTACTACCGAAGAGCTACCCGACGAcccatgg- [DabSyl]-3'.

14. A method for detecting SARS coronavirus nucleic acid in a sample, comprising:
 (a) employing the sample in a nucleic acid amplification reaction under conditions whereby amplification of SARS coronavirus nucleic acid can occur; and
 (b) detecting amplified SARS coronavirus nucleic acid in the sample using the pair of oligonucleotides of claim 2.

15. A method for detecting SARS coronavirus nucleic acid in a sample, comprising:
 (a) contacting the sample with the pair of oligonucleotides of claim 2 under conditions whereby amplification of SARS coronavirus nucleic acid can occur; and
 (b) detecting amplified SARS coronavirus nucleic acid.

16. The method according to claim 15, wherein detecting the amplified nucleic acid comprises contacting the amplified SARS coronavirus nucleic acid with an oligonucleotide probe under conditions whereby hybridization can occur, said probe comprising the oligonucleotide probe of

```
SEQ ID NO: 22: 5'-'6-FAM]-
ccatgggCTACTACCGAAGAGCTACCCGACGAcccatgg-
[DabSyl]-3'.--.
```

17. The method according to claim 15, wherein the nucleic acid amplification comprises a NASBA transcription based amplification technique, and the first oligonucleotide is operably linked to a promoter sequence recognized by a DNA dependent RNA polymerase.

18. A test kit for the detection of SARS coronavirus in a sample, comprising:
the pair of oligonucleotides according to claim 2,
an oligonucleotide, for use as a probe, said probe comprising an oligonucleotide probe of

```
SEQ ID NO: 22: 5'-[6-FAM]-
ccatgggCTACTACCGAAGAGCTACCCGACGAcccatgg-
[DabSyl]-3',--.
``` and
suitable amplification reagents.

19. The test kit according to claim 18, wherein the suitable amplification reagents enable a NASBA transcription based amplification technique.

20. A test kit for the detection of SARS coronavirus in a sample, comprising:
the pair of oligonucleotides according to claim 3,
an oligonucleotide, for use as a probe, said probe comprising a molecular beacon probe selected from the group consisting of:

```
SEQ ID NO: 13: 5'- [6-FAM]-
ccatgggCTGTCATGCAACTAGAGATGCTGTeccatgg-
[DabSyl]-3'; SEQ ID NO: 45: 5'-
[6-FAM]-cgcgatGTTCGTGCGTGGATTGGCTTatcgcg-
[DabCyl]-3'; and SEQ ID NO: 30: 5'-[6-FAM]-
ccatggACCAAGACCTAATCAGACAAccatgg-
[DabSyl]-3', and
``` suitable amplification reagents.

21. The test kit according to claim 20, wherein the suitable amplification reagents enable a NASBA transcription based amplification technique.

* * * * *

UNITED STATES PATENT AND TRADEMARK OFFICE
CERTIFICATE OF CORRECTION

PATENT NO.       : 8,106,172 B2
APPLICATION NO.  : 10/559949
DATED            : January 31, 2012
INVENTOR(S)      : Sillekens et al.

Page 1 of 1

It is certified that error appears in the above-identified patent and that said Letters Patent is hereby corrected as shown below:

Column 33, Line 32: correct "concentrations (107-109"
    to read -- concentrations ($10^7$-$10^9$ --

Column 52, Claim 7, Line 6:
    correct "ccatgggCTGTCATGCAACTAGAGATGCTGTecccatgg"
    to read -- ccatgggCTGTCATGCAACTAGAGATGCTGTccccatgg --
  Claim 9, Line 24:
    correct "ccatgggCTGTCATGCAACTAGAGATGCTGTecccatgg"
    to read -- ccatgggCTGTCATGCAACTAGAGATGCTGTccccatgg --

Column 54, Claim 20, Line 15:
    correct "ccatgggCTGTCATGCAACTAGAGATGCTGTecccatgg"
    to read -- ccatgggCTGTCATGCAACTAGAGATGCTGTccccatgg --

Signed and Sealed this
Eighth Day of May, 2012

David J. Kappos
*Director of the United States Patent and Trademark Office*

SEQUENCE LISTING

```
<160> NUMBER OF SEQ ID NOS: 47

<210> SEQ ID NO 1
<211> LENGTH: 134
<212> TYPE: DNA
<213> ORGANISM: SARS Coronavirus
```

```
<400> SEQUENCE: 1
tacctctcca gctaggattt tctacaggtg ttaacttagt agctgtaccg actggttatg    60
ttgacactga aataacaca gaattcacca gagttaatgc aaaacctcca ccaggtgacc   120
agtttaaaca tctt                                                    134

<210> SEQ ID NO 2
<211> LENGTH: 89
<212> TYPE: DNA
<213> ORGANISM: SARS Coronavirus

<400> SEQUENCE: 2
atgaattacc aagtcaatgg ttaccctaat atgtttatca cccgcgaaga agctattcgt    60
cacgttcgtg cgtggattgg ctttgatgt                                     89

<210> SEQ ID NO 3
<211> LENGTH: 28
<212> TYPE: DNA
<213> ORGANISM: Artificial
<220> FEATURE:
<223> OTHER INFORMATION: Amplification primer

<400> SEQUENCE: 3
tccaccaggt gaccagttta aacatctt                                      28

<210> SEQ ID NO 4
<211> LENGTH: 26
<212> TYPE: DNA
<213> ORGANISM: Artificial
<220> FEATURE:
<223> OTHER INFORMATION: Amplification primer

<400> SEQUENCE: 4
tagtagctgt accgactggt tatgtt                                        26

<210> SEQ ID NO 5
<211> LENGTH: 23
<212> TYPE: DNA
<213> ORGANISM: Artificial
<220> FEATURE:
<223> OTHER INFORMATION: Amplification primer

<400> SEQUENCE: 5
tacctctcca gctaggattt tct                                           23

<210> SEQ ID NO 6
<211> LENGTH: 24
<212> TYPE: DNA
<213> ORGANISM: Artificial
<220> FEATURE:
<223> OTHER INFORMATION: Amplification primer

<400> SEQUENCE: 6
atgaattacc aagtcaatgg ttac                                          24

<210> SEQ ID NO 7
<211> LENGTH: 20
<212> TYPE: DNA
<213> ORGANISM: Artificial
<220> FEATURE:
<223> OTHER INFORMATION: Amplification primer

<400> SEQUENCE: 7
gaagctattc gtcacgttcg                                               20
```

```
<210> SEQ ID NO 8
<211> LENGTH: 21
<212> TYPE: DNA
<213> ORGANISM: Artificial
<220> FEATURE:
<223> OTHER INFORMATION: Amplification primer

<400> SEQUENCE: 8
tgcgtggatt ggctttgatg t                                              21

<210> SEQ ID NO 9
<211> LENGTH: 53
<212> TYPE: DNA
<213> ORGANISM: Artificial
<220> FEATURE:
<223> OTHER INFORMATION: Amplification primer

<400> SEQUENCE: 9
aattctaata cgactcacta tagggaagat gtttaaactg gtcacctggt gga           53

<210> SEQ ID NO 10
<211> LENGTH: 51
<212> TYPE: DNA
<213> ORGANISM: Artificial
<220> FEATURE:
<223> OTHER INFORMATION: Amplification primer

<400> SEQUENCE: 10
aattctaata cgactcacta tagggaacat aaccagtcgg tacagctact a             51

<210> SEQ ID NO 11
<211> LENGTH: 48
<212> TYPE: DNA
<213> ORGANISM: Artificial
<220> FEATURE:
<223> OTHER INFORMATION: Amplification primer

<400> SEQUENCE: 11
aattctaata cgactcacta tagggagaaa atcctagctg gagaggta                 48

<210> SEQ ID NO 12
<211> LENGTH: 56
<212> TYPE: DNA
<213> ORGANISM: SARS Coronavirus

<400> SEQUENCE: 12
gttcgtgcgt ggattggctt tgatgtagag ggctgtcatg caactagaga tgctgt        56

<210> SEQ ID NO 13
<211> LENGTH: 38
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' 6-FAM label
<220> FEATURE:
<221> NAME/KEY: misc_feature
<222> LOCATION: (38)..(38)
<223> OTHER INFORMATION: 3' DabSyl label

<400> SEQUENCE: 13
ccatgggctg tcatgcaact agagatgctg tcccatgg                            38
```

-continued

```
<210> SEQ ID NO 14
<211> LENGTH: 53
<212> TYPE: DNA
<213> ORGANISM: SARS Coronavirus

<400> SEQUENCE: 14
tcagccccag atggtacttc tattacctag gaactggccc agaagcttca ctt          53

<210> SEQ ID NO 15
<211> LENGTH: 21
<212> TYPE: DNA
<213> ORGANISM: Artificial
<220> FEATURE:
<223> OTHER INFORMATION: Amplification primer

<400> SEQUENCE: 15
tcagccccag atggtacttc t                                             21

<210> SEQ ID NO 16
<211> LENGTH: 26
<212> TYPE: DNA
<213> ORGANISM: Artificial
<220> FEATURE:
<223> OTHER INFORMATION: Amplification primer

<400> SEQUENCE: 16
taggaactgg cccagaagct tcactt                                        26

<210> SEQ ID NO 17
<211> LENGTH: 123
<212> TYPE: DNA
<213> ORGANISM: SARS Coronavirus

<400> SEQUENCE: 17
aggtttaccc aataatactg cgtcttggtt cacagctctc actcagcatg gcaaggagga   60
acttagattc cctcgaggcc agggcgttcc aatcaacacc aatagtggtc cagatgacca  120
aat                                                                123

<210> SEQ ID NO 18
<211> LENGTH: 23
<212> TYPE: DNA
<213> ORGANISM: Artificial
<220> FEATURE:
<223> OTHER INFORMATION: Amplification primer

<400> SEQUENCE: 18
aggtttaccc aataatactg cgt                                           23

<210> SEQ ID NO 19
<211> LENGTH: 23
<212> TYPE: DNA
<213> ORGANISM: Artificial
<220> FEATURE:
<223> OTHER INFORMATION: Amplification primer

<400> SEQUENCE: 19
agattccctc gaggccaggg cgt                                           23

<210> SEQ ID NO 20
<211> LENGTH: 22
<212> TYPE: DNA
<213> ORGANISM: Artificial
<220> FEATURE:
<223> OTHER INFORMATION: Amplification primer

<400> SEQUENCE: 20
```

```
atagtggtcc agatgaccaa at                                              22

<210> SEQ ID NO 21
<211> LENGTH: 630
<212> TYPE: DNA
<213> ORGANISM: SARS Coronavirus

<400> SEQUENCE: 21
ggctactacc gaagagctac ccgacgagtt cgtggtggtg acggcaaaat gaaagagctc     60
agccccagat ggtacttcta ttacctagga actggcccag aagcttcact tccctacggc    120
gctaacaaag aaggcatcgt atgggttgca actgagggag ccttgaatac acccaaagac    180
cacattggca cccgcaatcc taataacaat gctgccaccg tgctacaact tcctcaagga    240
acaacattgc caaaaggctt ctacgcagag ggaagcagag gcggcagtca agcctcttct    300
cgctcctcat cacgtagtcg cggtaattca agaaattcaa ctcctggcag cagtaggga    360 aattctcctg ctcgaatggc tagcggaggt ggtgaaactg ccctcgcgct attgctgcta    420
gacagattga accagcttga gagcaaagtt tctggtaaag ccaacaacaa caaggccaa    480 actgtcacta gaaatctgc tgctgaggca tctaaaaagc ctcgccaaaa acgtactgcc    540
acaaaacagt caacgtcac tcaagcattt gggagacgtg gtccagaaca acccaagga    600 aatttcgggg accaagacct aatcagacaa                                     630

<210> SEQ ID NO 22
<211> LENGTH: 39
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' 6-FAM label
<220> FEATURE:
<221> NAME/KEY: misc_feature
<222> LOCATION: (39)..(39)
<223> OTHER INFORMATION: 3' DabSyl label

<400> SEQUENCE: 22
ccatgggcta ctaccgaaga gctacccgac gacccatgg                            39

<210> SEQ ID NO 23
<211> LENGTH: 59
<212> TYPE: DNA
<213> ORGANISM: SARS Coronavirus

<400> SEQUENCE: 23
tgctccaagt gcctctgcat tctttggaat gtcacgcatt ggcatggaag tcacacctt     59

<210> SEQ ID NO 24
<211> LENGTH: 24
<212> TYPE: DNA
<213> ORGANISM: Artificial
<220> FEATURE:
<223> OTHER INFORMATION: Amplification primer

<400> SEQUENCE: 24
tgctccaagt gcctctgcat tctt                                            24

<210> SEQ ID NO 25
<211> LENGTH: 21
<212> TYPE: DNA
<213> ORGANISM: Artificial
```

-continued

```
<220> FEATURE:
<223> OTHER INFORMATION: Amplification primer

<400> SEQUENCE: 25
ttggcatgga agtcacacct t 21

<210> SEQ ID NO 26
<211> LENGTH: 128
<212> TYPE: DNA
<213> ORGANISM: SARS Coronavirus
<400> SEQUENCE: 26
ccaaactgtc actaagaaat ctgctgctga ggcatctaaa aagcctcgcc aaaaacgtac 60
tgccacaaaa cagtacaacg tcactcaagc atttgggaga cgtggtccag aacaaaccca 120
aggaaatt 128

<210> SEQ ID NO 27
<211> LENGTH: 25
<212> TYPE: DNA
<213> ORGANISM: Artificial
<220> FEATURE:
<223> OTHER INFORMATION: Amplification primer
<400> SEQUENCE: 27
ccaaactgtc actaagaaat ctgct 25

<210> SEQ ID NO 28
<211> LENGTH: 23
<212> TYPE: DNA
<213> ORGANISM: Artificial
<220> FEATURE:
<223> OTHER INFORMATION: Amplification primer
<400> SEQUENCE: 28
ctcaagcatt tgggagacgt ggt 23

<210> SEQ ID NO 29
<211> LENGTH: 21
<212> TYPE: DNA
<213> ORGANISM: Artificial
<220> FEATURE:
<223> OTHER INFORMATION: Amplification primer
<400> SEQUENCE: 29
cagaacaaac ccaaggaaat t 21

<210> SEQ ID NO 30
<211> LENGTH: 32
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' 6-FAM label
<220> FEATURE:
<221> NAME/KEY: misc_feature
<222> LOCATION: (32)..(32)
<223> OTHER INFORMATION: 3' DabSyl label
<400> SEQUENCE: 30
ccatggacca agacctaatc agacaaccat gg 32

<210> SEQ ID NO 31
<211> LENGTH: 72

```
<212> TYPE: DNA
<213> ORGANISM: SARS Coronavirus

<400> SEQUENCE: 31
tgcctatatg gaagagccct aatgtgtaaa attaatttta gtagtgctat ccccatgtga      60
ttttaatagc tt

```
<210> SEQ ID NO 38
<211> LENGTH: 22
<212> TYPE: DNA
<213> ORGANISM: Artificial
<220> FEATURE:
<223> OTHER INFORMATION: Amplification primer

<400> SEQUENCE: 38
gccaccacat tttcatcgag gc                                              22

<210> SEQ ID NO 39
<211> LENGTH: 46
<212> TYPE: DNA
<213> ORGANISM: Artificial
<220> FEATURE:
<223> OTHER INFORMATION: Amplification primer

<400> SEQUENCE: 39
aattctaata cgactcacta tagggagaag taccatctgg ggctga                    46

<210> SEQ ID NO 40
<211> LENGTH: 51
<212> TYPE: DNA
<213> ORGANISM: Artificial
<220> FEATURE:
<223> OTHER INFORMATION: Amplification primer

<400> SEQUENCE: 40
aattctaata cgactcacta tagggaagtg aagcttctgg gccagttcct a              51

<210> SEQ ID NO 41
<211> LENGTH: 49
<212> TYPE: DNA
<213> ORGANISM: Artificial
<220> FEATURE:
<223> OTHER INFORMATION: Amplification primer

<400> SEQUENCE: 41
aattctaata cgactcacta tagggaagaa tgcagaggca cttggagca                 49

<210> SEQ ID NO 42
<211> LENGTH: 46
<212> TYPE: DNA
<213> ORGANISM: Artificial
<220> FEATURE:
<223> OTHER INFORMATION: Amplification primer

<400> SEQUENCE: 42
aattctaata cgactcacta tagggaaggt gtgacttcca tgccaa                    46

<210> SEQ ID NO 43
<211> LENGTH: 44
<212> TYPE: DNA
<213> ORGANISM: Artificial
<220> FEATURE:
<223> OTHER INFORMATION: Amplification primer

<400> SEQUENCE: 43
aattctaata cgactcacta tagggggggct cttccatata ggca                     44

<210> SEQ ID NO 44
<211> LENGTH: 48
<212> TYPE: DNA
<213> ORGANISM: Artificial
<220> FEATURE:
<223> OTHER INFORMATION: Amplification primer
```

```
<400> SEQUENCE: 44
aattctaata cgactcacta tagggaagct attaaaatca catgggga                48

<210> SEQ ID NO 45
<211> LENGTH: 32
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' 6-FAM label
<220> FEATURE:
<221> NAME/KEY: misc_feature
<222> LOCATION: (32)..(32)
<223> OTHER INFORMATION: 3' DabSyl label

<400> SEQUENCE: 45
cgcgatgttc gtgcgtggat tggcttatcg cg                                 32

<210> SEQ ID NO 46
<211> LENGTH: 25
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' biotin label

<400> SEQUENCE: 46
gctgtcatgc aactagagat gctgt                                         25

<210> SEQ ID NO 47
<211> LENGTH: 32
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' 6-FAM label
<220> FEATURE:
<221> NAME/KEY: misc_feature
<222> LOCATION: (32)..(32)
<223> OTHER INFORMATION: 3' DabSyl label

<400> SEQUENCE: 47
ccatgcgcca ccacattttc atcgaggcat gg                                 32
```